US012780919B2

(12) United States Patent
Derive et al.

(10) Patent No.: US 12,780,919 B2
(45) Date of Patent: Nov. 3, 2026

(54) ANTI-TREM-1 ANTIBODIES

(71) Applicant: ALKEMYS, Vandœuvre-lès-Nancy (FR)

(72) Inventors: Marc Derive, Vandœuvre-lès-Nancy (FR); Jean-Jacques Garaud, Vandœuvre-lès-Nancy (FR); Amir Boufenzer, Vandœuvre-lès-Nancy (FR); Marine Maillefer, Vandœuvre-lès-Nancy (FR); Julie Voison-Christophe, Vandœuvre-lès-Nancy (FR); Kévin Carrasco, Vandœuvre-lès-Nancy (FR)

(73) Assignee: ALKEMYS, Vandoeuvre-lès-Nancy (FR)

( * ) Notice: Subject to any disclaimer, the term of this patent is extended or adjusted under 35 U.S.C. 154(b) by 465 days.

(21) Appl. No.: 18/566,242

(22) PCT Filed: Jun. 2, 2022

(86) PCT No.: PCT/EP2022/065140
§ 371 (c)(1),
(2) Date: Dec. 1, 2023

(87) PCT Pub. No.: WO2022/253991
PCT Pub. Date: Dec. 8, 2022

(65) Prior Publication Data

US 2024/0254225 A1 Aug. 1, 2024

(30) Foreign Application Priority Data

Jun. 2, 2021 (EP) .................................... 21305743

(51) Int. Cl.

| | |
|---|---|
| ***C07K 16/28*** | (2006.01) |
| ***A61P 37/06*** | (2006.01) |
| ***C07K 16/46*** | (2006.01) |
| *A61K 39/00* | (2006.01) |

(52) U.S. Cl.
CPC .......... *C07K 16/2803* (2013.01); *A61P 37/06* (2018.01); *C07K 16/461* (2013.01); *A61K 2039/505* (2013.01); *C07K 2317/24* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2015/0274825 A1* 10/2015 Stennicke .............. A61P 37/06 530/387.9

FOREIGN PATENT DOCUMENTS

| | | | |
|---|---|---|---|
| WO | 2013120553 | A1 | 8/2013 |
| WO | 2017152102 | A2 | 9/2017 |
| WO | 2021011678 | A1 | 1/2021 |

OTHER PUBLICATIONS

International Search Report issued on Aug. 31, 2022, in corresponding International Patent Application No. PCT/EP2022/065140, 4 pages.

* cited by examiner

*Primary Examiner* — Brad Duffy
(74) *Attorney, Agent, or Firm* — Maier & Maier, PLLC

(57) ABSTRACT

Novel anti-TREM-1 (Triggering Receptor Expressed on Myeloid cells-1) antibodies and antigen-binding fragments thereof. Also, fusion proteins that include these anti-TREM-1 antibodies and antigen-binding fragments thereof, as well as the therapeutic uses thereof for treating of a disease, such as an inflammatory or autoimmune disease, a cardiovascular disease, a cancer, or an infectious disease.

15 Claims, 23 Drawing Sheets

Specification includes a Sequence Listing.

ANTI-TREM-1 ANTIBODIES

FIELD

The present invention relates to the field of inflammation and discloses novel anti-human TREM-1 (Triggering Receptor Expressed on Myeloid cells-1) antibodies and antigen-binding fragment thereof.

BACKGROUND

TREM-1 (triggering receptor expressed on myeloid cells-1), also sometimes known as CD354, is an immunoreceptor expressed by the majority of innate immune cells, such as monocytes, macrophages, neutrophils, platelets, and dendritic cells, and by endothelial cells. The human TREM gene cluster is located on chromosome 6p21.1 and encodes six different proteins, TREM 1-5 and TLT-1 (TREM-Like Transcript-1). TREM-1 is a membrane-bound glycoprotein receptor belonging to the Ig superfamily which comprises three distinct domains: an Ig-like structure (mostly responsible for ligand binding), a transmembrane part, and a short cytoplasmic tail which associates with an adapter protein called DNAX-activation protein 12 or DAP12. Upon binding of its ligand, TREM-1 thus activates downstream signaling pathways with the help of DAP12.

As described for example in Tammaro et al. (Pharmacol Ther. 2017 September; 177:81-95), engagement of TREM-1 triggers a signaling pathway involving ZAP70 (Zeta-chain-associated protein kinase 70) and SYK (Spleen Tyrosine Kinase), the latter promoting the ensuing recruitment and tyrosine phosphorylation of adaptor molecules such as Cbl (Casitas B-lineage Lymphoma), SOS (Son of sevenless), and GRB2 (Growth Factor Receptor Binding Protein-2), which result in downstream signal transduction through PI3K, PLC-γ (Phospholipase-C-Gamma), ERK-1, ERK-2 and p38 MAPK. The activation of these pathways induces $Ca^{2+}$ mobilization, rearrangement of the actin cytoskeleton and activation of transcription factors such as NF-kB. Ultimately, TREM-1 activation notably leads to pro-inflammatory cytokines and chemokines expression and secretion, along with rapid neutrophil degranulation and oxidative burst.

TREM-1 function is to amplify, rather than initiate, inflammation by synergizing with pathogen recognition receptors (PRRs) in order to trigger an exuberant immune response. PRR engagement, including Nod-like receptors (NLRs) and Toll-like receptors (TLRs), thus induces the upregulation of TREM-1 expression and/or its mobilization and clustering at the cell membrane, which lead to its dimerization and multimerization. Said NLRs and/TLRs can be activated by DAMPs (Danger Associated Molecular Patterns) or PAMPs (Pathogen Associated Molecular Patterns). In particular, said NLR and TLR activation can occur under sterile inflammatory conditions by interaction with DAMPs and/or alarmins, or under infectious conditions by interaction with PAMPs. TREM-1 thus plays a role in amplifying inflammation, whether it is induced by an infection (infectious inflammation) or not (sterile inflammation). Accordingly, TREM-1 and its signaling pathways play a role in inflammation or hyper-inflammation triggered by an infection, such as sepsis and septic shock, but also contribute to the pathology of several non-infectious acute and chronic inflammatory diseases, including atherosclerosis, ischemia reperfusion-induced tissue injury, colitis, fibrosis and cancer.

Of note, because of its importance for amplifying, rather than initiating, inflammation, the inhibition of TREM-1 is expected to block the TREM-1-dependent amplification loop of the innate immune response and to dampen inflammation rather than totally abrogate the inflammatory response. Identifying molecules able to specifically bind and inhibit TREM-1 may be of particular relevance for the treatment of infectious inflammatory diseases and also for the treatment of non-infectious acute and chronic inflammatory diseases. Some TREM-1 inhibitors have already been described, such as inhibitory peptides including the TLT-1 peptide LR12 (WO2011/124685), currently under clinical investigation. However, so far, no TREM-1 inhibitor has been approved for therapeutical use.

Therefore, there is still a need for novel TREM-1 inhibitors that may be used to attenuate inflammation, be it infectious inflammation or sterile inflammation.

The present invention relates to novel anti-human TREM-1 antibodies and antigen-binding fragments thereof. As illustrated in the example section, the novel anti-human TREM-1 antibodies and antigen-binding fragments thereof described herein are able to bind and inhibit human TREM-1. In particular, they are able to attenuate the inflammatory response induced in an animal model of endotoxemia. Of note, the novel anti-human TREM-1 antibodies and antigen-binding fragments thereof described herein are able to inhibit the TREM-1 signaling pathway regardless of the stimulation signal with which it has been activated. They are thus able to inhibit the TREM-1 signaling pathway activated directly with a TREM-1 ligand complex or activated indirectly, for example through stimulation of various Toll-like receptors (TLRs) such as TLR2 with PGN or TLR4 with LPS.

SUMMARY

The present invention relates to an isolated anti-TREM-1 (Triggering Receptor Expressed on Myeloid cells-1) antibody or an antigen-binding fragment thereof, wherein:

a) the variable region of the heavy chain (VH) of said isolated anti-TREM-1 antibody or antigen-binding fragment thereof comprises the three following complementary-determining regions (CDRs):
   - $V_H$-CDR1: NTYIH (SEQ ID NO: 1);
   - $V_H$-CDR2: RIDPA$X_1$G$X_2$TKY$X_3$PKV$X_4$G (SEQ ID NO: 2), wherein $X_1$ is Asn (N) or Gly (G), $X_2$ is Asn (N) or Arg (R), $X_3$ is Ala (A), Asp (D), or Ser (S), $X_4$ is Gln (Q) or Lys (K); and
   - $V_H$-CDR3: H$X_5$G$X_6$TMDY (SEQ ID NO: 3), wherein $X_5$ is Tyr (Y) or Arg (R), $X_6$ is Ser (S) or Gly (G);

b) the variable region of the light chain (VL) of said isolated anti-TREM-1 antibody or antigen-binding fragment thereof comprises the three following CDRs:
   - $V_L$-CDR1: RAS$X_7$SV$X_8$NYGISF$X_9$N (SEQ ID NO: 4), wherein $X_7$ is Glu (E) or Gln (Q), $X_8$ is Asp (D) or Ser (S), $X_9$ is Met (M) or Leu (L); and
   - $V_L$-CDR2: AA$X_{10}X_{11}X_{12}X_{13}X_{14}$ (SEQ ID NO: 5), wherein $X_{10}$ is Ser (S) or Glu (E), $X_{11}$ is Asn (N) or Tyr (Y), $X_{12}$ is Gln (Q) or Arg (R), $X_{13}$ is Gly (G), Ala (A), or Lys (K), $X_{14}$ is Ser (S) or Arg (R); and
   - $V_L$-CDR3: QQS$X_{15}X_{16}X_{17}$P$X_{18}$T (SEQ ID NO: 6), wherein $X_{15}$ is Lys (K), Arg (R), or Ser (S), $X_{16}$ is Glu (E), His (H), or Asn (N), $X_{17}$ is Val (V) or Phe (F), $X_{18}$ is Trp (W) or Tyr (Y).

In one embodiment, the isolated anti-TREM-1 antibody or antigen-binding fragment thereof comprises the following CDRs:

$V_H$-CDR1: NTYIH (SEQ ID NO: 1), $V_H$-CDR2: RIDPAGGRTKYDPKVKG (SEQ ID NO: 7), $V_H$-CDR3:

HYGGTMDY (SEQ ID NO: 8), $V_L$-CDR1: RASESVDNYGISFLN (SEQ ID NO: 9), $V_L$-CDR2: AAEYRGR (SEQ ID NO: 10), and $V_L$-CDR3: QQSRHVPYT (SEQ ID NO: 11); or $V_H$-CDR1: NTYIH (SEQ ID NO: 1), $V_H$-CDR2: RIDPAGGRTKYSPKVQG (SEQ ID NO: 12), $V_H$-CDR3: HRGGTMDY (SEQ ID NO: 13), $V_L$-CDR1: RASQSVSNYGISFLN (SEQ ID NO: 14), $V_L$-CDR2: AASYQKR (SEQ ID NO: 15), and $V_L$-CDR3: QQSSNFPWT (SEQ ID NO: 16); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRGR (SEQ ID NO: 10), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVQG (SEQ ID NO: 19), $V_H$-CDR3: HYGGTMDY (SEQ ID NO: 8), $V_L$-CDR1: RASQSVSNYGISFLN (SEQ ID NO: 14), $V_L$-CDR2: AAEYQGR (SEQ ID NO: 20), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRAR (SEQ ID NO: 21), and $V_L$-CDR3: QQSSNVPYT (SEQ ID NO: 18); or $V_H$-CDR1: NTYIH (SEQ ID NO: 1), $V_H$-CDR2: RIDPANGNTKYAPKVQG (SEQ ID NO: 22), $V_H$-CDR3: HYGSTMDY (SEQ ID NO: 23), $V_L$-CDR1: RASESVDNYGISFMN (SEQ ID NO: 24), $V_L$-CDR2: AASNQGS (SEQ ID NO: 25), and $V_L$-CDR3: QQSKEVPWT (SEQ ID NO: 26).

In one embodiment, the isolated anti-TREM-1 antibody or antigen-binding fragment thereof comprises a variable region of the heavy chain (VH) having a sequence as set forth in any one of SEQ ID NO: 27, SEQ ID NO: 28, SEQ ID NO: 29, SEQ ID NO: 30, SEQ ID NO: 31, and SEQ ID NO: 32, or a sequence having at least 80% identity with any one of SEQ ID NO: 27, SEQ ID NO: 28, SEQ ID NO: 29, SEQ ID NO: 30, SEQ ID NO: 31, and SEQ ID NO: 32.

In one embodiment, the isolated anti-TREM-1 antibody or antigen-binding fragment thereof comprises a variable region of the light chain (VL) having a sequence as set forth in any one of SEQ ID NO: 33, SEQ ID NO: 34, SEQ ID NO: 35, SEQ ID NO: 36, SEQ ID NO: 37, and SEQ ID NO: 38, or a sequence having at least 80% identity with any one of SEQ ID NO: 33, SEQ ID NO: 34, SEQ ID NO: 35, SEQ ID NO: 36, SEQ ID NO: 37, and SEQ ID NO: 38.

In one embodiment, the isolated anti-TREM-1 antibody or antigen-binding fragment thereof comprises a variable region of the heavy chain (VH) having a sequence as set forth in SEQ ID NO: 27, or a sequence having at least 80% identity with SEQ ID NO: 27, and a variable region of the light chain (VL) having a sequence as set forth in SEQ ID NO: 33, or a sequence having at least 80% identity with SEQ ID NO: 33.

In one embodiment, the isolated anti-TREM 1 antibody is a monoclonal antibody. In one embodiment, the isolated anti-TREM 1 antibody is a humanized antibody or a human antibody. In one embodiment, the isolated anti-TREM-1 antibody or antigen-binding fragment thereof is monovalent, preferably the antigen-binding fragment is a Fab, a Fv, or a scFv.

Another object of the invention is a fusion protein comprising said anti-TREM-1 antibody or antigen-binding fragment thereof.

Another object of the invention is a nucleic acid encoding said anti-TREM-1 antibody or antigen-binding fragment, or said fusion protein.

Another object of the invention is a pharmaceutical composition comprising said isolated anti-TREM-1 antibody or antigen-binding fragment thereof, or said fusion protein, and at least one pharmaceutically acceptable excipient.

Another object of the invention is said isolated anti-TREM-1 antibody or antigen-binding fragment thereof, said fusion protein, or said pharmaceutical composition, for use as a medicament.

Another object of the invention is said isolated anti-TREM-1 antibody or antigen-binding fragment thereof, said fusion protein, or said pharmaceutical composition, for use in the treatment of a disease selected from an inflammatory or autoimmune disease; a cardiovascular disease; a cancer, in particular a solid cancer; and an infectious disease, in particular a bacterial infection or a viral infection. In one embodiment, said inflammatory or autoimmune disease is selected from an inflammatory bowel disease (IBD), Crohn's disease, ulcerative colitis, irritable bowel syndrome, fibrosis, pulmonary fibrosis, liver fibrosis, non-alcoholic steatohepatitis (NASH), alcoholic hepatitis, rheumatoid arthritis, psoriasis, psoriatic arthritis, systemic lupus erythematosus, lupus nephritis, vasculitis, systemic inflammatory response syndrome (SIRS), sepsis, septic shock, type I diabetes, Grave's disease, multiple sclerosis, autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture's syndrome, chronic inflammatory demyelinating polyneuropathy, allergy, and asthma.

DETAILED DESCRIPTION

Definitions

Figure 1:
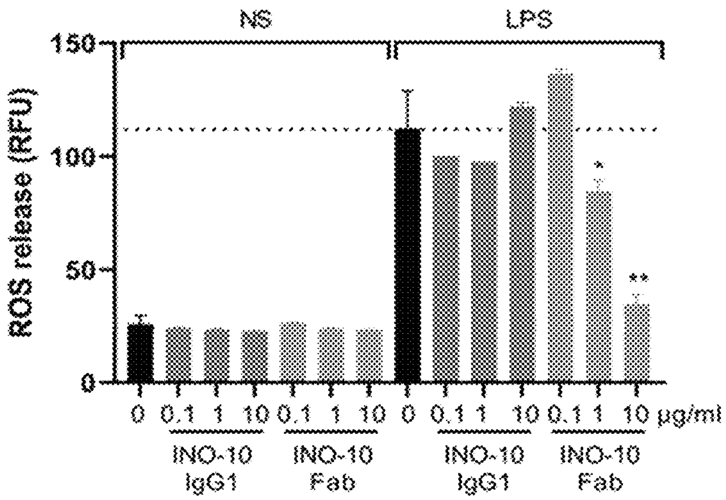
FIG. 1 is a histogram showing the effects of an anti-TREM-1 antibody (INO-10 hIgG1) or Fab (INO-10 Fab) on neutrophil intracellular reactive oxygen species (ROS) production. Human primary neutrophils were incubated for 2 h in resting conditions (NS) or stimulated with LPS (100 ng/mL) in presence or absence of INO-10 IgG1 or INO-10 Fab at the indicated concentrations. * $p<0.05$,  $p<0.01$, * $p<0.001$ versus LPS alone as determined by a parametric t-test.

In the present invention, the following terms have the following meanings:

"Ab" refers to an antibody (or to antibodies) and "mAb" refers to a monoclonal antibody (or to monoclonal antibodies).

"About", preceding a figure encompasses plus or minus 10%, or less, of the value of said figure. It is to be understood that the value to which the term "about" refers is itself also specifically, and preferably, disclosed.

"Affinity" is used to defined the strength of an antibody-antigen complex. Affinity measures the strength of interaction between an epitope and an antigen-binding site on an antibody. It may be expressed by an affinity constant KA or by a dissociation constant $K_D$.

"Antibody" and "immunoglobulin or Ig", as used herein, may be used interchangeably and refer to a protein having a combination of two heavy chains (H chains) and two light chains (L chains), whether or not it possesses any relevant specific immunoreactivity. "Antibodies" refers to such assemblies which have significant known specific immunoreactive activity to an antigen of interest (e.g., human TREM-1). The term "anti-hTREM-1 antibodies" is used herein to refer to antibodies which exhibit immunological specificity for human TREM-1 protein. As explained elsewhere herein, "specificity" for human TREM-1 (hTREM-1) does not exclude cross-reactivity with orthologs of hTREM-1, such as, for example, with simian TREM-1. As mentioned above, antibodies and immunoglobulins comprise light and heavy chains, with or without an interchain covalent linkage between them. Basic immunoglobulin structures in vertebrate systems are relatively well-understood. The generic term "immunoglobulin" comprises five distinct classes of immunoglobulins that can be distinguished biochemically: IgG, IgM, IgA, IgD, and IgE. Although the disclosure herein will generally be directed to the IgG class of immunoglobulins, all five classes are within the scope of the present invention. IgG immunoglobulins comprise two identical light chains with a molecular weight of about 23 kDa, and two identical heavy chains with a molecular weight of about 53-70 kDa. The four chains are joined by disulfide bonds in a "Y" configuration wherein the light chains bracket the heavy chains starting at the mouth of the "Y" and continuing through the variable region. The light chains of an immunoglobulin are classified as either kappa (κ) or lambda (λ). Each heavy chain class may be bonded with either a κ or λ light chain. In general, the light and heavy chains are covalently bonded to each other, and the "tail" regions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma (γ), mu (μ), alpha (α), delta (δ) or epsilon (ε) with some subclasses among them (e.g., γ1-γ4). It is the nature of this chain that determines the "class" of the antibody as IgG, IgM, IgA IgD or IgE, respectively. The immunoglobulin subclasses or "isotypes" (e.g., IgG1, IgG2, IgG3, IgG4, IgA1, etc.) are well-characterized and are known to confer functional specialization. Modified versions of each of these classes and isotypes are readily discernable to the skilled artisan in view of the instant disclosure and, accordingly, are within the scope of the present invention. As indicated herein, the variable region of an antibody allows the antibody to selectively recognize and specifically bind epitopes on antigens. That is, the light chain variable region or domain (VL) and heavy chain variable region or domain (VH) of an antibody combine to form the variable region that defines a three-dimensional antigen binding site. This quaternary antibody structure forms the antigen binding site present at the end of each arm of the "Y". More specifically, the antigen binding site is defined by three complementarity determining regions (CDRs) on each of the VH and VL.

As used herein, the term "antibody fragment", including the term "antigen-binding fragment (of the antibody)" refers to at least one portion of an intact antibody, preferably the antigen-binding region or variable region of the intact antibody, that retains the ability to specifically interact with (e.g., by binding, steric hindrance, stabilizing/destabilizing, spatial distribution) an epitope of an antigen. Examples of antibody fragments include, but are not limited to, Fab, Fab', $F(ab')_2$, Fv fragments, scFv fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, a v-NAR and a bis-scFv. Antigen binding fragments can also be grafted into scaffolds based on polypeptides such as a fibronectin type II. Papain digestion of antibodies produces two identical antigen-binding fragments, called "Fab" fragments, and a residual "Fc" fragment, a designation reflecting the ability to crystallize readily. A Fab fragment consists of an entire L chain, along with the variable region of the H chain (VH) and the first constant domain of the H chain (CH1). Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is still capable of crosslinking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

"Antigen" or "Ag" refers to a molecule that provokes an immune response. This immune response may involve either antibody production, and/or the activation of specific immunologically-competent cells, or both.

As used herein, the term "binding fragment" and, in particular, the term "antigen-binding fragment", refer to a part or region of the antibody according to the present invention, which comprises fewer amino acid residues than the whole antibody. A "binding fragment" binds antigen and/or competes with the whole antibody from which it is derived for antigen binding. Antibody binding fragments encompasses, without any limitation, single chain antibodies, Fv, Fab, Fab', Fab'-SH, F(ab)'2, Fd, defucosylated antibodies, diabodies, triabodies and tetrabodies.

"CDR" or "complementarity determining region" means the non-contiguous antigen combining sites found within the variable region of both heavy and light chain polypeptides. The precise amino acid sequence boundaries of a given CDR can be determined using any of a number of well-known schemes, including those described by Kabat et al. (1991), "Sequences of Proteins of Immunological Interest" 5th Ed. Public Health Service, National Institutes of Health, Bethesda, MD ("Kabat" numbering scheme), Al-Lazikani et al., (1997) JMB 273,927-948 ("Chothia" numbering scheme), or a combination thereof. More recently, a universal numbering system has been developed and widely adopted, ImMunoGeneTics (IMGT) Information System® (Lefranc et al., Nucleic Acids Res. 27: 209-212 1999). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain (e.g., $_{VH}$-CDR1, $_{VH}$-CDR2, $_{VH}$-CDR3, $_{VL}$-CDR1, $_{VL}$-CDR2, $_{VL}$-CDR3). As the "location" of the CDRs within the structure of the immunoglobulin variable region (or variable domain) is conserved between species and present in structures called loops, by using numbering systems that align variable region sequences according to structural features, CDR and framework residues may be readily identified. This information can be used in grafting and replacement of CDR residues from immunoglobulins of one species into an acceptor framework from, typically, a human antibody. Correspondence between the Kabat numbering and the IMGT unique numbering system is also well-known to one skilled in the art (e.g., Lefranc et al., supra).

"Epitope" refers to a specific arrangement of amino acids located on a protein or proteins to which an antibody or antigen-binding fragment thereof binds. Epitopes often consist of a chemically active surface grouping of molecules such as amino acids or sugar side chains, and have specific three-dimensional structural characteristics as well as specific charge characteristics. Epitopes can be linear (or sequential) or conformational, i.e., involving two or more sequences of amino acids in various regions of the antigen that may not necessarily be contiguous.

"Framework region" or "FR region" or "non-CDR region" includes the amino acid residues that are part of the variable region, but are not part of the CDRs (e.g., using the Kabat definition of CDRs or the IMGT® numbering definition of CDRs). Therefore, a variable region framework is between about 100-120 amino acids in length but includes only those amino acids outside of the CDRs.

For the specific example of a heavy chain variable region (VH) and for the CDRs as defined by Kabat or Chothia:

FR1 may correspond to the domain of the variable region encompassing amino acids 1-25 according to Chothia/AbM's definition, or 5 residues later according to Kabat's definition;

FR2 may correspond to the domain of the variable region encompassing amino acids 36-49;

FR3 may correspond to the domain of the variable region encompassing amino acids 67-98; and FR4 may correspond to the domain of the variable region from amino acids 104-110 to the end of the variable region.

The framework regions for the light chain are similarly separated by each of the CDRs of the light chain variable region (VL). In naturally occurring antibodies, the six CDRs present on each monomeric antibody are short, non-contiguous sequences of amino acids that are specifically positioned to form the antigen-binding site as the antibody assumes its three-dimensional configuration in an aqueous environment. As indicated above, the remainders of the heavy and light variable regions (or domains) show less inter-molecular variability in amino acid sequence and correspond to the framework regions.

The framework regions largely adopt a n-sheet conformation and the CDRs form loops which connect, and in some cases form part of, the n-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope. As indicated above, the position of CDRs can be readily identified by one of ordinary skill in the art.

"Fc domain," "Fc portion," and "Fc region" may be used interchangeably and refer to a C-terminal fragment of an antibody heavy chain, e.g., from about amino acid (aa) 230 to about aa 450 of human gamma heavy chain or its counterpart sequence in other types of antibody heavy chains (e.g., α, δ, ε and μ for human antibodies), or a naturally occurring allotype thereof.

"Fv", as used herein, refers to the minimum antibody fragment that contains a complete antigen-recognition and -binding site. This fragment consists of a dimer of one VH and one VL in tight, non-covalent association. From the folding of these two domains emanate six hypervariable loops (three loops each from the heavy and light chain) that contribute to antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Heavy chain region" includes amino acid sequences derived from the constant domains of an immunoglobulin heavy chain. A protein comprising a heavy chain region comprises at least one of a CH1 domain, a hinge region (e.g., upper, middle, and/or lower hinge domains), a CH2 domain, a CH3 domain, or a variant or fragment thereof. In certain embodiments, the antibody or antigen-binding fragment thereof according to the present invention may comprise the Fc region of an immunoglobulin heavy chain (e.g., a hinge portion, a CH2 domain, and a CH3 domain). In certain embodiments, the antibody or antigen-binding fragment thereof according to the present invention lacks at least a region of a constant domain (e.g., all or part of a CH2 domain). In certain embodiments, at least one, and preferably all, of the constant domains are derived from a human immunoglobulin heavy chain. For example, in one embodiment, the heavy chain region comprises a fully human hinge domain. In certain embodiments, the heavy chain region comprises a fully human Fc region (e.g., hinge, CH2 and CH3 domain sequences from a human immunoglobulin). In certain embodiments, the constituent constant domains of the heavy chain region are from different immunoglobulin molecules. For example, a heavy chain region of a protein may comprise a CH2 domain derived from an IgG1 molecule and a hinge region derived from an IgG3 or IgG4 molecule. In certain embodiments, the constant domains are chimeric domains comprising regions of different immunoglobulin molecules. For example, a hinge may comprise a first region from an IgG1 molecule and a second region from an IgG3 or IgG4 molecule. In certain embodiments, the constant domains of the heavy chain region may be modified such that they vary in amino acid sequence from the naturally occurring (wild-type) immunoglobulin molecule. That is, the antibody or antigen-binding fragment thereof according to the present invention may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Hinge region" includes the region of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., 1998. J Immunol. 161(8):4083-90).

"Identity" or "identical", when used in the present invention in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods.

Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., J. MoI. Biol. 215, 403-410 (1990)). The well-known Smith Waterman algorithm may also be used to determine identity.

"Monoclonal antibody" refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies or antigen-binding fragment thereof according to the present invention may be prepared by the hybridoma methodology first described by Kohler et al., 1975. Nature. 256(5517):495-7, or may be made using recombinant DNA methods in bacterial, eukaryotic animal or plant cells (U.S. Pat. No. 4,816,567). The "monoclonal antibodies" may also be isolated from phage antibody libraries using the techniques described in Clackson et al., 1991. Nature. 352(6336):624-8 and Marks et al., 1991. J Mol Biol. 222(3):581-97, for example.

"Single chain antibody", as used herein, refers to any antibody or fragment thereof that is a protein having a primary structure comprising or consisting of one uninterrupted sequence of contiguous amino acid residues, including without limitation (1) single-chain Fv molecules (scFv); (2) single chain proteins containing only one light chain variable region, or a fragment thereof that contains the three CDRs of the light chain variable region (VL), without an associated heavy chain moiety; and (3) single chain proteins containing only one heavy chain variable region (VH), or a fragment thereof containing the three CDRs of the heavy chain variable region, without an associated light chain moiety.

"Single-chain Fv", also abbreviated as "sFv" or "scFv", refers to antibody fragments that comprise a VH and a VL connected into a single amino acid chain. Preferably, the scFv amino acid sequence further comprises a peptide linker between the VH and VL that enables the scFv to form the desired structure for antigen binding.

"Subject" refers to a mammal, preferably a human. According to the present invention, a subject is a mammal, preferably a human.

"Therapeutically effective amount" or "therapeutically effective dose" refers to the amount or dose or concentration of an anti-hTREM-1 antibody or antigen-binding fragment thereof as described herein that is aimed at, without causing significant negative or adverse side effects to the subject in need of treatment, preventing, reducing, alleviating or slowing down (lessening) one or more of the symptoms or manifestations of a disease.

"Treating" or "Treatment" refers to a therapeutic treatment, to a prophylactic (or preventative) treatment, or to both a therapeutic treatment and a prophylactic (or preventative) treatment, wherein the object is to prevent, reduce, alleviate, and/or slow down (lessen) one or more of the symptoms or manifestations of a disease.

"TREM-1" refers to "triggering receptor expressed on myeloid cells-1", also sometimes known as CD354. As mentioned above, TREM-1 is a membrane-bound immunoreceptor comprising three distinct domains: an Ig-like structure (mostly responsible for ligand binding), a transmembrane part, and a short cytoplasmic tail. Unless specified otherwise, the human TREM-1 protein has an amino acid sequence as set forth in SEQ ID NO: 43, corresponding to UniProtKB/Swiss-Prot accession number Q9NP99-1, last modified on Oct. 1, 2000 and to UniProtKB accession number Q38L15-1, last modified on Nov. 22, 2005. Several transcripts are known for human TREM-1. The transcript commonly referred to as TREM1-201 (transcript ID ensembl ENST00000244709.8) encodes an amino acid sequence as set forth in SEQ ID NO: 43. The transcript commonly referred to as TREM1-202, also known as TREM-1 isoform 2 (ensembl transcript ID ENST00000334475.10) encodes an amino acid sequence as set forth in SEQ ID NO: 44 (corresponding to UniProtKB/Swiss-Prot accession number Q9NP99-2). The transcript commonly referred to as TREM1-207, also known as TREM-1 isoform 3 (ensembl transcript ID ENST00000591620.1) encodes an amino acid sequence as set forth in SEQ ID NO: 45 (corresponding to UniProtKB/Swiss-Prot accession number Q9NP99-3). The transcript commonly referred to as TREM1-204 (ensembl transcript ID ENST00000589614.5) encodes an amino acid sequence as set forth in SEQ ID NO: 46 (corresponding to UniProtKB/Swiss-Prot accession number K7EKM5-1, last modified Jan. 9, 2013).

"hTREM-1" refers to the human TREM-1.

"Variable" refers to the fact that certain regions of the VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL and the VH which form part of the antigen-binding site. The 6 hypervariable loops may each comprise part of a "complementarity determining region" or "CDR", as defined hereinabove.

"VH" refers to the variable region (or domain) of the heavy chain of an antibody.

"VL" refers to the variable region (or domain) of the light chain of an antibody.

The present invention relates to an isolated antibody, or antigen-binding fragment thereof, which binds to human Triggering Receptor Expressed on Myeloid cells-1 (human TREM-1 or hTREM-1). The present invention thus relates to an isolated anti-human TREM-1 (or anti-hTREM-1) antibody or antigen-binding fragment thereof.

According to one embodiment, the isolated antibody, or antigen-binding fragment thereof, specifically binds to hTREM-1. In other words, according to one embodiment, the isolated antibody, or antigen-binding fragment thereof, is specific for hTREM-1.

An antibody or antigen-binding fragment thereof is said to be "specific for", "immunospecific" or to "specifically bind" an antigen if it reacts at a detectable level with said antigen (e.g., TREM-1, in particular hTREM-1), preferably with an affinity constant ($k_a$) of greater than or equal to about $10^3$ $M^{-1}$, preferably greater than or equal to about $5\times10^3$ $M^{-1}$, $10^4$ $M^{-1}$, $5\times10^4$ $M^{-1}$, or $10^5$ $M^{-1}$. Affinity of an antibody or antigen-binding fragment thereof for its cognate antigen is also commonly expressed as an equilibrium dissociation constant ($K_D$). Thus, an antibody or antigen-binding fragment thereof is said to be "immunospecific", "specific for" or to "specifically bind" an antigen if it reacts at a detectable level with said antigen (e.g., TREM-1, in particular hTREM-1), preferably with a $K_D$ of less than or equal to $10^{-6}$ M, preferably less than or equal to $10^{-7}$ M, $5\times10^{-8}$ M, $10^{-8}$ M, $5\times10^{-9}$ M, $10^{-9}$ M, or $5\times10^{-10}$ M, or less.

Affinities of antibodies or antigen-binding fragments thereof can be readily determined using conventional techniques, for example, those described by Scatchard, 1949. *Ann NY Acad Sci.* 51:660-672. Binding properties of an antibody or antigen-binding fragment thereof to antigens, cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, e.g., using BIAcore®).

In one embodiment, the isolated anti-hTREM-1 antibody, or antigen-binding fragment thereof, presents a $K_D$ for binding to hTREM-1 inferior or equal to about $10\times10^{-9}$ M, preferably inferior or equal to about $9\times10^{-9}$ M, $8\times10^{-9}$ M, $7\times10^{-9}$ M, $6\times10^{-9}$ M, $5\times10^{-9}$ M, $4\times10^{-9}$ M, $3\times10^{-9}$ M, $2\times10^{-9}$ M, or $10^{-9}$ M. In one embodiment, the isolated anti-hTREM-1 antibody, or antigen-binding fragment thereof, presents a $K_D$ for binding to hTREM-1 inferior or equal to about $10^{-9}$ M, preferably inferior or equal to about $9\times10^{-10}$ M, $8\times10^{-10}$ M, $7\times10^{-10}$ M, $6\times10^{-10}$ M, or $5\times10^{-10}$ M. In one embodiment, the $K_D$ of the isolated anti-hTREM-1 antibody, or antigen-binding fragment thereof, for binding to hTREM-1 ranges from about $1\cdot10^{-10}$ M to about $10\cdot10^{-9}$ M, preferably from about $3\cdot10^{-10}$ M to about $8\cdot10^{-9}$ M.

According to one embodiment, the isolated antibody, or antigen-binding fragment thereof, binds human TREM-1 having an amino acid sequence as set forth in at least one of:

- SEQ ID NO: 43, corresponding to UniProtKB/Swiss-Prot accession number Q9NP99-1, last modified on Oct. 1, 2000 and to UniProtKB accession number Q38L15-1, last modified on Nov. 22, 2005; and also corresponding to the amino acid sequence encoded by the transcript commonly referred to as TREM1-201 (transcript ID ensembl ENST00000244709.8);
- SEQ ID NO: 44, corresponding to UniProtKB/Swiss-Prot accession number Q9NP99-2; and also corresponding to the amino acid sequence encoded by the transcript commonly referred to as TREM1-202, also known as TREM-1 isoform 2 (ensembl transcript ID ENST00000334475.10);
- SEQ ID NO: 45, corresponding to UniProtKB/Swiss-Prot accession number Q9NP99-3; and also corresponding to the amino acid sequence encoded by the transcript commonly referred to as TREM1-207, also known as TREM-1 isoform 3 (ensembl transcript ID ENST00000591620.1); or
- SEQ ID NO: 46 corresponding to UniProtKB/Swiss-Prot accession number K7EKM5-1, last modified Jan. 9, 2013; and also corresponding to the transcript commonly referred to as TREM1-204 (ensembl transcript ID ENST00000589614.5).

In one embodiment, the isolated antibody, or antigen-binding fragment thereof, binds hTREM-1 having an amino acid sequence as set forth in SEQ ID NO: 43, hTREM-1 having an amino acid sequence as set forth in SEQ ID NO: 44, hTREM-1 having an amino acid sequence as set forth in SEQ ID NO: 45, and/or hTREM-1 having an amino acid sequence as set forth in SEQ ID NO: 46. In one embodiment, the isolated antibody, or antigen-binding fragment thereof, binds hTREM-1 having an amino acid sequence as set forth in SEQ ID NO: 43.

According to an embodiment, the isolated anti-hTREM-1 antibody, or antigen-binding fragment thereof, is able to inhibit hTREM-1.

As used herein, "able to inhibit hTREM-1" means that the isolated anti-hTREM-1 antibody, or antigen-binding fragment thereof, is able to inhibit the function and/or activity of TREM-1, in particular hTREM-1. Thus, in one embodiment, the isolated anti-hTREM-1 antibody, or antigen-binding fragment thereof, is able to inhibit the activation of the TREM-1 signaling pathway. In one embodiment, the isolated anti-hTREM-1 antibody, or antigen-binding fragment thereof, is able to inhibit the clustering of TREM-1. In one embodiment, the isolated anti-hTREM-1 antibody, or antigen-binding fragment thereof, is able to inhibit the dimerization of TREM-1. In one embodiment, the isolated anti-hTREM-1 antibody, or antigen-binding fragment thereof, is able to inhibit ligand binding on TREM-1.

In one embodiment, the isolated anti-hTREM-1 antibody, or antigen-binding fragment thereof, is able to inhibit the function and/or activity of TREM-1, in particular hTREM-1, regardless of the stimulation signal with which TREM-1 has been activated. In one embodiment, the isolated anti-hTREM-1 antibody, or antigen-binding fragment thereof, is able to inhibit the function and/or activity of TREM-1, in particular hTREM-1, which has been activated in a ligand-dependent manner (e.g., with PGLYRP1) and/or in a ligand-independent manner (e.g., via TLRs). Stimulation methods for activating TREM-1, in particular hTREM-1, are well-known in the art and include, for example, direct activation through the incubation of cells expressing TREM-1 (such as, for example neutrophils) with a TREM-1 ligand complex (e.g., PGLYRP1 (peptidoglycan recognition protein 1) complexed with peptidoglycan); and indirect activation through the activation of Toll-like receptors (TLRs) (such as TLR2 and/or TLR4) by incubation of cells expressing TREM-1 (such as, for example neutrophils) with peptidoglycan (PGN), lipopolysaccharides (LPS), or heat-killed or heat-inactivated bacteria (such as, for example, heat-killed *Escherichia coli* or heat-killed *Bacillus subtilis*). Thus, in one embodiment, the isolated anti-hTREM-1 antibody, or antigen-binding fragment thereof, is able to inhibit the function and/or activity of TREM-1, in particular hTREM-1, after activation of TREM-1 either with a TREM-1 ligand complex (e.g., PGLYRP1 complexed with PGN), with PGN stimulation, with LPS stimulation, or with heat-killed or heat-inactivated bacteria (such as, for example, heat-killed *Escherichia coli* or heat-killed *Bacillus subtilis*).

Methods for assessing TREM-1 inhibition are well-known in the art and comprise, for example the assays described hereinafter in the example section.

Assays for evaluating TREM-1 inhibition include the in vitro evaluation of reactive oxygen species (ROS) production by neutrophils stimulated so as to activate the TREM-1 signaling pathway, for example through incubation in presence of lipopolysaccharides (LPS), or in presence of peptidoglycan (PGN) alone, or in presence of PGLYRP1 (peptidoglycan recognition protein 1) complexed with peptidoglycan (so-called PPx or PP complex), or in presence of heat-killed or heat-inactivated bacteria such as *Escherichia coli* or *Bacillus subtilis*. In one embodiment, a compound able to bind TREM-1 and inhibit the ROS production by LPS-stimulated neutrophils, PGN-stimulated neutrophils, PP-stimulated neutrophils, or heat-killed or heat-inactivated bacteria-stimulated neutrophils is thus able to inhibit TREM-1.

Assays for evaluating TREM-1 inhibition also include the in vitro evaluation of the expression and/or secretion of pro-inflammatory cytokines/chemokines (such as cytokines chemokine ligand 2 (CCL2) also known as monocyte chemoattractant protein 1 (MCP1), interleukin-1β (IL-1β), interleukin-6 (IL-6), interleukin-8 (IL-8), interferon gamma-induced protein 10 (IP-10) also known as C-X-C motif chemokine ligand 10 (CXCL10), and tumor necrosis factor alpha (TNF-α or TNFa)) by primate or human or hTREM-1 Knock In mouse primary cells (e.g., human or cynomolgus or hTREM-1 Knock In mouse neutrophils, monocytes, or whole blood samples) stimulated so as to activate the TREM-1 signaling pathway, for example through incubation in presence of LPS, or in presence of PGN alone, or in presence of PP complex, or in presence of heat-killed or heat-inactivated bacteria such as *Escherichia coli* or *Bacillus subtilis*. In one embodiment, a compound able to bind TREM-1 and inhibit the pro-inflammatory cytokine/chemokine expression and/or secretion by LPS-stimulated, PGN-stimulated, PP-stimulated, or heat-killed or heat-inactivated bacteria-stimulated neutrophils or whole blood is thus able to inhibit TREM-1.

Assays for evaluating TREM-1 inhibition also include the in vitro evaluation of the expression and/or secretion of pro-inflammatory cytokines/chemokines (such as CCL2 also known MCP1, IL-1β, IL-6, IL-8, IP-10 also known as CXCL10, and TNF-α or TNFa) by a human monocytic cell line (e.g., THP-1 cell line) or a human myelomonocytic cell line (e.g., U937 cell line) stimulated so as to activate the TREM-1 signaling pathway, for example through incubation in presence of LPS, or in presence of PGN alone, or in presence of PP complex, or in presence of heat-killed or heat-inactivated bacteria such as *Escherichia coli* or *Bacillus subtilis*. In one embodiment, a compound able to bind TREM-1 and inhibit the pro-inflammatory cytokine/chemokine expression and/or secretion by a LPS-stimulated, PGN-stimulated, PP-stimulated, or heat-killed or heat-inactivated bacteria-stimulated human monocytic cell line or human myelomonocytic cell line is thus able to inhibit TREM-1.

Assays for evaluating TREM-1 inhibition also include the in vivo evaluation of the expression and/or secretion of pro-inflammatory cytokines/chemokines (such as CCL2 also known MCP1, IL-1β, IL-6, IL-8, IP-10 also known as CXCL10, and TNF-α or TNFa) in mice models. Examples of relevant mice models include transgenic BRGSF mice in which endotoxemia was induced by LPS, hTREM-1 Knock In mice in which endotoxemia was induced by LPS, hTREM-1 Knock In mice in which a systemic inflammatory response was induced by PGN, and hTREM-1 Knock In mice treated with LPS or PGN for example to induce a local inflammatory response. In one embodiment, a compound able to bind TREM-1 and inhibit the pro-inflammatory cytokine/chemokine expression and/or secretion in a mice model as described above is thus able to inhibit TREM-1.

In one embodiment, the anti-hTREM-1 antibody, or antigen-binding fragment thereof, as described herein is an isolated antibody, or antigen-binding fragment thereof.

As used herein, "isolated", as in "isolated antibody or antigen-binding fragment thereof", is intended to refer to an antibody, or antigen-binding fragment thereof, that is substantially free of other proteins or antibodies having different antigenic specificities (e.g., an isolated antibody, or antigen-binding fragment thereof, that specifically binds hTREM-1 and is substantially free of proteins or antibodies that specifically bind antigens other than hTREM-1). An isolated antibody, or antigen-binding fragment thereof, that specifically binds hTREM-1 may, however, have cross-reactivity to other related antigens, such as TREM-1 molecules from other genera or species. Moreover, an isolated antibody, or antigen-binding fragment thereof, may be substantially free of other cellular material and/or chemicals, in particular those that would interfere with therapeutic uses of the antibody, or antigen-binding fragment thereof, including without limitation, enzymes, hormones, and other proteinaceous or non-proteinaceous components.

In one embodiment, the isolated antibody, or antigen-binding fragment thereof, is purified.

In one embodiment, the isolated antibody, or antigen-binding fragment thereof, is purified to obtain a purity greater than 80%, 85%, 90%, 91%, 92%, 93%, 94%, 95%, 96%, 98%, or 99% by weight of antibody or antigen-binding fragment, preferably greater than 90%, 96%, 97%, 98% or 99% by weight. In one embodiment, the purity is determined by analytical size exclusion chromatography (SEC).

In one embodiment, the isolated antibody, or antigen-binding fragment thereof, is purified to obtain an endotoxin level under 0.5, 0.4, 0.3, 0.2, or 0.1 EU/mg of protein, preferably under 0.1 EU/mg of protein.

In one embodiment, as indicated above, the isolated antibody, or antigen-binding fragment thereof, binds hTREM-1 and at least one ortholog of hTREM-1. Thus, in one embodiment, the isolated antibody, or antigen-binding fragment thereof, binds hTREM-1 and at least one TREM-1 from another genus or species. In other words, in one embodiment, the isolated antibody, or antigen-binding fragment thereof, displays cross-reactivity (cross-reacts) to other related antigens. In one embodiment, the isolated antibody, or antigen-binding fragment thereof, binds hTREM-1 and monkey TREM-1 (in particular cynomolgus monkey TREM-1 or in short cynomolgus TREM-1).

In one embodiment, the isolated anti-hTREM-1 antibody or antigen-binding fragment thereof is a molecule selected from the group comprising or consisting of a whole antibody, a humanized antibody, a single chain antibody, a dimeric single chain antibody, a Fv, a scFv, a Fab, a Fab', a Fab'-SH, a F(ab)'2, a Fc silent antibody or antigen-binding fragment (i.e., an antibody or antigen-binding fragment comprising a Fc silent), an antibody or antigen-binding fragment with an engineered Fc such as a defucosylated Fc (defucosylated antibody), a bispecific antibody, a diabody, a triabody, and a tetrabody.

Antigen-binding fragments of antibodies can be obtained using standard methods. For instance, Fab or $F(ab')_2$ fragments may be produced by protease digestion of the isolated antibodies, according to conventional techniques. Alternatively, antigen-binding fragments of antibodies, such as Fab fragments, may be expressed as recombinant proteins.

In one embodiment, the isolated antibody, or antigen-binding fragment thereof, is monoclonal. In another embodiment, the isolated antibody, or antigen-binding fragment thereof, is polyclonal.

In one embodiment, the isolated antibody, or antigen-binding fragment thereof, is monovalent. In another embodiment, the isolated antibody, or antigen-binding fragment thereof, is divalent.

Examples of monovalent antigen-binding antibody fragments include Fab fragments, scFv fragments, Fv fragments. In one embodiment, the antigen-binding antibody fragment is thus a molecule selected from the group comprising or consisting of a Fab, a Fv, and a scFv. In one embodiment, the isolated antibody, or antigen-binding fragment thereof, is a Fab.

In one embodiment, the anti-hTREM-1 antibody, or antigen-binding fragment thereof, comprises a fully human or substantially human heavy chain constant region (abbreviated herein as $C_H$) and/or light chain constant region (abbreviated herein as $C_L$). In one embodiment, the constant region is of human origin.

The term "substantially human", in the context of the constant region of a humanized or chimeric antibody or antigen-binding fragment thereof, refers to a constant region having an amino acid sequence having of at least 70% identity, preferably at least 75%, 80%, 85%, 90%, 95%, 96%, 97%, 98%, 99% or more of identity with the amino acid sequence of a human constant region.

In one embodiment, the anti-hTREM-1 antibody, or antigen-binding fragment thereof, comprises a fully or substantially fully murine $C_H$ and/or $C_L$. In one embodiment, the constant region is of murine origin.

In one embodiment, the anti-hTREM-1 antibody, or antigen-binding fragment thereof, is a murine antibody or antigen-binding fragment thereof.

In one embodiment, the anti-hTREM-1 antibody, or antigen-binding fragment thereof, is a chimeric antibody or antigen-binding fragment thereof.

A "chimeric antibody", as used herein, refers to an antibody or antigen-binding fragment thereof comprising a first amino acid sequence linked to a second amino acid sequence with which it is not naturally linked in nature. The amino acid sequences may normally exist in separate proteins that are brought together in the chimeric (or fusion) protein or may normally exist in the same protein but are placed in a new arrangement in the chimeric (or fusion) protein. A chimeric protein may be created, for example, by chemical synthesis, or by creating and translating a polynucleotide in which the peptide regions are encoded in the desired relationship. The term "chimeric antibody" encompasses herein antibodies and antigen-binding fragment thereof in which:

(a) the constant region, or a portion thereof, is altered, replaced or exchanged so that the variable region is linked to a constant region of a different or altered class, effector function and/or species, or an entirely different molecule which confers new properties to the chimeric antibody, e.g., an enzyme, protein, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

In one embodiment, the antibody or antigen-binding fragment thereof according to the present invention is a deimmunized antibody or antigen-binding fragment thereof.

Deimmunization aims at reducing the immunogenicity of the antibody or antigen-binding fragment thereof without hindering their ability to bind and inhibit hTREM-1 as described herein. Methods for deimmunizing antibodies, or antigen-binding fragments thereof, are well-known in the art. Such methods notably comprise substituting key amino acids within human T cell epitope sequences present in the amino acid sequence of the antibodies, or antigen-binding fragments thereof, thus preventing the binding of the antibodies, or antigen-binding fragments thereof, to HLA (human leukocyte antigen) and the subsequent triggering of a T cell response.

In one embodiment, the antibody or antigen-binding fragment thereof according to the present invention is a humanized antibody or antigen-binding fragment thereof.

A "humanized antibody", as used herein, refers to a chimeric antibody or antigen-binding fragment thereof which contains minimal sequence derived from a non-human immunoglobulin. It includes antibodies made by a non-human cell having variable and constant regions which have been altered to more closely resemble antibodies that would be made by a human cell, e.g., by altering the non-human antibody amino acid sequence to incorporate amino acids found in human germline immunoglobulin sequences. Humanized antibodies or antigen-binding fragments thereof according to the present invention may include amino acid residues not encoded by human germline immunoglobulin sequences (e.g., mutations introduced by random or site-specific mutagenesis in vitro or by somatic mutation in vivo), for example in the CDRs. The term "humanized antibody" also includes antibodies and antigen-binding fragments thereof in which CDR sequences derived from the germline of another mammalian species, such as a mouse, have been grafted onto human framework sequences. In other words, the term "humanized antibody" may refer to an antibody or antigen-binding fragment thereof in which the CDRs of a recipient human antibody are replaced by CDRs from a donor non-human antibody. Humanized antibodies or antigen-binding fragments thereof may also comprise residues of donor origin in the framework sequences. The humanized antibody or antigen-binding fragment thereof can also comprise at least a portion of a human immunoglobulin constant region. Humanized antibodies or antigen-binding fragments thereof may also comprise residues which are found neither in the recipient antibody nor in the imported CDR or framework sequences.

A "humanized antibody" may retain a similar antigenic specificity as the original antibody or donor antibody (such as a donor non-human antibody). However, using certain methods of humanization, the affinity and/or specificity of binding of the antibody may be increased.

Methods for humanizing the antibody or antigen-binding fragment thereof according to the present invention are well-known in the art. For example, humanized antibodies and antigen-binding fragments thereof may be produced according to various techniques, such as by using, for immunization, transgenic animals that have been engineered to express a human antibody repertoire (Jakobovitz et al., 1993. *Nature*. 362(6417):255-8), or by selection of antibody repertoires using phage display methods. Such techniques are known to the skilled person and can be implemented starting from monoclonal antibodies or antigen-binding fragments thereof as disclosed in the present application.

In one embodiment, the anti-hTREM-1 antibody, or antigen-binding fragment thereof, is from the IgG class.

In one embodiment, the anti-hTREM-1 antibody, or antigen-binding fragment thereof, is from the human IgG1 subclass. In one embodiment, the anti-hTREM-1 antibody, or antigen-binding fragment thereof, is thus an IgG1 antibody, preferably a human IgG1 antibody or a chimeric human IgG1 antibody. In one embodiment, the anti-hTREM-1 antibody, or antigen-binding fragment thereof, is from the human IgG4 subclass. In one embodiment, the anti-hTREM-1 antibody, or antigen-binding fragment thereof, is thus an IgG4 antibody, preferably a human IgG4 antibody or a chimeric human IgG4 antibody. In one embodiment, the anti-hTREM-1 antibody, or antigen-binding fragment thereof, is from the human IgG2 subclass. In one embodiment, the anti-hTREM-1 antibody, or antigen-binding fragment thereof, is thus an IgG2 antibody, preferably a human IgG2 antibody or a chimeric human IgG2 antibody. In one embodiment, the anti-hTREM-1 antibody, or antigen-binding fragment thereof, is from the human IgG3 subclass. In one embodiment, the anti-hTREM-1 antibody, or antigen-binding fragment thereof, is thus an IgG3 antibody, preferably a human IgG3 antibody or a chimeric human IgG3 antibody.

As used herein, the phrase "characterized as having [ . . . ] amino acids being substituted by a different amino acid" in reference to a given sequence, refers to the occurrence, in said sequence, of conservative amino acid modifications.

As used herein, the expression "conservative amino acid modifications" refers to modifications that do not significantly affect or alter the binding characteristics of the antibody or antigen-binding fragment thereof containing the amino acid sequence. Such conservative modifications include amino acid substitutions, additions and deletions.

Modifications can be introduced into an antibody or antigen-binding fragment thereof by standard techniques known in the art, such as site-directed mutagenesis and PCR-mediated mutagenesis.

Conservative amino acid substitutions are typically those in which an amino acid residue is replaced with an amino acid residue having a side chain with similar physicochemical properties. Specified variable regions and CDR sequences may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid insertions, deletions and/or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), P-branched side chains (e.g., threonine, valine, isoleucine) and aromatic side chains (e.g., tyrosine, phenylalanine, tryptophan, histidine). Thus, one or more amino acid residues within the CDRs and/or variable regions of the antibody or antigen-binding fragment thereof according to the present invention can be replaced with other amino acid residues from the same side chain family and the altered antibody can be tested for retained function (i.e., the properties set forth herein, such as, e.g., the binding to hTREM-1) using the assays described herein. In one embodiment, a string of amino acids within the CDRs and/or variable regions of the antibody or antigen-binding fragment thereof according to the present invention can be replaced with a structurally similar string that differs in order and/or composition of side chain family members.

In the present invention, unless otherwise specified, the position of the complementary-determining regions (CDRs) is determined using the Kabat nomenclature.

According to one embodiment, the anti-hTREM-1 antibody, or antigen-binding fragment thereof, comprises a variable region of the heavy chain (also referred to as heavy chain variable region or VH) which comprises at least one, preferably at least two, more preferably the three following complementary-determining regions (CDRs):

$V_H$-CDR1: NTYIH (SEQ ID NO: 1);

$V_H$-CDR2: RIDPA$X_1$G$X_2$TKY$X_3$PKV$X_4$G (SEQ ID NO: 2), wherein $X_1$ is N or G, $X_2$ is N or R, $X_3$ is A, D, or S, $X_4$ is Q or K; or RIDPA$X_1$G$X_2$TKY$X_3$PKF$X^4$G (SEQ ID NO: 39), wherein $X_1$ is N or G, $X_2$ is N or R, $X_3$ is A, D, or S, $X_4$ is Q or K; and/or $V_H$-CDR3: H$X_5$G$X_6$TMDY (SEQ ID NO: 3), wherein $X_5$ is Y or R, $X_6$ is S or G.

In one embodiment, the anti-hTREM-1 antibody, or antigen-binding fragment thereof, comprises a VH which comprises at least one, preferably at least two, more preferably the three following CDRs:

$V_H$-CDR1: NTYIH (SEQ ID NO: 1);

$V_H$-CDR2: RIDPA$X_1$G$X_2$TKY$X_3$PKV$X_4$G (SEQ ID NO: 2), wherein $X_1$ is N or G, $X_2$ is N or R, $X_3$ is A, D, or S, $X_4$ is Q or K; and/or $V_H$-CDR3: H$X_5$G$X_6$TMDY (SEQ ID NO: 3), wherein $X_5$ is Y or R, $X_6$ is S or G.

In one embodiment, the anti-hTREM-1 antibody, or antigen-binding fragment thereof, comprises a VH which comprises at least one, preferably at least two, more preferably the three following CDRs:

$V_H$-CDR1: NTYIH (SEQ ID NO: 1);

$V_H$-CDR2: RIDPA$X_1$G$X_2$TKY$X_3$PKF$X_4$G (SEQ ID NO: 39), wherein $X_1$ is N or G, $X_2$ is N or R, $X_3$ is A, D, or S, $X_4$ is Q or K; and/or $V_H$-CDR3: H$X_5$G$X_6$TMDY (SEQ ID NO: 3), wherein $X_5$ is Y or R, $X_6$ is S or G.

According to one embodiment, the anti-hTREM-1 antibody, or antigen-binding fragment thereof, comprises a VH which comprises the three following CDRs:

$V_H$-CDR1: NTYIH (SEQ ID NO: 1);

$V_H$-CDR2: RIDPA$X_1$G$X_2$TKY$X_3$PKV$X_4$G (SEQ ID NO: 2), wherein $X_1$ is N or G, $X_2$ is N or R, $X_3$ is A, D, or S, $X_4$ is Q or K; or RIDPA$X_1$G$X_2$TKY$X_3$PKF$X_4$G (SEQ ID NO: 39), wherein $X_1$ is N or G, $X_2$ is N or R, $X_3$ is A, D, or S, $X_4$ is Q or K; and $V_H$-CDR3: H$X_5$G$X_6$TMDY (SEQ ID NO: 3), wherein $X_5$ is Y or R, $X_6$ is S or G.

In one embodiment, the anti-hTREM-1 antibody, or antigen-binding fragment thereof, comprises a VH which comprises the three following CDRs:

$V_H$-CDR1: NTYIH (SEQ ID NO: 1);

$V_H$-CDR2: RIDPA$X_1$G$X_2$TKY$X_3$PKV$X_4$G (SEQ ID NO: 2), wherein $X_1$ is N or G, $X_2$ is N or R, $X_3$ is A, D, or S, $X_4$ is Q or K; and $V_H$-CDR3: H$X_5$G$X_6$TMDY (SEQ ID NO: 3), wherein $X_5$ is Y or R, $X_6$ is S or G.

In one embodiment, the anti-hTREM-1 antibody, or antigen-binding fragment thereof, comprises a VH which comprises the three following CDRs:

$V_H$-CDR1: NTYIH (SEQ ID NO: 1);

RIDPA$X_1$G$X_2$TKY$X_3$PKF$X_4$G (SEQ ID NO: 39), wherein $X_1$ is N or G, $X_2$ is N or R, $X_3$ is A, D, or S, $X_4$ is Q or K; and $V_H$-CDR3: H$X_5$G$X_6$TMDY (SEQ ID NO: 3), wherein $X_5$ is Y or R, $X_6$ is S or G.

Examples of $V_H$-CDR2 having a sequence as set forth in SEQ ID NO: 2 as described hereinabove include, without being limited to, RIDPAGGRTKYDPKVKG (SEQ ID NO: 7), RIDPAGGRTKYSPKVQG (SEQ ID NO: 12), RIDPAGGRTKYAPKVKG (SEQ ID NO: 17), RIDPAGGRTKYAPKVQG (SEQ ID NO: 19), and RIDPANGNTKYAPKVQG (SEQ ID NO: 22). Thus, in one embodiment, the $V_H$-CDR2 having a sequence as set forth in SEQ ID NO: 2 as described hereinabove is selected from the group comprising or consisting of RIDPAGGRTKYDPKVKG (SEQ ID NO: 7), RIDPAGGRTKYSPKVQG (SEQ ID NO:12), RIDPAGGRTKYAPKVKG (SEQ ID NO: 17), RIDPAGGRTKYAPKVQG (SEQ ID NO: 19), and RIDPANGNTKYAPKVQG (SEQ ID NO: 22).

Examples of $V_H$-CDR2 having a sequence as set forth in SEQ ID NO: 39 as described hereinabove include, without being limited to, RIDPANGNTKYAPKFQG (SEQ ID NO: 40). Thus, in one embodiment, the $V_H$-CDR2 having a sequence as set forth in SEQ ID NO: 39 as described hereinabove is RIDPANGNTKYAPKFQG (SEQ ID NO: 40).

Examples of $V_H$-CDR3 having a sequence as set forth in SEQ ID NO: 3 as described hereinabove include, without being limited to, HYGGTMDY (SEQ ID NO: 8), HRGGTMDY (SEQ ID NO: 13), and HYGSTMDY (SEQ ID NO: 23). Thus, in one embodiment, the $V_H$-CDR3 having a sequence as set forth in SEQ ID NO: 3 as described hereinabove is selected from the group comprising or consisting of HYGGTMDY (SEQ ID NO: 8), HRGGTMDY (SEQ ID NO: 13), and HYGSTMDY (SEQ ID NO: 23).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPAGGRTKYDPKVKG (SEQ ID NO: 7); and/or $V_H$-CDR3: HYGGTMDY (SEQ ID NO: 8).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPAGGRTKYSPKVQG (SEQ ID NO: 12); and/or $V_H$-CDR3: HRGGTMDY (SEQ ID NO: 13).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPAGGRTKYAPKVKG (SEQ ID NO: 17); and/or $V_H$-CDR3: HRGGTMDY (SEQ ID NO: 13).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPAGGRTKYAPKVQG (SEQ ID NO: 19); and/or $V_H$-CDR3: HYGGTMDY (SEQ ID NO: 8).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPANGNTKYAPKVQG (SEQ ID NO: 22); and/or $V_H$-CDR3: HYGSTMDY (SEQ ID NO: 23).

In one embodiment, the anti-hTREM-1 antibody, or antigen-binding fragment thereof, comprises a VH which comprises at least one (e.g., 1, 2 or 3) of the following CDR, and preferably the three following CDRs $V_H$-CDR1: NTYIH (SEQ ID NO: 1);

$V_H$-CDR2: RIDPANGNTKYAPKFQG (SEQ ID NO: 40); and/or $V_H$-CDR3: HYGSTMDY (SEQ ID NO: 23).

In one embodiment, any of $V_H$-CDR1, $V_H$-CDR2 and/or $V_H$-CDR3 having an amino acid sequence as set forth in any one of SEQ ID NOs 1-3, 7, 8, 12, 13, 17, 19, 22, 23, 39 and 40 as described hereinabove can be characterized as having 1, 2, 3 or more amino acid(s) being substituted by a different amino acid. In one embodiment, any of $V_H$-CDR1, $V_H$-CDR2 and/or $V_H$-CDR3 with SEQ ID NOs 1-3, 7, 8, 12, 13, 17, 19, 22, 23, 39 and 40 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2 and/or $V_H$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in any one of SEQ ID NOs 1-3, 7, 8, 12, 13, 17, 19, 22, 23, 39 and 40.

According to one embodiment, the anti-hTREM-1 antibody, or antigen-binding fragment thereof, comprises a variable region of the light chain (also referred to as light chain variable region or VL) which comprises at least one, preferably at least two, more preferably the three following complementary-determining regions (CDRs):

$V_L$-CDR1: RASX$_7$SVX$_8$NYGISFX$_9$N (SEQ ID NO: 4), wherein $X_7$ is E or Q, $X_8$ is D or S, $X_9$ is M or L;

$V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and/or $V_L$-CDR3: QQSX$_{15}$X$_{16}$X$_{17}$PX$_{18}$T (SEQ ID NO: 6), wherein $X_{15}$ is K, R, or S, $X_{16}$ is E, H, or N, $X_{17}$ is V or F, $X_{18}$ is W or Y.

According to one embodiment, the anti-hTREM-1 antibody, or antigen-binding fragment thereof, comprises a VL which comprises the three following CDRs:

$V_L$-CDR1: RASX$_7$SVX$_8$NYGISFX$_9$N (SEQ ID NO: 4), wherein $X_7$ is E or Q, $X_8$ is D or S, $X_9$ is M or L;

$V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and $V_L$-CDR3: QQSX$_{15}$X$_{16}$X$_{17}$PX$_{18}$T (SEQ ID NO: 6), wherein $X_{15}$ is K, R, or S, $X_{16}$ is E, H, or N, $X_{17}$ is V or F, $X_{18}$ is W or Y.

Examples of $V_L$-CDR1 having a sequence as set forth in SEQ ID NO: 4 as described hereinabove include, without being limited to, RASESVDNYGISFLN (SEQ ID NO: 9), RASQSVSNYGISFLN (SEQ ID NO: 14), and RASESVDNYGISFMN (SEQ ID NO: 24). Thus, in one embodiment, the $V_L$-CDR1 having a sequence as set forth in SEQ ID NO: 4 as described hereinabove is selected from the group comprising or consisting of RASESVDNYGISFLN (SEQ ID NO: 9), RASQSVSNYGISFLN (SEQ ID NO: 14), and RASESVDNYGISFMN (SEQ ID NO: 24).

Examples of $V_L$-CDR2 having a sequence as set forth in SEQ ID NO: 5 as described hereinabove include, without being limited to, AAEYRGR (SEQ ID NO: 10), AASYQKR (SEQ ID NO: 15), AAEYQGR (SEQ ID NO: 20), AAEYRAR (SEQ ID NO: 21), and AASNQGS (SEQ ID NO: 25). Thus, in one embodiment, the $V_L$-CDR2 having a sequence as set forth in SEQ ID NO: 5 as described hereinabove is selected from the group comprising or consisting of AAEYRGR (SEQ ID NO: 10), AASYQKR (SEQ ID NO: 15), AAEYQGR (SEQ ID NO: 20), AAEYRAR (SEQ ID NO: 21), and AASNQGS (SEQ ID NO: 25).

Examples of $V_L$-CDR3 having a sequence as set forth in SEQ ID NO: 6 as described hereinabove include, without being limited to, QQSRHVPYT (SEQ ID NO: 11), QQSSNFPWT (SEQ ID NO: 16), QQSSNVPYT (SEQ ID NO: 18), and QQSKEVPWT (SEQ ID NO: 26). Thus, in one embodiment, the $V_L$-CDR3 having a sequence as set forth in SEQ ID NO: 6 as described hereinabove is selected from the group comprising or consisting of QQSRHVPYT (SEQ ID NO: 11), QQSSNFPWT (SEQ ID NO: 16), QQSSNVPYT (SEQ ID NO: 18), and QQSKEVPWT (SEQ ID NO: 26).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASESVDNYGISFLN (SEQ ID NO: 9);

$V_L$-CDR2: AAEYRGR (SEQ ID NO: 10); and/or $V_L$-CDR3: QQSRHVPYT (SEQ ID NO: 11).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASQSVSNYGISFLN (SEQ ID NO: 14);
$V_L$-CDR2: AASYQKR (SEQ ID NO: 15) and/or
$V_L$-CDR3: QQSSNFPWT (SEQ ID NO: 16).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASQSVSNYGISFLN (SEQ ID NO: 14);
$V_L$-CDR2: AAEYRGR (SEQ ID NO: 10); and/or
$V_L$-CDR3: QQSSNVPYT (SEQ ID NO: 18).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASQSVSNYGISFLN (SEQ ID NO: 14);
$V_L$-CDR2: AAEYQGR (SEQ ID NO: 20); and/or
$V_L$-CDR3: QQSSNVPYT (SEQ ID NO: 18).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASQSVSNYGISFLN (SEQ ID NO: 14);
$V_L$-CDR2: AAEYRAR (SEQ ID NO: 21); and/or
$V_L$-CDR3: QQSSNVPYT (SEQ ID NO: 18).

In one embodiment, the anti-hTREM-1 antibody, or antigen-binding fragment thereof, comprises a VL which comprises at least one (e.g., 1, 2 or 3) of the following CDR, and preferably the three following CDRs:

$V_L$-CDR1: RASESVDNYGISFMN (SEQ ID NO: 24);
$V_L$-CDR2: AASNQGS (SEQ ID NO: 25); and/or
$V_L$-CDR3: QQSKEVPWT (SEQ ID NO: 26).

In one embodiment, any of $V_L$-CDR1, $V_L$-CDR2 and/or $V_L$-CDR3 having an amino acid sequence as set forth in any one of SEQ ID NOs 4-6, 9-11, 14-16, 18, 20, 21 and 24-25 as described hereinabove can be characterized as having 1, 2, 3 or more amino acid(s) being substituted by a different amino acid. In one embodiment, any of $V_H$-CDR1, $V_H$-CDR2 and/or $V_H$-CDR3 with SEQ ID NOs 4-6, 9-11, 14-16, 18, 20, 21 and 24-25 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in any one of SEQ ID NOs 4-6, 9-11, 14-16, 18, 20, 21 and 24-25.

According to one embodiment, the anti-hTREM-1 antibody, or antigen-binding fragment thereof, comprises:

a variable region of the heavy chain (VH) which comprises at least one, preferably at least two, more preferably the three following CDRs:
  $V_H$-CDR1: NTYIH (SEQ ID NO: 1);
  $V_H$-CDR2: RIDPAX$_1$GX$_2$TKYX$_3$PKVX$_4$G (SEQ ID NO: 2), wherein $X_1$ is N or G, $X_2$ is N or R, $X_3$ is A, D, or S, $X_4$ is Q or K; or RIDPAX$_1$GX$_2$TKYX$_3$PKFX$_4$G (SEQ ID NO: 39), wherein $X_1$ is N or G, $X_2$ is N or R, $X_3$ is A, D, or S, $X_4$ is Q or K; and/or
  $V_H$-CDR3: HX$_5$GX$_6$TMDY (SEQ ID NO: 3), wherein $X_5$ is Y or R, $X_6$ is S or G; and a variable region of the light chain (VL) which comprises at least one, preferably at least two, more preferably the three following CDRs:
  $V_L$-CDR1: RASX$_7$SVX$_8$NYGISFX$_9$N (SEQ ID NO: 4), wherein $X_7$ is E or Q, $X_8$ is D or S, $X_9$ is M or L;
  $V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and/or
  $V_L$-CDR3: QQSX$_{15}$X$_{16}$X$_{17}$PX$_{18}$T (SEQ ID NO: 6), wherein $X_{15}$ is K, R, or S, $X_{16}$ is E, H, or N, $X_{17}$ is V or F, $X_{18}$ is W or Y.

In one embodiment, the anti-hTREM-1 antibody, or antigen-binding fragment thereof, comprises:

a VH which comprises at least one, preferably at least two, more preferably the three following CDRs:
  $V_H$-CDR1: NTYIH (SEQ ID NO: 1);
  $V_H$-CDR2: RIDPAX$_1$GX$_2$TKYX$_3$PKVX$_4$G (SEQ ID NO: 2), wherein $X_1$ is N or G, $X_2$ is N or R, $X_3$ is A, D, or S, $X_4$ is Q or K; and/or
  $V_H$-CDR3: HX$_5$GX$_6$TMDY (SEQ ID NO: 3), wherein $X_5$ is Y or R, $X_6$ is S or G; and a VL which comprises at least one, preferably at least two, more preferably the three following CDRs:
  $V_L$-CDR1: RASX$_7$SVX$_8$NYGISFX$_9$N (SEQ ID NO: 4), wherein $X_7$ is E or Q, $X_8$ is D or S, $X_9$ is M or L;
  $V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and/or
  $V_L$-CDR3: QQSX$_{15}$X$_{16}$X$_{17}$PX$_{18}$T (SEQ ID NO: 6), wherein $X_{15}$ is K, R, or S, $X_{16}$ is E, H, or N, $X_{17}$ is V or F, $X_{18}$ is W or Y.

In one embodiment, the anti-hTREM-1 antibody, or antigen-binding fragment thereof, comprises:

a VH which comprises at least one, preferably at least two, more preferably the three following CDRs:
  $V_H$-CDR1: NTYIH (SEQ ID NO: 1);
  $V_H$-CDR2: RIDPAX$_1$GX$_2$TKYX$_3$PKFX$_4$G (SEQ ID NO: 39), wherein $X_1$ is N or G, $X_2$ is N or R, $X_3$ is A, D, or S, $X_4$ is Q or K; and/or
  $V_H$-CDR3: HX$_5$GX$_6$TMDY (SEQ ID NO: 3), wherein $X_5$ is Y or R, $X_6$ is S or G; and a VL which comprises at least one, preferably at least two, more preferably the three following CDRs:
  $V_L$-CDR1: RASX$_7$SVX$_8$NYGISFX$_9$N (SEQ ID NO: 4), wherein $X_7$ is E or Q, $X_5$ is D or S, $X_9$ is M or L;
  $V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and/or
  $V_L$-CDR3: QQSX$_{15}$X$_{16}$X$_{17}$PX$_{18}$T (SEQ ID NO: 6), wherein $X_{15}$ is K, R, or S, $X_{16}$ is E, H, or N, $X_{17}$ is V or F, $X_{18}$ is W or Y.

According to one embodiment, the anti-hTREM-1 antibody, or antigen-binding fragment thereof, comprises:

a VH which comprises the three following CDRs:
  $V_H$-CDR1: NTYIH (SEQ ID NO: 1);
  $V_H$-CDR2: RIDPAX$_1$GX$_2$TKYX$_3$PKVX$_4$G (SEQ ID NO: 2), wherein $X_1$ is N or G, $X_2$ is N or R, $X_3$ is A, D, or S, $X_4$ is Q or K; or RIDPAX$_1$GX$_2$TKYX$_3$PKFX$_4$G (SEQ ID NO: 39), wherein $X_1$ is N or G, $X_2$ is N or R, $X_3$ is A, D, or S, $X_4$ is Q or K; and
  $V_H$-CDR3: HX$_5$GX$_6$TMDY (SEQ ID NO: 3), wherein $X_5$ is Y or R, $X_6$ is S or G; and a VL which comprises the three following CDRs:
  $V_L$-CDR1: RASX$_7$SVX$_8$NYGISFX$_9$N (SEQ ID NO: 4), wherein $X_7$ is E or Q, $X_8$ is D or S, $X_9$ is M or L;
  $V_L$-CDR2: AAX$_{10}$X$_{11}$X$_{12}$X$_{13}$X$_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and $V_L$-CDR3: $QQSX_{15}X_{16}X_{17}PX_{18}T$ (SEQ ID NO: 6), wherein $X_{15}$ is K, R, or S, $X_{16}$ is E, H, or N, $X_{17}$ is V or F, $X_{18}$ is W or Y.

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: $RIDPAX_1GX_2TKYX_3PKVX_4G$ (SEQ ID NO: 2), wherein $X_1$ is N or G, $X_2$ is N or R, $X_3$ is A, D, or S, $X_4$ is Q or K; and $V_H$-CDR3: $HX_5GX_6TMDY$ (SEQ ID NO: 3), wherein $X_5$ is Y or R, $X_6$ is S or G; and a VL which comprises the three following CDRs:

$V_L$-CDR1: $RASX_7SVX_8NYGISFX_9N$ (SEQ ID NO: 4), wherein $X_7$ is E or Q, $X_8$ is D or S, $X_9$ is M or L;

$V_L$-CDR2: $AAX_{10}X_{11}X_{12}X_{13}X_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and $V_L$-CDR3: $QQSX_{15}X_{16}X_{17}PX_{18}T$ (SEQ ID NO: 6), wherein $X_{15}$ is K, R, or S, $X_{16}$ is E, H, or N, $X_{17}$ is V or F, $X_{18}$ is W or Y.

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: $RIDPAX_1GX_2TKYX_3PKFX_4G$ (SEQ ID NO: 39), wherein $X_1$ is N or G, $X_2$ is N or R, $X_3$ is A, D, or S, $X_4$ is Q or K; and $V_H$-CDR3: $HX_5GX_6TMDY$ (SEQ ID NO: 3), wherein $X_5$ is Y or R, $X_6$ is S or G; and a VL which comprises the three following CDRs:

$V_L$-CDR1: $RASX_7SVX_8NYGISFX_9N$ (SEQ ID NO: 4), wherein $X_7$ is E or Q, $X_5$ is D or S, $X_9$ is M or L;

$V_L$-CDR2: $AAX_{10}X_{11}X_{12}X_{13}X_{14}$ (SEQ ID NO: 5), wherein $X_{10}$ is S or E, $X_{11}$ is N or Y, $X_{12}$ is Q or R, $X_{13}$ is G, A, or K, $X_{14}$ is S or R; and $V_L$-CDR3: $QQSX_{15}X_{16}X_{17}PX_{18}T$ (SEQ ID NO: 6), wherein $X_{15}$ is K, R, or S, $X_{16}$ is E, H, or N, $X_{17}$ is V or F, $X_{18}$ is W or Y.

In one embodiment, the anti-hTREM-1 antibody, or antigen-binding fragment thereof, comprises the following CDRs:

$V_H$-CDR1: NTYIH (SEQ ID NO: 1), $V_H$-CDR2: RIDPAGGRTKYDPKVKG (SEQ ID NO: 7), $V_H$-CDR3: HYGGTMDY (SEQ ID NO: 8), $V_L$-CDR1: RASESVDNYGISFLN (SEQ ID NO: 9), $V_L$-CDR2: AAEYRGR (SEQ ID NO: 10), and $V_L$-CDR3: QQSRHVPYT (SEQ ID NO: 11); or $V_H$-CDR1: NTYIH (SEQ ID NO: 1), $V_H$-CDR2: RIDPAGGRTKYSPKVQG (SEQ ID NO: 12), $V_H$-CDR3: HRGGTMDY (SEQ ID NO: 13), $V_L$-CDR1: RASQSVSNYGISFLN (SEQ ID NO: 14), $V_L$-CDR2: AASYQKR (SEQ ID NO: 15), and $V_L$-CDR3: QQSSNFPWT (SEQ ID NO: 16); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRGR (SEQ ID NO: 10), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVQG (SEQ ID NO: 19), $V_H$-CDR3: HYGGTMDY (SEQ ID NO: 8), $V_L$-CDR1: RASQSVSNYGISFLN (SEQ ID NO: 14), $V_L$-CDR2: AAEYQGR (SEQ ID NO: 20), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRAR (SEQ ID NO: 21), and $V_L$-CDR3: QQSSNVPYT (SEQ ID NO: 18); or $V_H$-CDR1: NTYIH (SEQ ID NO: 1), $V_H$-CDR2: RIDPANGNTKYAPKVQG (SEQ ID NO: 22), $V_H$-CDR3: HYGSTMDY (SEQ ID NO: 23), $V_L$-CDR1: RASESVDNYGISFMN (SEQ ID NO: 24), $V_L$-CDR2: AASNQGS (SEQ ID NO: 25), and $V_L$-CDR3: QQSKEVPWT (SEQ ID NO: 26); or $V_H$-CDR1: NTYIH (SEQ ID NO: 1), $V_H$-CDR2: RIDPANGNTKYAPKFQG (SEQ ID NO: 40), $V_H$-CDR3: HYGSTMDY (SEQ ID NO: 23), $V_L$-CDR1: RASESVDNYGISFMN (SEQ ID NO: 24), $V_L$-CDR2: AASNQGS (SEQ ID NO: 25), and $V_L$-CDR3: QQSKEVPWT (SEQ ID NO: 26).

In one embodiment, the anti-hTREM-1 antibody, or antigen-binding fragment thereof, comprises the following CDRs:

$V_H$-CDR1: NTYIH (SEQ ID NO: 1), $V_H$-CDR2: RIDPAGGRTKYDPKVKG (SEQ ID NO: 7), $V_H$-CDR3: HYGGTMDY (SEQ ID NO: 8), $V_L$-CDR1: RASESVDNYGISFLN (SEQ ID NO: 9), $V_L$-CDR2: AAEYRGR (SEQ ID NO: 10), and $V_L$-CDR3: QQSRHVPYT (SEQ ID NO: 11); or $V_H$-CDR1: NTYIH (SEQ ID NO: 1), $V_H$-CDR2: RIDPAGGRTKYSPKVQG (SEQ ID NO: 12), $V_H$-CDR3: HRGGTMDY (SEQ ID NO: 13), $V_L$-CDR1: RASQSVSNYGISFLN (SEQ ID NO: 14), $V_L$-CDR2: AASYQKR (SEQ ID NO: 15), and $V_L$-CDR3: QQSSNFPWT (SEQ ID NO: 16); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRGR (SEQ ID NO: 10), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVQG (SEQ ID NO: 19), $V_H$-CDR3: HYGGTMDY (SEQ ID NO: 8), $V_L$-CDR1: RASQSVSNYGISFLN (SEQ ID NO: 14), $V_L$-CDR2: AAEYQGR (SEQ ID NO: 20), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRAR (SEQ ID NO: 21), and $V_L$-CDR3: QQSSNVPYT (SEQ ID NO: 18); or $V_H$-CDR1: NTYIH (SEQ ID NO: 1), $V_H$-CDR2: RIDPANGNTKYAPKVQG (SEQ ID NO: 22), $V_H$-CDR3: HYGSTMDY (SEQ ID NO: 23), $V_L$-CDR1: RASESVDNYGISFMN (SEQ ID NO: 24), $V_L$-CDR2: AASNQGS (SEQ ID NO: 25), and $V_L$-CDR3: QQSKEVPWT (SEQ ID NO: 26).

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: RIDPAGGRTKYDPKVKG (SEQ ID NO: 7); and $V_H$-CDR3: HYGGTMDY (SEQ ID NO: 8); and a VL which comprises the three following CDRs:

$V_L$-CDR1: RASESVDNYGISFLN (SEQ ID NO: 9);

$V_L$-CDR2: AAEYRGR (SEQ ID NO: 10); and $V_L$-CDR3: QQSRHVPYT (SEQ ID NO: 11).

In one embodiment, any of $V_H$-CDR1, $V_H$-CDR2 and/or $V_H$-CDR3 with SEQ ID NOs 1, 7, 8 and/or any of $V_L$-CDR1, $V_L$-CDR2 and $V_L$-CDR3 with SEQ ID NOs 9-11 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 7, 8 and 9-11.

An example of antibodies comprising a VH comprising $V_H$-CDR1, $V_H$-CDR2 and $V_H$-CDR3 with SEQ ID NOs 1, 7, 8 and a VL comprising $V_L$-CDR1, $V_L$-CDR2 and $V_L$-CDR3 with SEQ ID NOs 9-11 is INO-10-3. An example of antigen-binding antibody fragments comprising a VH comprising $V_H$-CDR1, $V_H$-CDR2 and $V_H$-CDR3 with SEQ ID NOs 1, 7, 8 and a VL comprising $V_L$-CDR1, $V_L$-CDR2 and $V_L$-CDR3 with SEQ ID NOs 9-11 is the Fab fragment INO-10-F3 (or F3).

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: RIDPAGGRTKYSPKVQG (SEQ ID NO: 12); and $V_H$-CDR3: HRGGTMDY (SEQ ID NO: 13); and a VL which comprises the three following CDRs:

$V_L$-CDR1: RASQSVSNYGISFLN (SEQ ID NO: 14);

$V_L$-CDR2: AASYQKR (SEQ ID NO: 15) and $V_L$-CDR3: QQSSNFPWT (SEQ ID NO: 16).

In one embodiment, any of $V_H$-CDR1, $V_H$-CDR2 and/or $V_H$-CDR3 with SEQ ID NOs 1, 12, 13 and/or any of $V_L$-CDR1, $V_L$-CDR2 and $V_L$-CDR3 with SEQ ID NOs 14-16 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 12, 13 and 14-16.

An example of antibodies comprising a VH comprising $V_H$-CDR1, $V_H$-CDR2 and $V_H$-CDR3 with SEQ ID NOs 1, 12, 13 and a VL comprising $V_L$-CDR1, $V_L$-CDR2 and $V_L$-CDR3 with SEQ ID NOs 14-16 is INO-10-2. An example of antigen-binding antibody fragments comprising a VH comprising $V_H$-CDR1, $V_H$-CDR2 and $V_H$-CDR3 with SEQ ID NOs 1, 12, 13 and a VL comprising $V_L$-CDR1, $V_L$-CDR2 and $V_L$-CDR3 with SEQ ID NOs 14-16 is the Fab fragment INO-10-F2 (or F2).

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: RIDPAGGRTKYAPKVKG (SEQ ID NO: 17); and $V_H$-CDR3: HRGGTMDY (SEQ ID NO: 13); and a VL which comprises the three following CDRs:

$V_L$-CDR1: RASQSVSNYGISFLN (SEQ ID NO: 14);

$V_L$-CDR2: AAEYRGR (SEQ ID NO: 10); and $V_L$-CDR3: QQSSNVPYT (SEQ ID NO: 18).

In one embodiment, any of $V_H$-CDR1, $V_H$-CDR2 and/or $V_H$-CDR3 with SEQ ID NOs 1, 17, 13 and/or any of $V_L$-CDR1, $V_L$-CDR2 and $V_L$-CDR3 with SEQ ID NOs 14, 10, 18 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 17, 13, 14, 10, and 18.

An example of antibodies comprising a VH comprising $V_H$-CDR1, $V_H$-CDR2 and $V_H$-CDR3 with SEQ ID NOs 1, 17, 13 and a VL comprising $V_L$-CDR1, $V_L$-CDR2 and $V_L$-CDR3 with SEQ ID NOs 14, 10, 18 is INO-10-4. An example of antigen-binding antibody fragments comprising a VH comprising $V_H$-CDR1, $V_H$-CDR2 and $V_H$-CDR3 with SEQ ID NOs 1, 17, 13 and a VL comprising $V_L$-CDR1, $V_L$-CDR2 and $V_L$-CDR3 with SEQ ID NOs 14, 10, 18 is the Fab fragment INO-10-F4 (or F4).

In one embodiment, the anti-hTREM-1 antibody, or antigen-binding fragment thereof, comprises:

a VH which comprises the three following CDRs:

$V_H$-CDR1: NTYIH (SEQ ID NO: 1);

$V_H$-CDR2: RIDPAGGRTKYAPKVQG (SEQ ID NO: 19); and $V_H$-CDR3: HYGGTMDY (SEQ ID NO: 8); and a VL which comprises the three following CDRs:

$V_L$-CDR1: RASQSVSNYGISFLN (SEQ ID NO: 14);

$V_L$-CDR2: AAEYQGR (SEQ ID NO: 20); and $V_L$-CDR3: QQSSNVPYT (SEQ ID NO: 18).

In one embodiment, any of $V_H$-CDR1, $V_H$-CDR2 and/or $V_H$-CDR3 with SEQ ID NOs 1, 19, 8 and/or any of $V_L$-CDR1, $V_L$-CDR2 and $V_L$-CDR3 with SEQ ID NOs 14, 20, 18 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 19, 8, 14, 20, and 18.

An example of antibodies comprising a VH comprising $V_H$-CDR1, $V_H$-CDR2 and $V_H$-CDR3 with SEQ ID NOs 1, 19, 8 and a VL comprising $V_L$-CDR1, $V_L$-CDR2 and $V_L$-CDR3 with SEQ ID NOs 14, 20, 18 is INO-10-5. An example of antigen-binding antibody fragments comprising a VH comprising $V_H$-CDR1, $V_H$-CDR2 and $V_H$-CDR3 with SEQ ID NOs 1, 19, 8 and a VL comprising $V_L$-CDR1, $V_L$-CDR2 and $V_L$-CDR3 with SEQ ID NOs 14, 20, 18 is the Fab fragment INO-10-F5 (or F5).

In one embodiment, the anti-hTREM-1 antibody, or antigen-binding fragment thereof, comprises:

a VH which comprises the three following CDRs:
$V_H$-CDR1: NTYIH (SEQ ID NO: 1);
$V_H$-CDR2: RIDPAGGRTKYAPKVKG (SEQ ID NO: 17); and
$V_H$-CDR3: HRGGTMDY (SEQ ID NO: 13); and
a VL which comprises the three following CDRs:
$V_L$-CDR1: RASQSVSNYGISFLN (SEQ ID NO: 14);
$V_L$-CDR2: AAEYRAR (SEQ ID NO: 21); and
$V_L$-CDR3: QQSSNVPYT (SEQ ID NO: 18).

In one embodiment, any of $V_H$-CDR1, $V_H$-CDR2 and/or $V_H$-CDR3 with SEQ ID NOs 1, 17, 13 and/or any of $V_L$-CDR1, $V_L$-CDR2 and $V_L$-CDR3 with SEQ ID NOs 14, 21, 18 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 17, 13, 14, 21, and 18.

An example of antibodies comprising a VH comprising $V_H$-CDR1, $V_H$-CDR2 and $V_H$-CDR3 with SEQ ID NOs 1, 17, 13 and a VL comprising $V_L$-CDR1, $V_L$-CDR2 and $V_L$-CDR3 with SEQ ID NOs 14, 21, 18 is INO-10-6. An example of antigen-binding antibody fragments comprising a VH comprising $V_H$-CDR1, $V_H$-CDR2 and $V_H$-CDR3 with SEQ ID NOs 1, 17, 13 and a VL comprising $V_L$-CDR1, $V_L$-CDR2 and $V_L$-CDR3 with SEQ ID NOs 14, 21, 18 is the Fab fragment INO-10-F6 (or F6).

In one embodiment, the anti-hTREM-1 antibody, or antigen-binding fragment thereof, comprises:
a VH which comprises the three following CDRs:
$V_H$-CDR1: NTYIH (SEQ ID NO: 1);
$V_H$-CDR2: RIDPANGNTKYAPKVQG (SEQ ID NO: 22); and
$V_H$-CDR3: HYGSTMDY (SEQ ID NO: 23); and
a VL which comprises the three following CDRs:
$V_L$-CDR1: RASESVDNYGISFMN (SEQ ID NO: 24);
$V_L$-CDR2: AASNQGS (SEQ ID NO: 25); and
$V_L$-CDR3: QQSKEVPWT (SEQ ID NO: 26).

In one embodiment, any of $V_H$-CDR1, $V_H$-CDR2 and/or $V_H$-CDR3 with SEQ ID NOs 1, 22, 23 and/or any of $V_L$-CDR1, $V_L$-CDR2 and $V_L$-CDR3 with SEQ ID NOs 24-26 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 22, 23 and 24-26.

An example of antibodies comprising a VH comprising $V_H$-CDR1, $V_H$-CDR2 and $V_H$-CDR3 with SEQ ID NOs 1, 22, 23 and a VL comprising $V_L$-CDR1, $V_L$-CDR2 and $V_L$-CDR3 with SEQ ID NOs 24-26 is INO-10-1. An example of antigen-binding antibody fragments comprising a VH comprising $V_H$-CDR1, $V_H$-CDR2 and $V_H$-CDR3 with SEQ ID NOs 1, 22, 23 and a VL comprising $V_L$-CDR1, $V_L$-CDR2 and $V_L$-CDR3 with SEQ ID NOs 24-26 is the Fab fragment INO-10-F1 (or F1).

In one embodiment, the anti-hTREM-1 antibody, or antigen-binding fragment thereof, comprises:
a VH which comprises the three following CDRs:
$V_H$-CDR1: NTYIH (SEQ ID NO: 1);
$V_H$-CDR2: RIDPANGNTKYAPKFQG (SEQ ID NO: 40); and
$V_H$-CDR3: HYGSTMDY (SEQ ID NO: 23); and
a VL which comprises the three following CDRs:
$V_L$-CDR1: RASESVDNYGISFMN (SEQ ID NO: 24);
$V_L$-CDR2: AASNQGS (SEQ ID NO: 25); and
$V_L$-CDR3: QQSKEVPWT (SEQ ID NO: 26).

In one embodiment, any of $V_H$-CDR1, $V_H$-CDR2 and/or $V_H$-CDR3 with SEQ ID NOs 1, 40, 23 and/or any of $V_L$-CDR1, $V_L$-CDR2 and $V_L$-CDR3 with SEQ ID NOs 24-26 can be characterized as having an amino acid sequence that shares at least 70%, 75%, 80%, 85%, 90%, 95%, 96%, 97%, 98%, 99% or more of identity with the particular CDR or sets of CDRs listed in the corresponding SEQ ID NOs. In other words, in one embodiment, the $V_H$-CDR1, $V_H$-CDR2, $V_H$-CDR3, $V_L$-CDR1, $V_L$-CDR2 and/or $V_L$-CDR3 as described hereinabove have an amino acid sequence that shares at least 70%, 75%, 80%, 85%, 90%, 95%, 96%, 97%, 98%, 99% or more of identity with the corresponding amino acid sequence as set forth in SEQ ID NOs 1, 40, 23 and 24-26.

An example of antibodies comprising a VH comprising $V_H$-CDR1, $V_H$-CDR2 and $V_H$-CDR3 with SEQ ID NOs 1, 40, 23 and a VL comprising $V_L$-CDR1, $V_L$-CDR2 and $V_L$-CDR3 with SEQ ID NOs 24-26 is INO-10. An example of antigen-binding antibody fragments comprising a VH comprising $V_H$-CDR1, $V_H$-CDR2 and $V_H$-CDR3 with SEQ ID NOs 1, 40, 23 and a VL comprising $V_L$-CDR1, $V_L$-CDR2 and $V_L$-CDR3 with SEQ ID NOs 24-26 is the Fab fragment INO-10-F.

According to one embodiment, the anti-hTREM-1 antibody, or antigen-binding fragment thereof, comprises a variable region of the heavy chain (VH) comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, and SEQ ID NO: 41.

In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, SEQ ID NO: 41 and sequences having at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, SEQ ID NO: 32, or SEQ ID NO: 41.

In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, and SEQ ID NO: 41 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, and SEQ ID NO: 41 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs.

In one embodiment, the anti-hTREM-1 antibody, or antigen-binding fragment thereof, comprises a VH having an amino acid sequence that shares at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, SEQ ID NO: 32, and/or SEQ ID NO: 41. In one embodiment, the anti-hTREM-1 antibody, or antigen-binding fragment thereof, comprises a VH having an amino acid sequence of the framework regions that shares at least 70%, 75%, 80%, 85%, 90%, 95%, 96%, 97%, 98%, 99% or more of identity with the amino acid sequence of the framework regions (i.e., the non-CDR regions) of SEQ ID NO: 27, SEQ ID NO: 28, SEQ ID NO: 29, SEQ ID NO: 30, SEQ ID NO: 31, SEQ ID NO: 32, and/or SEQ ID NO: 41.

According to one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, and SEQ ID NO: 32.

In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32 and sequences having at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, or SEQ ID NO: 32.

In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, and SEQ ID NO: 32 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In one embodiment, the anti-hTREM-1 antibody, or antigen-binding fragment thereof, comprises a VH comprising or consisting of a sequence selected from the group comprising or consisting of SEQ ID NO: 27, SEQ ID NO: 28, SEQ ID NO: 29, SEQ ID NO: 30, SEQ ID NO: 31, and SEQ ID NO: 32 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs.

In one embodiment, the anti-hTREM-1 antibody, or antigen-binding fragment thereof, comprises a VH having an amino acid sequence that shares at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, and/or SEQ ID NO: 32. In one embodiment, the anti-hTREM-1 antibody, or antigen-binding fragment thereof, comprises a VH having an amino acid sequence of the framework regions that shares at least 70%, 75%, 80%, 85%, 90%, 95%, 96%, 97%, 98%, 99% or more of identity with the amino acid sequence of the framework regions (i.e., the non-CDR regions) of SEQ ID NO: 27, SEQ ID NO: 28, SEQ ID NO: 29, SEQ ID NO: 30, SEQ ID NO: 31, and/or SEQ ID NO: 32.

According to one embodiment, the anti-hTREM-1 antibody, or antigen-binding fragment thereof, comprises a variable region of the light chain (VL) comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, and SEQ ID NO: 42.

In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, SEQ ID NO: 42 and sequences having at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, SEQ ID NO: 38, or SEQ ID NO: 42.

In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, and SEQ ID NO: 42 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, and SEQ ID NO: 42 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs.

In one embodiment, the anti-hTREM-1 antibody, or antigen-binding fragment thereof, comprises a VL having an amino acid sequence that shares at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, SEQ ID NO: 38, and/or SEQ ID NO: 42. In one embodiment, the anti-hTREM-1 antibody, or antigen-binding fragment thereof, comprises a VL having an amino acid sequence of the framework regions that shares at least 70%, 75%, 80%, 85%, 90%, 95%, 96%, 97%, 98%, 99% or more of identity with the amino acid sequence of the framework regions (i.e., non-CDR regions) of SEQ ID NO: 33, SEQ ID NO: 34, SEQ ID NO: 35, SEQ ID NO: 36, SEQ ID NO: 37, SEQ ID NO: 38, and/or SEQ ID NO: 42.

According to one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, and SEQ ID NO: 38.

In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38 and sequences having at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, or SEQ ID NO: 38.

In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, and SEQ ID NO: 38 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid. In one embodiment, the anti-hTREM-1 antibody, or antigen-binding fragment thereof, comprises a VL comprising or consisting of a sequence selected from the group comprising or consisting of SEQ ID NO: 33, SEQ ID NO: 34, SEQ ID NO: 35, SEQ ID NO: 36, SEQ ID NO: 37, and SEQ ID NO: 38 with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more amino acid(s) substituted by a different amino acid, wherein said amino acid substitution(s) do(es) not occur in any of the three CDRs.

In one embodiment, the anti-hTREM-1 antibody, or antigen-binding fragment thereof, comprises a VL having an amino acid sequence that shares at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, and/or SEQ ID NO: 38. In one embodiment, the anti-hTREM-1 antibody, or antigen-binding fragment thereof, comprises a VL having an amino acid sequence of the framework regions that shares at least 70%, 75%, 80%, 85%, 90%, 95%, 96%, 97%, 98%, 99% or more of identity with the amino acid sequence of the framework regions (i.e., the non-CDR regions) of SEQ ID NO: 33, SEQ ID NO: 34, SEQ ID NO: 35, SEQ ID NO: 36, SEQ ID NO: 37, and/or SEQ ID NO: 38.

According to one embodiment, the anti-hTREM-1 antibody, or antigen-binding fragment thereof, comprises:

a variable region of the heavy chain (VH) comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO:32, SEQ ID NO: 41 and sequences having at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, SEQ ID NO:32, or SEQ ID NO: 41; and a variable region of the light chain (VL) comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, SEQ ID NO: 42 and sequences having at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, SEQ ID NO: 38, or SEQ ID NO: 42.

In one embodiment, the anti-hTREM-1 antibody, or antigen-binding fragment thereof, comprises:

a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, and SEQ ID NO: 41, or a VH having, comprising or consisting of a sequence of the framework regions sharing at least 70%, 75%, 80%, 85%, 90%, 95%, 96%, 97%, 98%, 99% or more of identity with the framework regions (i.e., the non-CDR regions) of SEQ ID NO: 27, SEQ ID NO: 28, SEQ ID NO: 29, SEQ ID NO: 30, SEQ ID NO: 31, SEQ ID NO: 32, or SEQ ID NO: 41; and a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, and SEQ ID NO: 42, or a VL having, comprising or consisting of a sequence of the framework regions sharing at least 70%, 75%, 80%, 85%, 90%, 95%, 96%, 97%, 98%, 99% or more of identity with the framework regions (i.e., the non-CDR regions) of SEQ ID NO: 33, SEQ ID NO: 34, SEQ ID NO: 35, SEQ ID NO: 36, SEQ ID NO: 37, SEQ ID NO: 38, or SEQ ID NO: 42.

According to one embodiment, the anti-hTREM-1 antibody, or antigen-binding fragment thereof, comprises:

a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32 and sequences having at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, or SEQ ID NO: 32; and a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38 and sequences having at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, or SEQ ID NO: 38.

In one embodiment, the anti-hTREM-1 antibody, or antigen-binding fragment thereof, comprises:

a VH comprising or consisting of a sequence selected from the group comprising or consisting of SEQ ID NO: 27, SEQ ID NO: 28, SEQ ID NO: 29, SEQ ID NO: 30, SEQ ID NO: 31, and SEQ ID NO: 32, or a VH having, comprising or consisting of a sequence of the framework regions sharing at least 70%, 75%, 80%, 85%, 90%, 95%, 96%, 97%, 98%, 99% or more of identity with the framework regions (i.e., the non-CDR regions) of SEQ ID NO: 27, SEQ ID NO: 28, SEQ ID NO: 29, SEQ ID NO: 30, SEQ ID NO: 31, or SEQ ID NO: 32; and a VL comprising or consisting of a sequence selected from the group comprising or consisting of SEQ ID NO: 33, SEQ ID NO: 34, SEQ ID NO: 35, SEQ ID NO: 36, SEQ ID NO: 37, and SEQ ID NO: 38, or a VL having, comprising or consisting of a sequence of the framework regions sharing at least 70%, 75%, 80%, 85%, 90%, 95%, 96%, 97%, 98%, 99% or more of identity with the framework regions (i.e., the non-CDR regions) of SEQ ID NO: 33, SEQ ID NO: 34, SEQ ID NO: 35, SEQ ID NO: 36, SEQ ID NO: 37, or SEQ ID NO: 38.

In one embodiment, the anti-hTREM-1 antibody, or antigen-binding fragment thereof, comprises:

a VH comprising or consisting of SEQ ID NO: 27 or a sequence having at least 70%, 75%, 80%, 85%, 90%, 95%, 96%, 97%, 98%, 99% or more of identity with SEQ ID NO: 27, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 27; and a VL comprising or consisting of a sequence selected from the group comprising or consisting of SEQ ID NO: 33, SEQ ID NO: 34, SEQ ID NO: 35, SEQ ID NO: 36, SEQ ID NO: 37, SEQ ID NO: 38, SEQ ID NO: 42 and sequences having at least 70%, 75%, 80%, 85%, 90%, 95%, 96%, 97%, 98%, 99% or more of identity with SEQ ID NO: 33, SEQ ID NO: 34, SEQ ID NO: 35, SEQ ID NO: 36, SEQ ID NO: 37, SEQ ID NO: 38, or SEQ ID NO: 42, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 33, SEQ ID NO: 34, SEQ ID NO: 35, SEQ ID NO: 36, SEQ ID NO: 37, SEQ ID NO: 38, or SEQ ID NO: 42.

In one embodiment, the anti-hTREM-1 antibody, or antigen-binding fragment thereof, comprises:

a VH comprising or consisting of a sequence selected from the group comprising or consisting of SEQ ID NO: 27, SEQ ID NO: 28, SEQ ID NO: 29, SEQ ID NO: 30, SEQ ID NO: 31, SEQ ID NO: 32, SEQ ID NO: 41 and sequences having at least 70%, 75%, 80%, 85%, 90%, 95%, 96%, 97%, 98%, 99% or more of identity with SEQ ID NO: 27, SEQ ID NO: 28, SEQ ID NO: 29, SEQ ID NO: 30, SEQ ID NO: 31, SEQ ID NO: 32, or SEQ ID NO: 41, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 27, SEQ ID NO: 28, SEQ ID NO: 29, SEQ ID NO: 30, SEQ ID NO: 31, SEQ ID NO: 32, or SEQ ID NO: 41; and a VL comprising or consisting of SEQ ID NO: 33 or a sequence having at least 70%, 75%, 80%, 85%, 90%, 95%, 96%, 97%, 98%, 99% or more of identity with SEQ ID NO: 33, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 33.

According to one embodiment, the anti-hTREM-1 antibody, or antigen-binding fragment thereof, comprises:

a VH comprising or consisting of SEQ ID NO: 27 or a sequence having at least 70%, 75%, 80%, 85%, 90%, 95%, 96%, 97%, 98%, 99% or more of identity with SEQ ID NO: 27, or a VH having a sequence of the framework regions sharing at least 70%, 75%, 80%, 85%, 90%, 95%, 96%, 97%, 98%, 99% or more of identity with the framework regions of SEQ ID NO: 27; and a VL comprising or consisting of SEQ ID NO: 33 or a sequence having at least 70%, 75%, 80%, 85%, 90%, 95%, 96%, 97%, 98%, 99% or more of identity with SEQ ID NO: 33, or a VL having a sequence of the framework regions sharing at least 70%, 75%, 80%, 85%, 90%, 95%, 96%, 97%, 98%, 99% or more of identity with the framework regions of SEQ ID NO: 33; or a VH comprising or consisting of SEQ ID NO: 28 or a sequence having at least 70%, 75%, 80%, 85%, 90%, 95%, 96%, 97%, 98%, 99% or more of identity with SEQ ID NO: 28, or a VH having a sequence of the framework regions sharing at least 70%, 75%, 80%, 85%, 90%, 95%, 96%, 97%, 98%, 99% or more of identity with the framework regions of SEQ ID NO: 28; and a VL comprising or consisting of SEQ ID NO: 34 or a sequence having at least 70%, 75%, 80%, 85%, 90%, 95%, 96%, 97%, 98%, 99% or more of identity with SEQ ID NO: 34, or a VL having a sequence of the framework regions sharing at least 70%, 75%, 80%, 85%, 90%, 95%, 96%, 97%, 98%, 99% or more of identity with the framework regions of SEQ ID NO: 34; or a VH comprising or consisting of SEQ ID NO: 29 or a sequence having at least 70%, 75%, 80%, 85%, 90%, 95%, 96%, 97%, 98%, 99% or more of identity with SEQ ID NO: 29, or a VH having a sequence of the framework regions sharing at least 70%, 75%, 80%, 85%, 90%, 95%, 96%, 97%, 98%, 99% or more of identity with the framework regions of SEQ ID NO: 29; and a VL comprising or consisting of SEQ ID NO: 35 or a sequence having at least 70%, 75%, 80%, 85%, 90%, 95%, 96%, 97%, 98%, 99% or more of identity with SEQ ID NO: 35, or a VL having a sequence of the framework regions sharing at least 70%, 75%, 80%, 85%, 90%, 95%, 96%, 97%, 98%, 99% or more of identity with the framework regions of SEQ ID NO: 35; or a VH comprising or consisting of SEQ ID NO: 30 or a sequence having at least 70%, 75%, 80%, 85%, 90%, 95%, 96%, 97%, 98%, 99% or more of identity with SEQ ID NO: 30, or a VH having a sequence of the framework regions sharing at least 70%, 75%, 80%, 85%, 90%, 95%, 96%, 97%, 98%, 99% or more of identity with the framework regions of SEQ ID NO: 30; and a VL comprising or consisting of SEQ ID NO: 36 or a sequence having at least 70%, 75%, 80%, 85%, 90%, 95%, 96%, 97%, 98%, 99% or more of identity with SEQ ID NO: 36, or a VL having a sequence of the framework regions sharing at least 70%, 75%, 80%, 85%, 90%, 95%, 96%, 97%, 98%, 99% or more of identity with the framework regions of SEQ ID NO: 36; or a VH comprising or consisting of SEQ ID NO: 31 or a sequence having at least 70%, 75%, 80%, 85%, 90%, 95%, 96%, 97%, 98%, 99% or more of identity with SEQ ID NO: 31, or a VH having a sequence of the framework regions sharing at least 70%, 75%, 80%, 85%, 90%, 95%, 96%, 97%, 98%, 99% or more of identity with the framework regions of SEQ ID NO: 31; and a VL comprising or consisting of SEQ ID NO: 37 or a sequence having at least 70%, 75%, 80%, 85%, 90%, 95%, 96%, 97%, 98%, 99% or more of identity with SEQ ID NO: 37, or a VL having a sequence of the framework regions sharing at least 70%, 75%, 80%, 85%, 90%, 95%, 96%, 97%, 98%, 99% or more of identity with the framework regions of SEQ ID NO: 37; or a VH comprising or consisting of SEQ ID NO: 32 or a sequence having at least 70%, 75%, 80%, 85%, 90%, 95%, 96%, 97%, 98%, 99% or more of identity with SEQ ID NO: 32, or a VH having a sequence of the framework regions sharing at least 70%, 75%, 80%, 85%, 90%, 95%, 96%, 97%, 98%, 99% or more of identity with the framework regions of SEQ ID NO: 32; and a VL comprising or consisting of SEQ ID NO: 38 or a sequence having at least 70%, 75%, 80%, 85%, 90%, 95%, 96%, 97%, 98%, 99% or more of identity with SEQ ID NO: 38, or a VL having a sequence of the framework regions sharing at least 70%, 75%, 80%, 85%, 90%, 95%, 96%, 97%, 98%, 99% or more of identity with the framework regions of SEQ ID NO: 38; or a VH comprising or consisting of SEQ ID NO: 41 or a sequence having at least 70%, 75%, 80%, 85%, 90%, 95%, 96%, 97%, 98%, 99% or more of identity with SEQ ID NO: 41, or a VH having a sequence of the framework regions sharing at least 70%, 75%, 80%, 85%, 90%, 95%, 96%, 97%, 98%, 99% or more of identity with the framework regions of SEQ ID NO: 41; and a VL comprising or consisting of SEQ ID NO: 42 or a sequence having at least 70%, 75%, 80%, 85%, 90%, 95%, 96%, 97%, 98%, 99% or more of identity with SEQ ID NO: 42, or a VL having a sequence of the framework regions sharing at least 70%, 75%, 80%, 85%, 90%, 95%, 96%, 97%, 98%, 99% or more of identity with the framework regions of SEQ ID NO: 42.

In one embodiment, the anti-hTREM-1 antibody, or antigen-binding fragment thereof, comprises:

a VH comprising or consisting of SEQ ID NO: 27 or a sequence having at least 70%, 75%, 80%, 85%, 90%, 95%, 96%, 97%, 98%, 99% or more of identity with SEQ ID NO: 27, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 27; and a VL comprising or consisting of SEQ ID NO: 33 or a sequence having at least 70%, 75%, 80%, 85%, 90%, 95%, 96%, 97%, 98%, 99% or more of identity with SEQ ID NO: 33, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 33.

An example of such an antibody is INO-10-3 (or MAB3). An example of such an antigen-binding antibody fragment is the Fab fragment INO-10-F3 (or F3).

In one embodiment, the anti-hTREM-1 antibody, or antigen-binding fragment thereof, comprises:

a VH comprising or consisting of SEQ ID NO: 28 or a sequence having at least 70%, 75%, 80%, 85%, 90%, 95%, 96%, 97%, 98%, 99% or more of identity with SEQ ID NO: 28, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 28; and a VL comprising or consisting of SEQ ID NO: 34 or a sequence having at least 70%, 75%, 80%, 85%, 90%, 95%, 96%, 97%, 98%, 99% or more of identity with SEQ ID NO: 34, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 34.

An example of such an antibody is INO-10-2 (or MAB2). An example of such an antigen-binding antibody fragment is the Fab fragment INO-10-F2 (or F2).

In one embodiment, the anti-hTREM-1 antibody, or antigen-binding fragment thereof, comprises:

a VH comprising or consisting of SEQ ID NO: 29 or a sequence having at least 70%, 75%, 80%, 85%, 90%, 95%, 96%, 97%, 98%, 99% or more of identity with SEQ ID NO: 29, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 29; and a VL comprising or consisting of SEQ ID NO: 35 or a sequence having at least 70%, 75%, 80%, 85%, 90%, 95%, 96%, 97%, 98%, 99% or more of identity with SEQ ID NO: 35, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 35.

An example of such an antibody is INO-10-4 (or MAB4). An example of such an antigen-binding antibody fragment is the Fab fragment INO-10-F4 (or F4).

In one embodiment, the anti-hTREM-1 antibody, or antigen-binding fragment thereof, comprises:

a VH comprising or consisting of SEQ ID NO: 30 or a sequence having at least 70%, 75%, 80%, 85%, 90%, 95%, 96%, 97%, 98%, 99% or more of identity with SEQ ID NO: 30, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 30; and a VL comprising or consisting of SEQ ID NO: 36 or a sequence having at least 70%, 75%, 80%, 85%, 90%, 95%, 96%, 97%, 98%, 99% or more of identity with SEQ ID NO: 36, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 36.

An example of such an antibody is INO-10-5 (or MAB5). An example of such an antigen-binding antibody fragment is the Fab fragment INO-10-F5 (or F5).

In one embodiment, the anti-hTREM-1 antibody, or antigen-binding fragment thereof, comprises:

a VH comprising or consisting of SEQ ID NO: 31 or a sequence having at least 70%, 75%, 80%, 85%, 90%, 95%, 96%, 97%, 98%, 99% or more of identity with SEQ ID NO: 31, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 31; and a VL comprising or consisting of SEQ ID NO: 37 or a sequence having at least 70%, 75%, 80%, 85%, 90%, 95%, 96%, 97%, 98%, 99% or more of identity with SEQ ID NO: 37, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 37.

An example of such an antibody is INO-10-6 (or MAB6). An example of such an antigen-binding antibody fragment is the Fab fragment INO-10-F6 (or F6).

In one embodiment, the anti-hTREM-1 antibody, or antigen-binding fragment thereof, comprises:

a VH comprising or consisting of SEQ ID NO: 32 or a sequence having at least 70%, 75%, 80%, 85%, 90%, 95%, 96%, 97%, 98%, 99% or more of identity with SEQ ID NO: 32, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 32; and a VL comprising or consisting of SEQ ID NO: 38 or a sequence having at least 70%, 75%, 80%, 85%, 90%, 95%, 96%, 97%, 98%, 99% or more of identity with SEQ ID NO: 38, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 38.

An example of such an antibody is INO-10-1 (or MAB1). An example of such an antigen-binding antibody fragment is the Fab fragment INO-10-F1 (or F1).

In one embodiment, the anti-hTREM-1 antibody, or antigen-binding fragment thereof, comprises:

a VH comprising or consisting of SEQ ID NO: 41 or a sequence having at least 70%, 75%, 80%, 85%, 90%, 95%, 96%, 97%, 98%, 99% or more of identity with SEQ ID NO: 41, or a VH having, comprising or consisting of a sequence of the framework regions sharing at least 70%, 75%, 80%, 85%, 90%, 95%, 96%, 97%, 98%, 99% or more of identity with the framework regions of SEQ ID NO: 41; and a VL comprising or consisting of SEQ ID NO: 42 or a sequence having at least 70%, 75%, 80%, 85%, 90%, 95%, 96%, 97%, 98%, 99% or more of identity with SEQ ID NO: 42, or a VL having, comprising or consisting of a sequence of the framework regions sharing at least 70%, 75%, 80%, 85%, 90%, 95%, 96%, 97%, 98%, 99% or more of identity with the framework regions of SEQ ID NO: 42.

An example of such an antibody is INO-10. An example of such an antigen-binding antibody fragment is the Fab fragment INO-10-F.

The present invention further relates to a fusion protein comprising an antibody or antigen-binding fragment thereof as described herein. For example, the fusion protein may comprise a naturally long-half-life protein or protein domain (e.g., human serum albumin).

In one embodiment, the fusion protein comprises an antibody or antigen-binding fragment thereof as described herein and HSA (human serum albumin). In one embodiment, HSA comprises or consists of the sequence SEQ ID NO: 59. In one embodiment, HSA comprises or consists of the sequence SEQ ID NO: 60. In one embodiment, HSA is thus fused (or coupled) to the antibody or antigen-binding fragment thereof as described herein, optionally via a linker.

In one embodiment, HSA is fused (or coupled) to the antibody or antigen-binding fragment thereof as described herein via a short linker, such as a linker consisting of 5 amino acids or less (e.g., linker consisting of 3, 4 or 5 amino acids). In one embodiment, HSA is fused (or coupled) to the antibody or antigen-binding fragment thereof as described herein via a long linker, such as a linker consisting of 10 amino acids or more (e.g., linker consisting of 12, 13, 14, 15, or 16 amino acids).

In one embodiment, HSA is fused (or coupled) to the heavy chain of the antibody or antigen-binding fragment thereof. In one embodiment, HSA is fused (or coupled) to the CH1 domain of the truncated heavy chain of the antibody or antigen-binding fragment thereof. In one embodiment, HSA is fused (or coupled) at the C terminus of the heavy chain (or truncated heavy chain) of the antibody or antigen-binding fragment thereof. In one embodiment, HSA is fused (or coupled) to the light chain of the antibody or antigen-binding fragment thereof. In one embodiment, HSA is fused (or coupled) at the N terminus of the light chain of the antibody or antigen-binding fragment thereof.

In one embodiment, the antibody or antigen-binding fragment thereof as described herein is modified, for example for increasing half-life in vivo, e.g., in the serum. Methods for modifying antibodies are well-known in the art and include, without limitation, conjugation to repeated chemical moieties, such as, for example, polyethylene glycol (PEG), conjugation to human serum albumin and the like.

Another object of the invention is an isolated nucleic acid encoding the antibody or antigen-binding fragment thereof according to the present invention. Another object of the invention is an isolated nucleic acid encoding the fusion protein as described herein.

An "isolated nucleic acid", as used herein, is intended to refer to a nucleic acid that is substantially separated from other nucleic acid sequences, in particular other genome DNA sequences, as well as proteins or complexes such as ribosomes and polymerases, which naturally accompany a native sequence. The term embraces a nucleic acid sequence that has been removed from its naturally occurring environment, and includes recombinant or cloned DNA or RNA isolates and chemically synthesized analogues or analogues biologically synthesized by heterologous systems. A substantially pure nucleic acid includes isolated forms of the nucleic acid.

Of course, this refers to the nucleic acid as originally isolated and does not exclude genes or sequences later added to the isolated nucleic acid by the hand of man.

In one embodiment, the isolated nucleic acid is purified.

In one embodiment, the isolated nucleic acid is purified to (i) greater than 80%, 85%, 90%, 91%, 92%, 93%, 94%, 95% or more by weight of nucleic acid as determined by absorbance methods or fluorescence methods (such as, e.g., by measuring the ratio of absorbance at 260 and 280 nm (A260/280)), and most preferably more than 96%, 97%, 98% or 99% by weight; or (ii) homogeneity as shown by agarose gel electrophoresis and using an intercalating agent such as ethidium bromide, SYBR Green, GelGreen or the like.

In one embodiment, the nucleic acid encodes at least a heavy chain variable region (VH) and/or a light chain variable region (VL) of the antibody or antigen-binding fragment thereof according to the present invention. In one embodiment, the nucleic acid may encode variable and constant regions of the antibody or antigen-binding fragment thereof according to the present invention. In one embodiment, the nucleic acid may encode heavy and light chains of the antibody or antigen-binding fragment thereof according to the present invention on separate nucleic acids or on the same nucleic acid molecule.

In one embodiment, the nucleic acid according to the present invention comprises or consists of a sequence encoding the VH of the antibody or antigen-binding fragment thereof according to the invention.

In one embodiment, the nucleic acid according to the present invention comprises or consists of a sequence encoding the VH of the antibody or antigen-binding fragment thereof according to the invention, wherein said sequence is selected from the group comprising or consisting of SEQ ID NO: 47, SEQ ID NO: 48, SEQ ID NO: 49, SEQ ID NO: 50, SEQ ID NO: 51, SEQ ID NO: 52 and sequences sharing at least 70%, 75%, 80%, 85%, 90%, 95%, 96%, 97%, 98%, 99% or more of identity with SEQ ID NO: 47, SEQ ID NO: 48, SEQ ID NO: 49, SEQ ID NO: 50, SEQ ID NO: 51, or SEQ ID NO: 52.

In one embodiment, the nucleic acid according to the present invention comprises or consists of a sequence encoding the VL of the antibody or antigen-binding fragment thereof according to the invention.

In one embodiment, the nucleic acid according to the present invention comprises or consists of a sequence encoding the VL of the antibody or antigen-binding fragment thereof according to the invention, wherein said sequence is selected from the group comprising or consisting of SEQ ID NO: 53, SEQ ID NO: 54, SEQ ID NO: 55, SEQ ID NO: 56, SEQ ID NO: 57, SEQ ID NO: 58 and sequences sharing at least 70%, 75%, 80%, 85%, 90%, 95%, 96%, 97%, 98%, 99% or more of identity with SEQ ID NO: 53, SEQ ID NO: 54, SEQ ID NO: 55, SEQ ID NO: 56, SEQ ID NO: 57, or SEQ ID NO: 58.

In one embodiment, the nucleic acid according to the present invention comprises or consists of:

- a sequence encoding the VH of the antibody or antigen-binding fragment thereof according to the present invention; and
- a sequence encoding the VL of the antibody or antigen-binding fragment thereof according to the present invention.

In one embodiment, the nucleic acid according to the present invention comprises or consists of:

- a sequence selected from the group comprising or consisting of SEQ ID NO: 47, SEQ ID NO: 48, SEQ ID NO: 49, SEQ ID NO: 50, SEQ ID NO: 51, SEQ ID NO: 52 and sequences sharing at least 70%, 75%, 80%, 85%, 90%, 95%, 96%, 97%, 98%, 99% or more of identity with SEQ ID NO: 47, SEQ ID NO: 48, SEQ ID NO: 49, SEQ ID NO: 50, SEQ ID NO: 51, or SEQ ID NO: 52; and
- a sequence selected from the group comprising or consisting of SEQ ID NO: 53, SEQ ID NO: 54, SEQ ID NO: 55, SEQ ID NO: 56, SEQ ID NO: 57, SEQ ID NO: 58 and sequences sharing at least 70%, 75%, 80%, 85%, 90%, 95%, 96%, 97%, 98%, 99% or more of identity with SEQ ID NO: 53, SEQ ID NO: 54, SEQ ID NO: 55, SEQ ID NO: 56, SEQ ID NO: 57, or SEQ ID NO: 58.

In one embodiment, the nucleic acid according to the present invention comprises or consists of:

- a sequence encoding the VH comprising or consisting of the nucleic acid sequence as set forth in SEQ ID NO: 47 or a nucleic acid sequence sharing at least 70%, 75%, 80%, 85%, 90%, 95%, 96%, 97%, 98%, 99% or more of identity with SEQ ID NO: 47; and
- a sequence encoding the VL comprising or consisting of the nucleic acid sequence as set forth in SEQ ID NO: 53 or a nucleic acid sequence sharing at least 70%, 75%, 80%, 85%, 90%, 95%, 96%, 97%, 98%, 99% or more of identity with SEQ ID NO: 53.

In one embodiment, said nucleic acid encodes for the VH and VL of the INO-10-3 antibody or of the INO-10-F3 (or F3) Fab fragment.

In one embodiment, the nucleic acid according to the present invention comprises or consists of:

- a sequence encoding the VH comprising or consisting of the nucleic acid sequence as set forth in SEQ ID NO: 48 or a nucleic acid sequence sharing at least 70%, 75%, 80%, 85%, 90%, 95%, 96%, 97%, 98%, 99% or more of identity with SEQ ID NO: 48; and
- a sequence encoding the VL comprising or consisting of the nucleic acid sequence as set forth in SEQ ID NO: 54 or a nucleic acid sequence sharing at least 70%, 75%, 80%, 85%, 90%, 95%, 96%, 97%, 98%, 99% or more of identity with SEQ ID NO: 54.

In one embodiment, said nucleic acid encodes for the VH and VL of the INO-10-2 antibody or of the INO-10-F2 (or F2) Fab fragment.

In one embodiment, the nucleic acid according to the present invention comprises or consists of:

- a sequence encoding the VH comprising or consisting of the nucleic acid sequence as set forth in SEQ ID NO: 49 or a nucleic acid sequence sharing at least 70%, 75%, 80%, 85%, 90%, 95%, 96%, 97%, 98%, 99% or more of identity with SEQ ID NO: 49; and
- a sequence encoding the VL comprising or consisting of the nucleic acid sequence as set forth in SEQ ID NO: 55 or a nucleic acid sequence sharing at least 70%, 75%, 80%, 85%, 90%, 95%, 96%, 97%, 98%, 99% or more of identity with SEQ ID NO: 55.

In one embodiment, said nucleic acid encodes for the VH and VL of the INO-10-4 antibody or of the INO-10-F4 (or F4) Fab fragment.

In one embodiment, the nucleic acid according to the present invention comprises or consists of:

- a sequence encoding the VH comprising or consisting of the nucleic acid sequence as set forth in SEQ ID NO: 50 or a nucleic acid sequence sharing at least 70%, 75%, 80%, 85%, 90%, 95%, 96%, 97%, 98%, 99% or more of identity with SEQ ID NO: 50; and
- a sequence encoding the VL comprising or consisting of the nucleic acid sequence as set forth in SEQ ID NO: 56 or a nucleic acid sequence sharing at least 70%, 75%, 80%, 85%, 90%, 95%, 96%, 97%, 98%, 99% or more of identity with SEQ ID NO: 56.

In one embodiment, said nucleic acid encodes for the VH and VL of the INO-10-5 antibody or of the INO-10-F5 (or E5) Fab fragment.

In one embodiment, the nucleic acid according to the present invention comprises or consists of:

- a sequence encoding the VH comprising or consisting of the nucleic acid sequence as set forth in SEQ ID NO: 51 or a nucleic acid sequence sharing at least 70%, 75%, 80%, 85%, 90%, 95%, 96%, 97%, 98%, 99% or more of identity with SEQ ID NO: 51; and
- a sequence encoding the VL comprising or consisting of the nucleic acid sequence as set forth in SEQ ID NO: 57 or a nucleic acid sequence sharing at least 70%, 75%, 80%, 85%, 90%, 95%, 96%, 97%, 98%, 99% or more of identity with SEQ ID NO: 57.

In one embodiment, said nucleic acid encodes for the VH and VL of the INO-10-6 antibody or of the INO-10-F6 (or F6) Fab fragment.

In one embodiment, the nucleic acid according to the present invention comprises or consists of:

- a sequence encoding the VH comprising or consisting of the nucleic acid sequence as set forth in SEQ ID NO: 52 or a nucleic acid sequence sharing at least 70%, 75%, 80%, 85%, 90%, 95%, 96%, 97%, 98%, 99% or more of identity with SEQ ID NO: 52; and
- a sequence encoding the VL comprising or consisting of the nucleic acid sequence as set forth in SEQ ID NO: 58 or a nucleic acid sequence sharing at least 70%, 75%, 80%, 85%, 90%, 95%, 96%, 97%, 98%, 99% or more of identity with SEQ ID NO: 58.

In one embodiment, said nucleic acid encodes for the VH and VL of the INO-10-1 antibody or of the INO-10-F1 (or F1) Fab fragment.

Typically, the nucleic acid according to the present invention is a DNA or RNA molecule, which may be included in any suitable vector, such as for example a plasmid, a cosmid, an episome, an artificial chromosome, a phage or a viral vector.

Thus, another object of the present invention is a vector, such as, for example, an expression vector, comprising a nucleic acid encoding the antibody or antigen-binding fragment thereof according to the present invention. Another object of the present invention is a vector, such as, for example, an expression vector, comprising a nucleic acid encoding a fusion protein according to the present invention.

The terms "vector", "cloning vector" and "expression vector" mean the vehicle by which a DNA or RNA sequence (e.g., a foreign gene) can be introduced into a host cell, so as to transform the host cell and promote expression (e.g., transcription and translation) of the introduced sequence encoding an antibody or antigen-binding fragment thereof. Such vectors may comprise regulatory elements, such as a promoter, enhancer, terminator and the like, to cause or direct expression of said antibody or antigen-binding fragment thereof upon administration to a subject. Examples of promoters and enhancers used in expression vectors for animal cells include, but are not limited to, early promoter and enhancer of SV40, LTR promoter and enhancer of Moloney mouse leukemia virus, promoter and enhancer of immunoglobulin H chain and the like. Any expression vector for animal cells can be used, so long as a gene encoding the anti-hTREM-1 antibody or antigen-binding fragment thereof as described herein be inserted and expressed. Examples of suitable vectors include pAGE107, pAGE103, pHSG274, pKCR, pSG1 beta d2-4 and the like. Other examples of plasmids include replicating plasmids comprising an origin of replication, or integrative plasmids, such as for instance pUC, pcDNA, pBR, and the like. Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells.

In one embodiment, the vector or expression vector according to the present invention comprises a sequence encoding the heavy chain variable domain of the antibody or antigen-binding fragment thereof according to the present invention, operably linked to regulatory elements. In one embodiment, the vector or expression vector according to the present invention comprises a sequence encoding the light chain variable domain of the antibody or antigen-binding fragment thereof according to the present invention operably linked to regulatory elements.

In one embodiment, the expression vector according to the present invention is monocistronic. By "monocistronic", it is meant that a single nucleic acid is expressed in a single expression vector. In one embodiment, the expression vector according to the present invention is polycistronic. By "polycistronic", it is meant that at least two or more nucleic acids are expressed in a single expression vector.

Another object of the invention is an isolated host cell comprising said vector. Said host cell may be used for the recombinant production of the anti-hTREM-1 antibody or antigen-binding fragment thereof as described herein.

In an embodiment, host cells may be prokaryote cells, or eukaryote cells, such as, for example, yeast or mammalian cells. Examples of mammalian cells include, but are not limited to, monkey kidney CV1 line transformed by SV40 (COS-7, ATCC CRL 1651); human embryonic kidney line (293 or 293T cells sub); baby hamster kidney cells (BHK, ATCC CCL 10); Chinese hamster ovary cells/-DHFR (CHO); mouse Sertoli cells (TM4); mouse myeloma cells SP2/0-AG14 (ATCC CRL 1581; ATCC CRL 8287) or NSO (HPA culture collections no. 85110503); monkey kidney cells (CVl ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; as well as DSM's PERC-6 cell line. Expression vectors suitable for use in each of these host cells are also generally known in the art.

It should be noted that the term "host cell" generally refers to a cultured cell line. Whole human beings into which or vector or expression vector encoding an anti-hTREM-1 antibody or antigen-binding fragment thereof according to the invention has been introduced are explicitly excluded from the definition of a "host cell".

Another object of the present invention is a method of producing and purifying the isolated anti-hTREM-1 antibody or antigen-binding fragment thereof as described herein.

In one embodiment, the method comprises:

introducing in vitro or ex vivo a recombinant nucleic acid or a vector as described above into a competent host cell;

culturing in vitro or ex vivo host cells transformed with the nucleic acid or expression vector according to the present invention, under conditions suitable for expression of the anti-hTREM-1 antibody or antigen-binding fragment thereof;

optionally, selecting the cells which express and/or secrete said anti-hTREM-1 antibody or antigen-binding fragment thereof; and recovering the expressed anti-hTREM-1 antibody or antigen-binding fragment thereof.

This recombinant process is well-known in the art and can be used for large scale production of antibodies or antigen-binding fragments thereof, including monoclonal antibodies intended for in vitro, ex vivo and/or in vivo therapeutic uses.

In an embodiment, the expressed antibody or antigen-binding fragment thereof is further purified. Methods to purify the antibody or antigen-binding fragment thereof according to the present invention are well-known in the art and include, without limitation, use of an anti-CH1 antibody, protein A-Sepharose, gel electrophoresis, chromatography, in particular affinity chromatography.

Another object of the present invention is a composition comprising, consisting essentially of, or consisting of at least one antibody or antigen-binding fragment thereof according to the present invention.

Another object of the present invention is a composition comprising, consisting essentially of, or consisting of at least one fusion protein according to the present invention.

A further object of the present invention is a composition comprising, consisting essentially of, or consisting of at least one nucleic acid encoding an antibody or antigen-binding fragment thereof, or a fusion protein according to the present invention, or at least one vector comprising such a nucleic acid.

Another object of the present invention is a pharmaceutical composition comprising, consisting essentially of, or consisting of at least one antibody or antigen-binding fragment thereof according to the present invention, and at least one pharmaceutically acceptable excipient.

Another object of the present invention is a pharmaceutical composition comprising, consisting essentially of, or consisting of at least one fusion protein according to the present invention, and at least one pharmaceutically acceptable excipient.

A further object of the present invention is a pharmaceutical composition comprising, consisting essentially of, or consisting of at least one nucleic acid encoding an anti-hTREM-1 antibody or antigen-binding fragment thereof, or a fusion protein according to the present invention, or at least one vector comprising such a nucleic acid, and at least one pharmaceutically acceptable excipient.

As used herein, "consisting essentially of", with reference to a composition or pharmaceutical composition, means that the at least one antibody or antigen-binding fragment thereof, fusion protein, nucleic acid, or vector is the only therapeutic agent or agent with a biologic activity within said composition or pharmaceutical composition.

The term "pharmaceutically acceptable excipient" or "pharmaceutically acceptable carrier" includes any and all solvents, dispersion media, coatings, antibacterial and antifungal agents, isotonic and absorption delaying agents and the like. Said excipient or carrier does not produce an adverse, allergic or other untoward reaction when administered to a subject, preferably a human. A pharmaceutically acceptable excipient or carrier refers to a non-toxic solid, semi-solid or liquid filler, diluent, encapsulating material or formulation auxiliary of any type. For human administration, preparations should meet sterility, pyrogenicity, and general safety and purity standards as required by regulatory offices, such as, for example, the FDA (US Food and Drug Administration) or EMA (European Medicines Agency).

Pharmaceutically acceptable excipients or carriers that may be used in the composition or pharmaceutical composition include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, the pharmaceutical composition according to the present invention comprises vehicles which are pharmaceutically acceptable for a formulation adapted for being injected to a subject. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Another object of the present invention is a medicament comprising, consisting essentially of, or consisting of at least one antibody or antigen-binding fragment thereof according to the present invention.

Another object of the present invention is a medicament comprising, consisting essentially of, or consisting of at least one fusion protein according to the present invention.

A further object of the present invention is a medicament comprising, consisting essentially of, or consisting of at least one nucleic acid encoding an antibody or antigen-binding fragment thereof, or a fusion protein according to the present invention, or at least one vector comprising such a nucleic acid.

Another object of the invention is a kit comprising at least one antibody, or antigen-binding fragment thereof, or fusion protein according to the present invention and, optionally, instructions for use.

By "kit" is intended any manufacture (e.g., a package or a container) comprising at least one antibody, or antigen-binding fragment thereof, or fusion protein according to the present invention. The kit may be promoted, distributed, or sold as a unit for performing the methods as described herein.

Another object of the present invention is an antibody or antigen-binding fragment thereof according to the present invention for use as a medicament.

Another object of the present invention is a fusion protein according to the present invention for use as a medicament.

A further object of the present invention is a nucleic acid encoding an antibody or antigen-binding fragment thereof, or a fusion protein according to the present invention, or a vector comprising such a nucleic acid, for use as a medicament.

A further object of the present invention is a composition, pharmaceutical composition or medicament as described herein, for use as a medicament.

For use in a subject in need thereof, the composition, pharmaceutical composition or medicament will be formulated for administration to the subject. The composition, pharmaceutical composition or medicament according to the present invention may be administered parenterally, by injection, by infusion, by inhalation spray, orally, rectally, nasally, topically, or via an implanted reservoir. The term administration used herein thus includes subcutaneous, intravenous, intramuscular, intra-articular, intra-synovial, intrasternal, intrathecal, intrahepatic, intralesional and intracranial injection or infusion techniques.

Examples of forms adapted for injection include, but are not limited to, solutions, such as, for example, sterile aqueous solutions, gels, dispersions, emulsions, suspensions, solid forms suitable for using to prepare solutions or suspensions upon the addition of a liquid prior to use, such as, for example, powder, liposomal forms and the like.

In one embodiment, the antibody or antigen-binding fragment thereof, the fusion protein, nucleic acid, vector, composition, pharmaceutical composition or medicament according to the present invention is for administration to a subject in need thereof in a therapeutically effective amount or dose.

It will be understood that the total daily usage of the antibody or antigen-binding fragment thereof, fusion protein, nucleic acid, expression vector, composition, pharmaceutical composition or medicament according to the present invention will be decided by the attending physician within the scope of sound medical judgment. The specific therapeutically effective amount or dose for any particular subject will depend upon a variety of factors including the disease being treated and the severity of the disease; activity of the antibody or antigen-binding fragment thereof, fusion protein, nucleic acid, vector, composition, pharmaceutical composition or medicament employed; the age, body weight, general health, sex and diet of the subject; the time of administration, route of administration, and rate of excretion of the specific antibody or antigen-binding fragment thereof, fusion protein, nucleic acid, expression vector, composition, pharmaceutical composition or medicament employed; the duration of the treatment; drugs used in combination or coincidental with the specific antibody or antigen-binding fragment thereof, fusion protein, nucleic acid, vector, composition, pharmaceutical composition or medicament employed; and like factors well known in the medical arts. For example, it is well within the skill of the art to start doses of the therapeutic agent at levels lower than those required to achieve the desired therapeutic effect and to gradually increase the dosage until the desired effect is achieved. The total dose required for each treatment may be administered by multiple doses or in a single dose.

In one embodiment, regimens or dosages used for administration of the antibody, antigen-binding fragment thereof, or fusion protein can be adapted as function of various parameters, and in particular as a function of the mode of administration used, of the relevant pathology, or of the desired duration of treatment. For example, it is well within the skill of the art to start doses of the antibody, antigen-binding fragment thereof, or fusion protein at levels lower than those required to achieve the desired therapeutic effect and to gradually increase the dosage until the desired effect is achieved. The daily dosage of the antibody, antigen-binding fragment, or fusion protein may be varied over a wide range from 0.01 to 1000 mg per adult per day. Compositions, pharmaceutical compositions or medicaments may contain 0.01, 0.05, 0.1, 0.5, 1.0, 2.5, 5.0, 10.0, 15.0, 25.0, 50.0, 100, 250, and 500 mg of the therapeutic agent for the symptomatic adjustment of the dosage to the subject to be treated. A composition, pharmaceutical composition, or medicament typically may for example comprise from about 0.01 mg to about 500 mg of therapeutic agent. A therapeutically effective amount of the therapeutic agent may for example be supplied at a dosage level from 0.0002 mg/kg to about 20 mg/kg of body weight per day. For example, an antibody, antigen-binding fragment thereof, or fusion protein present in a composition, pharmaceutical composition or medicament as described hereinabove can be supplied at a concentration ranging from 1 mg/mL to about 100 mg/mL, such as, for example, at a concentration of 1 mg/mL, 5 mg/mL, 10 mg/mL, 50 mg/mL or 100 mg/mL. In one embodiment, the antibody, antigen-binding fragment thereof, or fusion protein is supplied at a concentration of about 10 mg/mL in either 100 mg (10 mL) or 500 mg (50 mL) single use-vials. It will be appreciated that these dosages are exemplary and that an optimal dosage can be adapted taking into account the affinity and tolerability of the particular antibody, antigen-binding fragment thereof, or fusion protein in the composition, pharmaceutical composition, or medicament that must be determined in clinical trials.

The present invention relates to an antibody, or antigen-binding fragment thereof, or fusion protein as described herein for treating (or for use in treating or for use in the treatment of) a disease selected from an inflammatory or autoimmune disease; a cardiovascular disease; a cancer, in particular a solid cancer; and an infectious disease, in particular a bacterial infection or a viral infection in a subject in need thereof.

The present invention also relates to a nucleic acid encoding an antibody, or antigen-binding fragment thereof, or fusion protein as described herein, or to a vector comprising said nucleic acid as described herein, for treating (or for use in treating or for use in the treatment of) a disease selected from an inflammatory or autoimmune disease; a cardiovascular disease; a cancer, in particular a solid cancer; and an infectious disease, in particular a bacterial infection or a viral infection in a subject in need thereof.

The present invention further relates to a composition, pharmaceutical composition, or medicament as described herein, for treating (or for use in treating or for use in the treatment of) a disease selected from an inflammatory or autoimmune disease; a cardiovascular disease; a cancer, in particular a solid cancer; and an infectious disease, in particular a bacterial infection or a viral infection in a subject in need thereof.

The present invention relates to a method for treating a disease selected from an inflammatory or autoimmune disease; a cardiovascular disease; a cancer, in particular a solid cancer; and an infectious disease, in particular a bacterial infection or a viral infection, in a subject in need thereof, wherein said method comprises administering to the subject at least one isolated antibody, or antigen-binding fragment thereof, or fusion protein, as described herein.

The present invention also relates to a method for treating a disease selected from an inflammatory or autoimmune disease; a cardiovascular disease; a cancer, in particular a solid cancer; and an infectious disease, in particular a bacterial infection or a viral infection, in a subject in need thereof, wherein said method comprises administering to the subject at least one nucleic acid encoding an antibody, or antigen-binding fragment thereof, or fusion protein as described herein or a least one vector comprising said nucleic acid as described herein.

The present invention further relates to a method for treating a disease selected from an inflammatory or autoimmune disease; a cardiovascular disease; a cancer, in particular a solid cancer; and an infectious disease, in particular a bacterial infection or a viral infection, in a subject in need thereof, wherein said method comprises administering to the subject a composition, pharmaceutical composition or medicament as described herein.

The present invention further relates to a pharmaceutical composition for treating (or for use in treating or for use in the treatment of) a disease selected from an inflammatory or autoimmune disease; a cardiovascular disease; a cancer, in particular a solid cancer; and an infectious disease, in particular a bacterial infection or a viral infection, in a subject in need thereof, wherein said pharmaceutical composition comprises at least one of:

- an antibody or antigen-binding fragment thereof according, as described herein;
- a fusion protein as described herein;
- a nucleic acid encoding an antibody, or antigen-binding fragment thereof, or fusion protein as described herein; or
- a vector comprising such a nucleic acid;

and optionally at least one pharmaceutically acceptable excipient.

The present invention further relates to the use of an antibody, or antigen-binding fragment thereof, or fusion protein as described herein, for the manufacture of a medicament for treating a disease selected from an inflammatory or autoimmune disease; a cardiovascular disease; a cancer, in particular a solid cancer; and an infectious disease, in particular a bacterial infection or a viral infection, in a subject in need thereof.

The present invention further relates to the use of a nucleic acid encoding an antibody, or antigen-binding fragment thereof, or fusion protein as described herein, or of a vector comprising such a nucleic acid, for the manufacture of a medicament for treating a disease selected from an inflammatory or autoimmune disease; a cardiovascular disease; a cancer, in particular a solid cancer; and an infectious disease, in particular a bacterial infection or a viral infection, in a subject in need thereof.

In one embodiment, the disease to be treated is an inflammatory disease. As used herein the term "inflammatory diseases" refers to disorders and conditions that are characterized by the presence of inflammation. Symptoms of inflammation can include chronic pain, swelling, redness, joint and muscle stiffness, loss of function and movement in the affected area. Examples of inflammatory diseases include inflammatory bowel disease (IBD), Crohn's disease, rheumatoid arthritis, psoriasis, systemic lupus erythematosus, vasculitis, sepsis, systemic inflammatory response syndrome (SIRS), multiple sclerosis, coronary artery disease, chronic obstructive pulmonary disease, interstitial lung disease, chronic inflammatory demyelinating polyneuropathy, and asthma. In one embodiment, the inflammatory disease is a connective tissue disease or disorder. Examples of inflammatory connective tissue diseases or disorders include rheumatoid arthritis, scleroderma and lupus.

In one embodiment, the disease to be treated is an autoimmune disease. Examples of autoimmune diseases include inflammatory bowel disease (IBD), rheumatoid arthritis, psoriasis, systemic lupus erythematosus, vasculitis, type I diabetes, Grave's disease, multiple sclerosis, and autoimmune myocarditis.

In one embodiment, the disease to be treated is an inflammatory or autoimmune disease.

In one embodiment, said inflammatory or autoimmune disease is selected from an inflammatory bowel disease (IBD) (including ALPI-related IBD, monogenic very early onset IBD), Crohn's disease, ulcerative colitis, irritable bowel syndrome, fibroses such as pulmonary fibrosis or liver fibrosis, rheumatoid arthritis, juvenile idiopathic arthritis, psoriasis, psoriatic arthritis, systemic lupus erythematosus, lupus nephritis, vasculitis, nonalcoholic fatty liver disease (NAFLD), non-alcoholic steatohepatitis (NASH), alcoholic hepatitis, systemic inflammatory response syndrome (SIRS), sepsis, septic shock, type I diabetes, Grave's disease, multiple sclerosis, autoimmune myocarditis, Kawasaki disease, coronary artery disease, chronic obstructive pulmonary disease, interstitial lung disease, autoimmune thyroiditis, scleroderma, systemic sclerosis, osteoarthritis, spondylitis, ankylosing spondylitis, atopic dermatitis, vitiligo, macular degeneration, retinal degeneration, uveitis, hidradenitis suppurativa, gingival inflammation and diseases, graft versus host disease, Sjogren's syndrome, autoimmune nephritis, Goodpasture's syndrome, chronic inflammatory demyelinating polyneuropathy, allergy, and asthma. As used herein, "inflammatory bowel disease (IBD)" encompasses monogenic polygenic IBD, monogenic IBD, very early onset IBD, early onset IBD, and IBD refractory to treatment.

In one embodiment, said inflammatory or autoimmune disease is selected from an inflammatory bowel disease (IBD), Crohn's disease, ulcerative colitis, irritable bowel syndrome, fibrosis, pulmonary fibrosis, liver fibrosis, nonalcoholic steatohepatitis (NASH), alcoholic hepatitis, rheumatoid arthritis, psoriasis, psoriatic arthritis, systemic lupus erythematosus, lupus nephritis, vasculitis, systemic inflammatory response syndrome (SIRS), sepsis, septic shock, type I diabetes, Grave's disease, multiple sclerosis, autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture's syndrome, chronic inflammatory demyelinating polyneuropathy, allergy, and asthma.

In one embodiment, said inflammatory or autoimmune disease is selected from an inflammatory bowel disease (IBD), Crohn's disease, ulcerative colitis, irritable bowel syndrome, rheumatoid arthritis, psoriasis, psoriatic arthritis, systemic lupus erythematosus, lupus nephritis, vasculitis, systemic inflammatory response syndrome (SIRS), sepsis, septic shock, type I diabetes, Grave's disease, multiple sclerosis, autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture's syndrome, chronic inflammatory demyelinating polyneuropathy, allergy, and asthma.

In one embodiment, the disease to be treated is a cardiovascular disease. Examples of cardiovascular diseases include myocardial infarction, acute myocardial infarction, cerebral infarction, ischemia, coronary heart disease, acute coronary syndrome, stroke, aneurysm, stable angina pectoris, effort angina pectoris, cardiomyopathy, hypertensive heart disease, chronic heart failure, acute heart failure, cor pulmonale, cardiac dysrhythmias, inflammatory heart diseases (such as endocarditis and myocarditis), vasculitis, peripheral arterial disease, SIRS-associated myocardial and vascular dysfunction, atherosclerosis.

In one embodiment, the disease to be treated is a cancer. As used herein the term "cancer" generally refers to a disease caused by an uncontrolled division of abnormal cells. The term "cancer" in particular refers to any disease associated with tumorigenesis. The term "cancer" encompasses solid tumors and blood cancers, and encompasses both primary and metastatic cancers. Examples of cancers include carcinomas, adenocarcinomas, soft tissue cancers, sarcomas, teratomas, melanomas, leukemias, Hodgkin lymphoma, non-Hodgkin lymphomas, and brain cancers. In one embodiment, the cancer is immunoevasive. In one embodiment, the cancer is immunoresponsive. In one embodiment, the cancer is melanoma, kidney or renal cancer, hepatobiliary cancer, head-neck squamous carcinoma (HNSC), pancreatic cancer, colon cancer, bladder cancer, urothelial cancer, glioblastoma cancer, prostate cancer, lung cancer, breast (mammary) cancer, ovarian cancer, gastric cancer, esophageal cancer, endometrial cancer, cervical cancer, testicular cancer, leukemia, lymphoma, or mesothelioma. In one embodiment, the cancer is colon cancer, pancreatic cancer, or breast cancer.

In one embodiment, the disease to be treated is an infectious disease. As used herein the term "infectious disease" refers to a pathological condition or disorder resulting from an infection. Examples of infectious diseases include bacterial diseases (or bacterial infections), viral diseases (or viral infections), fungal diseases (or fungal infections), and parasitic diseases (or parasitic infections), which are infectious diseases caused by bacteria, viruses, fungi, and parasites, respectively. Examples of bacterial diseases include *Escherichia coli* infections.

In one embodiment, the disease to be treated is selected from the group comprising or consisting of aneurysm, Still's disease (in particular adult-onset Still's disease or AOSD), burns, cytokine release syndrome (CRS) following CAR-T cells therapy, immune effector cell-associated neurotoxicity syndrome (ICANS) following CAR-T cells therapy, cystic fibrosis, endometritis, familial Mediterranean fever, gout, hepatic granuloma, idiopathic granulomatous mastitis, kidney diseases (including sterile chronic kidney injury, nephropathies), liver diseases (non-alcoholic steatohepatitis (NASH), alcoholic hepatitis), lung diseases (acute respiratory distress syndrome (ARDS), sarcoidosis), obesity (and related diseases), pancreatitis, Alzheimer's disease, Parkinson disease, stroke, trauma, and cardiovascular diseases (CVDs).

In one embodiment, the disease to be treated is inflammatory bowel disease (IBD), ALPI-related IBD, monogenic very early onset IBD, Crohn's disease, or ulcerative colitis.

In one embodiment, the antibody, antigen-binding fragment thereof, fusion protein, nucleic acid, vector, composition, pharmaceutical composition or medicament as described herein is to be administered, for administration, or adapted for administration with at least one further therapeutically active agent or therapy. The antibody, antigen-binding fragment thereof, fusion protein, nucleic acid, vector, composition, pharmaceutical composition or medicament as described herein may be administered simultaneously, separately or sequentially with said at least one further therapeutically active agent or therapy. In one embodiment, the antibody, antigen-binding fragment thereof, fusion protein, nucleic acid, vector medicament as described herein is to be administered, for administration, or adapted for administration in combination with at least one further therapeutically active agent or therapy, such as in a combined preparation, composition, pharmaceutical composition or medicament.

Examples of therapeutically active agents that may be used with the antibody, antigen-binding fragment thereof, fusion protein, nucleic acid, vector, composition, pharmaceutical composition or medicament as described herein include anti-TNFα (such as adalimumab, etanercept, infliximab, or certolizumab), anti-interleukin (IL)-12/23 (such as ustekinumab), anti-integrins (such as vedolizumab or natalizumab), JAK inhibitors (such as tofacitinib, baricitinib, or filgotinib), anti-PD-1 antibodies (such as pembrolizumab, nivolumab, or cemiplimab), anti-PD-L1 antibodies (such as durvalumab, avelumab, or atezolizumab), anti-PD-L2 antibodies, and anti-CTLA-4 antibodies (such as ipilimumab).

Examples of therapies that may be used with the antibody, antigen-binding fragment thereof, fusion protein, nucleic acid, vector, composition, pharmaceutical composition or medicament as described herein include PD-1/PD-L1/PD-L2 blockade therapy, CTLA4 blockade therapy, generalized checkpoint blockade therapy in which inhibitory molecules on T cells are blocked, adoptive T-cell therapy, CAR T-cell therapy, cellular therapies such as dendritic cell therapy, and chemotherapies.

In one embodiment, the disease to be treated is an inflammatory disease as described above, for example inflammatory bowel disease (IBD) as described above or rheumatoid arthritis, and the antibody, antigen-binding fragment thereof, fusion protein, nucleic acid, vector, composition, pharmaceutical composition or medicament as described herein is to be administered, for administration, or adapted for administration with at least one further therapeutically active agent selected from the group comprising or consisting of anti-TNFα, anti-IL-12/23, anti-integrins, and JAK inhibitors.

In one embodiment, the disease to be treated is a cancer as described above and the antibody, antigen-binding fragment thereof, fusion protein, nucleic acid, vector, composition, pharmaceutical composition or medicament as described herein is to be administered, for administration, or adapted for administration with at least one further therapeutically active agent or therapy selected from the group comprising or consisting of PD-1/PD-L1/PD-L2 blockade therapy, anti-PD-1 antibodies, anti-PD-L1 antibodies, anti-PD-L2 antibodies, CTLA4 blockade therapy, anti-CTLA-4 antibodies, generalized checkpoint blockade therapy in which inhibitory molecules on T cells are blocked, adoptive T-cell therapy, CAR T-cell therapy, cellular therapies such as dendritic cell therapy, and chemotherapies.

In one embodiment, the subject in need of treatment is identified or selected following the measure of his/her level of TREM-1, in particular of soluble TREM-1 (sTREM-1), in a biological sample.

In one embodiment, the subject in need of treatment is monitored through the measure of his/her level of TREM-1, in particular of sTREM-1, in a biological sample. Said monitoring may encompass the monitoring of the progression of the disease in the subject, the monitoring of the response of the subject to the treatment (i.e., response to the antibody, antigen-binding fragment thereof, fusion protein, nucleic acid, vector, composition, pharmaceutical composition or medicament as described herein), and/or the monitoring of the efficacy of the treatment in the subject (i.e., efficacy of the antibody, antigen-binding fragment thereof, fusion protein, nucleic acid, vector, composition, pharmaceutical composition or medicament as described herein).

As used herein, "sTREM-1", for "soluble triggering receptor expressed on myeloid cells-1", refers to a soluble form of TREM-1 lacking the transmembrane and intracellular domains of TREM-1. In one embodiment, sTREM-1 thus corresponds to the soluble form of the extracellular domain of TREM-1. In one embodiment, sTREM-1 corresponds to a truncated TREM-1 shed from the membrane of myeloid cells, in particular from activated myeloid cells. In one embodiment, sTREM-1 has an amino acid sequence corresponding to amino acids 21 to 205 of SEQ ID NO: 43. In one embodiment, sTREM-1 has an amino acid sequence corresponding to amino acids 31 to 205 of SEQ ID NO: 43. In one embodiment, sTREM-1 comprises an amino acid sequence corresponding to amino acids 31 to 137 of SEQ ID NO: 43, and has a length of 200 amino acids or less, preferably of 185 amino acids or less.

As used herein, "biological sample" refers to a biological sample isolated, collected or harvested from a subject and can include, bodily fluids, cell samples and/or tissue extracts such as homogenates or solubilized tissues obtained from a subject. In one embodiment, the present invention does not comprise obtaining a biological sample from a subject. Thus, in one embodiment, the biological sample from the subject is a biological sample previously obtained from the subject. Said biological sample may be conserved in adequate conditions before being used as described herein. In one embodiment, the biological sample from the subject is a body fluid sample. Examples of body fluids include blood, plasma, serum, lymph, saliva, urine, bronchioalveolar lavage fluid, cerebrospinal fluid, sweat or any other bodily secretion or derivative thereof.

As used herein, the term "measure" is interchangeable with the terms "measurement" or "detection", and means assessing the presence, absence, quantity, or amount (which can be an effective amount) of a given substance, i.e., TREM-1 or sTREM-1, within a biological sample from a subject. "Measure" as used herein include the derivation of the qualitative or quantitative concentration of said substance, i.e., TREM-1 or sTREM-1, within the biological sample and within the subject (e.g., blood concentration or plasma concentration). As used herein, the term "level" as in "TREM-1 level", and in particular "sTREM-1 level", refers to the quantity, amount, or concentration of TREM 1, in particular of sTREM-1.

The level of TREM-1, in particular of sTREM-1, may be measured by any known method in the art. Methods for measuring an expression level such as a transcription level or a translation level are well-known to the skilled artisan.

Methods for measuring the transcription level of TREM-1, in particular of sTREM-1, (i.e., the level of TREM-1 mRNA or cDNA, in particular of sTREM-1 mRNA or cDNA) in a biological sample as described hereinabove are well-known to the skilled artisan and include, without being limited to, PCR, qPCR, RT-PCR, RT-qPCR, northern blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing").

Methods for measuring the translation level of TREM-1, in particular of sTREM-1, (i.e., the level of TREM-1 protein or of sTREM-1 protein) are well-known to the skilled artisan and include, without being limited to, immunohistochemistry, multiplex methods (such as Luminex®), immunoassays, western blot, enzyme-linked immunosorbent assay (ELISA), sandwich ELISA, multiplex ELISA, capillary-based ELISA (such as the ELLA® platform), electrochemiluminescence (ECL) also referred as electrogenerated chemiluminescence or electrochemiluminescence immunoassay (ECLIA), enzyme-linked fluorescent assay (ELFA), fluorescent-linked immunosorbent assay (FLISA), enzyme immunoassay (EIA), radioimmunoassay (RIA), flow cytometry (FACS), surface plasmon resonance (SPR), biolayer interferometry (BLI), immunochromatographic assay (ICA) (such as NEXUS IB10, Sphingotech) and mass spectrometry-based approaches.

The following sequences are listed herein:

SEQ ID NO: 1:
NTYIH;

SEQ ID NO: 2:
RIDPA$X_1$G$X_2$TKY$X_3$PKV$X_4$G, wherein $X_1$ is N or G, $X_2$ is N or R, $X_3$ is A, D, or S, $X_4$ is Q or K;

SEQ ID NO: 3:
H$X_5$G$X_6$TMDY, wherein $X_5$ is Y or R, $X_6$ is S or G;

SEQ ID NO: 4: RAS$X_7$SV$X_8$NYGISF$X_9$N, wherein $X_7$ is E or Q, $X_8$ is D or S, $X_9$ is M or L;

SEQ ID NO: 5: AA$X_{10}X_{11}X_{12}X_{13}X_{14}$, wherein $X_{10}$ is S or E, $X_{11}$ is N or Y, $X_{12}$ is Q or R, $X_{13}$ is G, A, or K, $X_{14}$ is S or R;

SEQ ID NO: 6: QQS$X_{15}X_{16}X_{17}$P$X_{18}$T, wherein $X_{15}$ is K, R, or S, $X_{16}$ is E, H, or N, $X_{17}$ is V or F, $X_{18}$ is W or Y;

SEQ ID NO: 7:
RIDPAGGRTKYDPKVKG;

SEQ ID NO: 8:
HYGGTMDY;

SEQ ID NO: 9:
RASESVDNYGISFLN;

SEQ ID NO: 10:
AAEYRGR;

SEQ ID NO: 11:
QQSRHVPYT;

SEQ ID NO: 12:
RIDPAGGRTKYSPKVQG;

SEQ ID NO: 13:
HRGGTMDY;

SEQ ID NO: 14:
RASQSVSNYGISFLN;

SEQ ID NO: 15:
AASYQKR;

SEQ ID NO: 16:
QQSSNFPWT;

SEQ ID NO: 17:
RIDPAGGRTKYAPKVKG;

SEQ ID NO: 18:
QQSSNVPYT;

SEQ ID NO: 19:
RIDPAGGRTKYAPKVQG;

SEQ ID NO: 20:
AAEYQGR;

SEQ ID NO: 21:
AAEYRAR;

SEQ ID NO: 22:
RIDPANGNTKYAPKVQG;

SEQ ID NO: 23:
HYGSTMDY;

-continued

SEQ ID NO: 24:
RASESVDNYGISFMN;

SEQ ID NO: 25:
AASNQGS;

SEQ ID NO: 26:
QQSKEVPWT;

SEQ ID NO: 27:
EVQLVESGGALVKPGGSLRLSCAASGFNIDNTYIHWVR
QAPGKGLEWIGRIDPAGGRTKYDPKVKGRFTISADTSKNTAYLQMNSLKTEDTA
VYYCTGHYGGTMDYWGQGTLVTVSS;

SEQ ID NO: 28:
EVQLVESGGALVKPGGSLRLSCAASGFNIGNTYIHWVR
QAPGKGLEWIGRIDPAGGRTKYSPKVQGRFTISAPTSKNTAYLQMNSLKTEDTAV
YYCTGHRGGTMDYWGQGTLVTVSS;

SEQ ID NO: 29:
EVQLVESGGALVKPGGSLRLSCAASGFNIGNTYIHWVR
QAPGKGLEWVGRIDPAGGRTKYAPKVKGRFTISADDSKNTAYLQMNSLKTEDT
AVYYCTGHRGGTMDYWGQGTLVTVSS;

SEQ ID NO: 30:
EVQLVESGGALVKPGGSLRLSCAASGFNIGNTYIHWVR
QAPGKGLEWIGRIDPAGGRTKYAPKVQGRFTISADTSKNTAYLQMNSLKTEDTA
VYYCTGHYGGTMDYWGQGTLVTVSS;

SEQ ID NO: 31:
EVQLVESGGALVKPGGSLRLSCAASGFNIGNTYIHWVR
QAPGKGLEWVGRIDPAGGRTKYAPKVKGRFTISADDSKNTLYLQMNSLKTEDTA
VYYCTGHRGGTMDYWGQGTLVTVSS;

SEQ ID NO: 32:
EVQLVESGGALVKPGGSLRLSCAASGFNIKNTYIHWVR
QAPGKGLEWIGRIDPANGNTKYAPKVQGRFTISADTSKNTAYLQMNSLKTEDTA
VYYCTGHYGSTMDYWGQGTLVTVSS;

SEQ ID NO: 33:
EIVLTQSPATLSLSPGERATLSCRASESVDNYGISFLNWY
QQKPGQAPRLLIYAAEYRGRGIPARFSGSGSGTDFTLTISSLEPEDFAVYYCQQSR
HVPYTFGQGTKVEIK;

SEQ ID NO: 34:
EIVLTQSPATLSLSPGERATLSCRASQSVSNYGISFLNWY
QQKPGQAPRLLIYAASYQKRGIPARFSGSGSGTDFTLTISSLEPEDFAVYYCQQSS
NFPWTFGQGTKVEIK;

SEQ ID NO: 35:
EIVLTQSPATLSLSPGERATLSCRASQSVSNYGISFLNWY
QQKPGQAPRLLIYAAEYRGRGIPARFSGSGSGTDFTLTISSLEPEDFAVYYCQQSS
NVPYTFGQGTKVEIK;

SEQ ID NO: 36:
EIVLTQSPATLSLSPGERATLSCRASQSVSNYGISFLNWY
QQKPGQAPRLLIYAAEYQGRGIPARFSGSGSGTDFTLTISSLEPEDFAVYYCQQSS
NVPYTFGQGTKLEIK;

SEQ ID NO: 37:
EIVLTQSPATLSLSPGERATLSCRASQSVSNYGISFLNWY
QQKPGQAPRLLIYAAEYRARGIPARFSGSGSGTDFTLTISSLEPEDFAVYYCQQSS
NVPYTFGQGTKVEIK;

SEQ ID NO: 38:
EIVLTQSPATLSLSPGERATLSCRASESVDNYGISFMNWF
QQKPGQAPRLLIYAASNQGSGIPARFSGSGSGTDFTLTISSLEPEDFAVYFCQQSKE
VPWTFGQGTKVEIK;

SEQ ID NO: 39:
RIDPA$X_1$G$X_2$TKY$X_3$PKF$X_4$G, wherein $X_1$ is N or G, $X_2$ is N or R, $X_3$ is A, D, or S, $X_4$ is Q or K;

SEQ ID NO: 40:
RIDPANGNTKYAPKFQG;

SEQ ID NO: 41:
AVQLQQSVAALVRPGASVKLSCTASGFNIKNTYIHWVK
QRPEQGLEWIGRIDPANGNTKYAPKFQGKATITADTSSDTAYLQLSSLTSDDTAIY
YCTGHYGSTMDYWGQGTSVTVSS;

-continued

SEQ ID NO: 42:
EIVLTQSPASLAVSLGQRATISCRASESVDNYGISFMNWF
QQKPGQTPKLLIYAASNQGSGVPARFSGSGSGTDFSLNIHPMEDDDTAMYFCQQS
KEVPWTFGGGTKLEIK;

SEQ ID NO: 43:
MRKTRLWGLLWMLFVSELRAATKLTEEKYELKEGQTL

DVKCDYTLEKFASSQKAWQIIRDGEMPKTLACTERPSKNSHPVQVGRIILEDYHD

HGLLRVRMVNLQVEDSGLYQCVIYQPPKEPHMLFDRIRLVVTKGFSGTPGSNEN

STQNVYKIPPTTTKALCPLYTSPRTVTQAPPKSTADVSTPDSEINLTNVTDIIRVPV

FNIVILLAGGFLSKSLVFSVLFAVTLRSFVP;

SEQ ID NO: 44:
MRKTRLWGLLWMLFVSELRAATKLTEEKYELKEGQTLD

VKCDYTLEKFASSQKAWQIIRDGEMPKTLACTERPSKNSHPVQVGRIILEDYHDH

GLLRVRMVNLQVEDSGLYQCVIYQPPKEPHMLFDRIRLVVTKGFRCSTLSFSWL

VDS;

SEQ ID NO: 45:
MRKTRLWGLLWMLFVSELRAATKLTEEKYELKEGQTLDV

KCDYTLEKFASSQKAWQIIRDGEMPKTLACTERPSKNSHPVQVGRIILEDYHDHG

LLRVRMVNLQVEDSGLYQCVIYQPPKEPHMLFDRIRLVVTKGFSGTPGSNENSTQ

NVYKIPPTTTKALCPLYTSPRTVTQAPPKSTADVSTPDSEINLTNVTDIIRYSFQVP

GPLVWTLSPLFPSLCAERM;

SEQ ID NO: 46:
MRKTRLWGLLWMLFVSELRAATKLTEEKYELKEGQTL

DVKCDYTLEKFASSQKAWQIIRDGEMPKTLACTERPSKNSHPVQVGRIILEDYHD

HGLLRVRMVNLQVEDSGLYQCVIYQPPKEPHMLFDRIRLVVTKGFSGTPGSNEN

STQNVYKIPPTTTKALCPLYTSPRTVTQAPPKSTADVSTPDSEINLTNVTDIIREKS

MTFGIRRLDVESHPLPPLHTGHFRISQFFSQAGTQSLHSCYKGKPTP;

SEQ ID NO: 47:
GAGGTGCAGCTGGTGGAGTCTGGAGGCGCTCTCGTGA

AGCCTGGCGGCTCTCTCAGACTCTCTTGCGCTGCCTCCGGCTTCAACATCGAC

AACACCTACATCCACTGGGTGCGGCAGGCTCCTGGAAAGGGACTCGAGTGGA

TCGGAAGAATCGACCCTGCTGGAGGGAGAACCAAGTACGACCCCAAGGTCA

AGGGGCGGTTCACCATCTCTGCCGACACCTCCAAGAACACCGCCTACCTGCA

GATGAACAGCCTCAAGACCGAGGACACCGCTGTCTACTACTGCACCGGGCAC

TACGGAGGGACAATGGATTACTGGGGACAGGGGACACTCGTCACCGTCTCTA

GC;

SEQ ID NO: 48:
GAGGTGCAGCTGGTGGAGTCTGGAGGCGCTCTCGTGA

AGCCTGGCGGCTCTCTCAGACTCTCTTGCGCTGCCTCCGGCTTCAACATCGGA

AACACCTACATCCACTGGGTGCGGCAGGCTCCTGGAAAGGGACTCGAGTGGA

TCGGAAGAATCGACCCTGCTGGAGGGAGAACCAAGTACTCCCCAAAGGTCCA

GGGGCGGTTCACCATCTCTGCCCCTACCTCCAAGAACACCGCCTACCTGCAGA

TGAACAGCCTCAAGACCGAGGACACCGCTGTCTACTACTGTACCGGGCACAG

GGGAGGGACAATGGATTACTGGGGACAGGGGACACTCGTCACCGTCTCTAGC

-continued

SEQ ID NO: 49:
GAGGTGCAGCTGGTGGAGTCTGGAGGCGCTCTGGTGAA

GCCTGGCGGCTCTCTGAGACTGTCTTGCGCTGCCTCCGGCTTCAACATCGGCA

ACACCTACATCCACTGGGTGCGGCAGGCTCCTGGAAAGGGACTGGAGTGGGT

GGGCAGAATCGATCCTGCTGGCGGAAGAACCAAGTACGCCCCAAAGGTGAA

GGGACGGTTCACCATCTCTGCCGACGACTCCAAGAACACCGCCTACCTCCAG

ATGAACTCCCTCAAGACCGAGGACACCGCTGTGTACTACTGTACCGGACACC

GGGGAGGGACAATGGATTACTGGGGACAGGGGACACTCGTGACCGTGTCTTC

C;

SEQ ID NO: 50:
GAGGTGCAGCTGGTGGAGTCTGGAGGCGCTCTGGTGA

AGCCTGGCGGCTCTCTGAGACTGTCTTGCGCTGCCTCCGGCTTCAACATCGGC

AACACCTACATCCACTGGGTGCGGCAGGCTCCTGGAAAGGGACTGGAGTGGA

TCGGCAGAATCGACCCTGCTGGCGGAAGAACCAAGTACGCCCCAAAGGTGCA

GGGACGGTTCACCATCTCTGCCGACACCTCCAAGAACACCGCCTACCTCCAG

ATGAACTCCCTCAAGACCGAGGACACCGCCGTGTACTACTGCACCGGACACT

ACGGAGGGACAATGGATTACTGGGGACAGGGGACACTCGTGACCGTGTCTTC

C;

SEQ ID NO: 51:
GAGGTGCAGCTGGTGGAGTCTGGAGGCGCTCTGGTGA

AGCCTGGCGGCTCTCTCAGACTCTCTTGCGCTGCCTCCGGCTTCAACATCGGA

AACACCTACATCCACTGGGTGCGGCAGGCTCCTGGAAAGGGACTCGAGTGGG

TCGGAAGAATCGATCCTGCTGGAGGGAGAACCAAGTACGCCCCAAAGGTCAA

GGGGCGGTTCACCATCTCTGCCGACGACTCCAAGAACACCCTGTACCTCCAG

ATGAACAGCCTCAAGACCGAGGACACCGCTGTCTACTACTGTACCGGGCACA

GGGGAGGGACAATGGATTACTGGGGACAGGGGACACTCGTCACCGTCTCTAG

C;

SEQ ID NO: 52:
GAGGTGCAGCTGGTGGAGTCTGGAGGCGCTCTGGTGA

AGCCTGGCGGCTCTCTGAGACTGTCTTGCGCTGCCTCCGGCTTCAACATCAAG

AACACCTACATCCACTGGGTGCGGCAGGCTCCTGGAAAGGGACTGGAGTGGA

TCGGCCGGATCGACCCTGCTAACGGCAACACCAAGTACGCCCCAAAGGTGCA

GGGACGGTTCACCATCTCTGCCGACACCTCCAAGAACACCGCCTACCTCCAG

ATGAACTCCCTCAAGACCGAGGACACCGCCGTGTACTACTGCACCGGACACT

ACGGATCCACCATGGACTACTGGGGACAGGGGACACTCGTGACCGTGTCTTC

C;

SEQ ID NO: 53:
GAGATCGTCCTGACCCAGTCTCCTGCCACCCTGTCTCT

CTCTCCCGGCGAAAGAGCCACCCTCTCTTGCAGAGCCTCCGAGTCCGTGGAC

AACTACGGCATCTCCTTCCTCAACTGGTACCAACAGAAGCCTGGACAGGCCC

CTAGGCTCCTCATCTACGCTGCTGAGTACAGGGGAAGGGGAATCCCCGCTAG

GTTCTCTGGGAGTGGGTCTGGGACCGACTTCACCCTCACCATCTCCTCCCTCG

-continued

AGCCCGAGGACTTCGCTGTGTACTACTGCCAGCAGTCCCGGCACGTGCCTTAC

ACCTTCGGGCAGGGGACCAAGGTGGAGATCAAG

SEQ ID NO: 54:
GAGATCGTCCTGACCCAGTCTCCTGCCACCCTGTCTCTGT

CTCCCGGCGAGAGAGCCACCCTGTCTTGCAGAGCCTCCCAGTCCGTGTCCAAC

TACGGCATCTCCTTCCTGAACTGGTACCAACAGAAGCCTGGCCAGGCCCCTA

GACTCCTCATCTACGCCGCCTCTTACCAGAAGCGGGGCATCCCCGCCAGATTC

TCTGGATCTGGATCTGGAACCGACTTCACCCTCACCATCTCCTCCCTCGAGCC

CGAGGACTTCGCAGTGTACTACTGCCAGCAGTCCTCCAACTTCCCCTGGACCT

TCGGACAGGGGACCAAGGTGGAGATCAAG;

SEQ ID NO: 55:
GAGATCGTCCTGACCCAGTCTCCTGCCACCCTGTCTCTGT

CTCCCGGCGAGAGAGCCACCCTGTCTTGCAGAGCCTCCCAGTCCGTGTCCAAC

TACGGCATCTCCTTCCTGAACTGGTACCAACAGAAGCCTGGCCAGGCCCCTA

GACTCCTCATCTACGCCGCCGAGTACAGAGGCAGAGGCATCCCCGCCAGATT

CTCTGGATCTGGATCTGGAACCGACTTCACCCTCACCATCTCCTCCCTCGAGC

CCGAGGACTTCGCAGTGTACTACTGCCAGCAGTCCTCCAACGTGCCCTACACC

TTCGGCCAGGGGACCAAGGTGGAGATCAAG;

SEQ ID NO: 56:
GAGATCGTCCTGACCCAGTCTCCTGCCACCCTGTCTCT

GTCTCCCGGCGAGAGAGCCACCCTGTCTTGCAGAGCCTCCCAGTCCGTGTCCA

ACTACGGCATCTCCTTCCTGAACTGGTACCAACAGAAGCCTGGCCAGGCCCCT

AGACTGCTCATCTACGCCGCCGAGTACCAGGGCAGAGGCATCCCTGCCAGAT

TCTCTGGATCTGGATCTGGAACCGACTTCACCCTCACCATCTCCTCCCTCGAG

CCCGAGGACTTCGCAGTGTACTACTGCCAGCAGTCCTCCAACGTGCCCTACAC

CTTCGGCCAGGGGACCAAGCTCGAGATCAAG;

SEQ ID NO: 57:
GAGATCGTCCTGACCCAGTCTCCTGCCACCCTGTCTC

TCTCTCCCGGCGAAAGAGCCACCCTCTCTTGCAGAGCCTCCCAGTCCGTGTCC

AACTACGGAATCTCCTTCCTCAACTGGTACCAACAGAAGCCTGGACAGGCCC

CTAGGCTCCTCATCTACGCAGCTGAGTACAGGGCTAGGGGAATCCCCGCTAG

GTTCTCTGGATCTGGGAGTGGGACCGACTTCACCCTCACCATCTCCTCCCTGG

AGCCCGAGGACTTCGCTGTGTACTACTGCCAGCAGTCCTCCAACGTGCCTTAC

ACCTTCGGGCAGGGGACCAAGGTGGAGATCAAG;

SEQ ID NO: 58:
GAGATCGTCCTGACCCAGTCTCCTGCCACCCTGTCTC

TGTCTCCCGGCGAGAGAGCCACCCTGTCTTGCAGAGCCTCCGAGTCCGTGGA

CAACTACGGCATCTCCTTCATGAACTGGTTCCAACAGAAGCCTGGCCAGGCC

CCTAGACTGCTCATCTACGCCGCCTCTAACCAGGGCTCTGGCATCCCCGCCAG

ATTCTCTGGATCTGGATCTGGAACCGACTTCACCCTCACCATCTCCTCCCTCG

AGCCCGAGGACTTCGCAGTGTACTTCTGCCAGCAGTCCAAGGAGGTCCCTTG

GACCTTTGGGCAGGGGACCAAGGTGGAGATCAAG;

-continued

SEQ ID NO: 59:
DAHKSEVAHRFKDLGEENFKALVLIAFAQYLQQCPFED

HVKLVNEVTEFAKTCVADESAENCDKSLHTLFGDKLCTVATLRETYGEMADCC

AKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLK

CASLQKFGERAFKAWAVARLSQRFPKAEFAEVSKLVTDLTKVHTECCHGDLLEC

ADDRADLAKYICENQDSISSKLKECCEKPLLEKSHCIAEVENDEMPADLPSLAAD

FVESKDVCKNYAEAKDVFLGMFLYEYARRHPDYSVVLLLRLAKTYETTLEKCC

AAADPHECYAKVFDEFKPLVEEPQNLIKQNCELFEQLGEYKFQNALLVRYTKKV

PQVSTPTLVEVSRNLGKVGSKCCKHPEAKRMPCAEDYLSVVLNQLCVLHEKTPV

SDRVTKCCTESLVNRRPCFSALEVDETYVPKEFNAETFTFHADICTLSEKERQIKK

QTALVELVKHKPKATKEQLKAVMDDFAAFVEKCCKADDKETCFAEEGKKLVA

ASQAALGL;

SEQ ID NO: 60:
DAHKSEVAHRFKDLGEENFKALVLIAFAQYLQQSPFED

HVKLVNEVTEFAKTCVADESAENCDKSLHTLFGDKLCTVATLRETYGEMADCC

AKQEPERNECFLQHKDDNPNLPRLVRPEVDVMCTAFHDNEETFLKKYLYEIARR

HPYFYAPELLFFAKRYKAAFTECCQAADKAACLLPKLDELRDEGKASSAKQRLK

CASLQKFGERAFKAWAVARLSQRFPKAEFAEVSKLVTDLTKVHTECCHGDLLEC

ADDRADLAKYICENQDSISSKLKECCEKPLLEKSHCIAEVENDEMPADLPSLAAD

FVESKDVCKNYAEAKDVFLGMFLYEYARRHPDYSVVLLLRLAKTYETTLEKCC

AAADPHECYAKVFDEFKPLVEEPQNLIKQNCELFEQLGEYKFQNALLVRYTKKV

PQVSTPTLVEVSRNLGKVGSKCCKHPEAKRMPCAEDYLSVVLNQLCVLHEKTPV

SDRVTKCCTESLVNRRPCFSALEVDETYVPKEFNAETFTFHADICTLSEKERQIKK

QTALVELVKHKPKATKEQLKAVMDDFAAFVEKCCKADDKETCFAEEGKKLVA

ASQAALGL

SEQ ID NO: 61:
LQEEDAGEYGCM.

EXAMPLES

The present invention is further illustrated by the following examples.

Example

Materials and Methods

Anti-hTREM-1 Antibody/Fab-Fragments Production

Novel anti-human TREM-1 (anti-hTREM1) murine antibodies were obtained by immunizing mice with a recombinant hTREM-1 protein. The sequences of the anti-hTREM-1 murine antibodies and Fab fragments were obtained by sequencing of hybridomas and sequence analysis (Diaclone, France). Recombinant chimeric anti-hTREM-1 antibodies (human IgG1 or hIgG1) and Fab fragments were then produced. Sequences from the variable regions were subcloned in a pQMCF-1.2 expression vector and the coding regions were verified by sequencing. CHOEBNALT85 1E9 cells (Icosagen) were then transfected with the pQMCF-1.2 expression vector in CHO TF medium (Xell AG) for 96 hours using R007 transfection reagent (Icosagen). Transfection was verified by PCR. Expression was checked by Coomassie staining, and secretion by Endpoint Coomassie staining in order to estimate the productivity. Then purification steps were performed using capture with HiTrap MabSelect SuRe for hIgG1 or HisTrap Excel for Fab fragments (both from GE Healthcare). Finally, a gel filtration was performed with Superdex 200 Increase 10/300 GL (GE Healthcare) and recovered proteins were filtered at 0.22 μm (Ultra Capsule GF, Merck Millipore). At the end of the process, chimeric hIgG1 or Fab fragments must meet the following acceptance criteria: concentration 1 mg/mL, purity >90% and endotoxin level under 0.1 EU/mg of protein. The purified hIgG1 and Fab fragments were kept in the following buffer: histidine-Tween buffer [20 mM histidine, 150 mM NaCl, 0.02% Tween-80, pH6.0].

Cell Isolation, Culture and Stimulation

U937 cells: cells of the human myelomonocytic cell line U937 (Culture Collections, Public Health England No 85011440) were cultured in RPMI 1640 medium containing GlutaMAX and supplemented with 10% Fetal Calf Serum or FCS (Thermo Fisher Scientific), 25 mM HEPES, 100 U/mL penicillin and streptomycin (all from Thermo Fisher Scientific). For some experiments, when indicated, U937 cells were cultured in the same conditions supplemented with 100 nM of 1,25-dihydroxyvitamin D3 also referred to as vitamin D3 or vitD3 (Sigma-Aldrich, USA) to induce an up-regulation of TREM-1.

THP-1 blue cells: the human THP1-Blue cell line is derived from the human THP-1 monocytic cell line by stable transfection of an NF-κB-inducible SEAP (secreted embryonic alkaline phosphatase) reporter construct (InvivoGen, France). Indeed, these cells report the activation of the NF-κB transcription factor. THP1-Blue cells were cultured in RPMI 1640 medium supplemented with 10% heat inactivated FBS (Fetal Bovine Serum), 2 mM L-glutamine, 25 mM HEPES, 100 μg/mL of normocin, and 100 U/mL of penicillin and streptomycin. For some experiments, when indicated, THP1-Blue cells were cultured in the same conditions supplemented with 100 nM of 1,25-dihydroxyvitamin D3 (vitD3) to induce an up-regulation of TREM-1.

TREM-1, TLR4, and CD14 expression on U937 cells, THP1 cells, or human primary neutrophils was assessed by flow cytometry. Cells were incubated for 10 min at 4° C. in the dark with anti-TREM1-APC, anti-CD14-PE, or anti-TLR4-FITC antibodies, or corresponding isotype controls (Miltenyi-Biotec, Germany), then washed and data were collected by flow cytometry (C6 Accuri, BD, USA). Flow cytometry data were analyzed using FlowJo software (TreeStar, USA).

Primary cells: primary human neutrophils were isolated from the peripheral blood of healthy donors by immunomagnetic negative cell sorting with EasySep™ Human Monocyte/Neutrophil Isolation Kits (StemCell, Canada) following the manufacturer's instructions. Purity was assessed by flow cytometry. Cells were suspended in RPMI 1640 medium containing GlutaMAX and supplemented with 10% FCS, 25 mM HEPES, 100 U/ml penicillin and streptomycin (all from Thermo Fisher Scientific) before stimulation. Human primary neutrophils were incubated in resting conditions (also referred to as non-stimulating conditions or NS), or with 100 ng/mL LPS from *E. coli* serotype 0127:B8 (Sigma-Aldrich), or with PP complex also referred to as PPx (corresponding to PGLYRP1 (peptidoglycan recognition protein 1) at 5 μg/mL complexed with 10 μg/mL of peptidoglycan, respectively from Biotechne, U K and Invivogen, France), or with peptidoglycan (PGN) alone (10 μg/mL), with or without anti-TREM-1 modulators (hIgG1 or Fab), at indicated times and concentrations. When indicated, the neutrophils were incubated with the clinical stage TREM-1 inhibitory peptide LR12 (a TLT-1 peptide having an amino acid as set forth in SEQ ID NO: 61-LQEEDAGEYGCM) at 100 μg/mL.

Binding to Human and Cynomolgus TREM-1

Cells: U937 cells or primary neutrophils were centrifuged for 5 minutes at 300 g and the pellets were resuspended to $1\times10^6$ cells/mL. Tested molecules (hIgG1 or Fab) were diluted at different concentrations (from 0.0001 to 20 μg/mL) in FACS buffer (1×PBS, 0.5% BSA, 2.5 mM EDTA). The cells were incubated for 30 minutes at 4° C. in presence of the tested molecules (hIgG1 or Fab), and then centrifuged for 5 minutes at 300 g. The supernatants were removed and a 1×PBS wash was performed. The cells were washed again and centrifuged for 5 minutes at 300 g and the pellets were recovered in FACS Buffer. Then, the secondary antibody (1:200, allophycocyanin (APC) AffiniPure F(ab')2 fragment goat anti-human IgG (H+L) (Jackson ImmunoResearch, USA) was added to the cell suspension. After 30 minutes of incubation at 4° C., the cells were washed with 1×PBS and centrifuged at 300 g for 5 minutes. Finally, the cells were resuspended in FACS buffer and analyzed by flow cytometry (C6 Accuri, BD, USA) in order to quantify the binding of the tested molecules (hIgG1 or Fab) to the cells. Finally, flow cytometry data were analyzed using FlowJo software.

Surface plasmon resonance (SPR): in order to evaluate the interaction kinetics for TREM-1 antibodies or Fabs to hTREM-1 (human TREM-1) and cTREM-1 (cynomolgus monkey TREM-1), surface plasmon resonance (SPR) assays were carried out (Biacore™ T200, GE Healthcare Biosciences). The anti-human Fc antibodies (Cytiva) were immobilized on CM5 sensor chip in order to evaluate IgG1 affinities and Fabs were directly immobilized on the chip. Immobilization experiments were performed at 25° C. using HBS-EP+1× running buffer (10 mM HEPES, 150 mM NaCl, 3 mM EDTA, 0.05% surfactant P20, pH 7.4). The anti-human Fc antibodies or Fabs were diluted in 10 mM sodium acetate at acidic pH before the immobilization procedure using amine coupling on the dextran matrix of the sensor chips. The surface was activated using a solution of 100 mM 1-ethyl-3-[3-dimethylaminopropyl]carbodimide hydrochloride or EDC and 400 mM N-hydroxysulfosuccinimide or NHS (EDC/NHS) (Liu Y, Wilson WD. Methods Mol Biol. 2010; 613:1-23). Following these injections, ethanolamine was injected to deactivate the surface. The immobilization wizard was used to obtain several thousand of immobilized RU (resonance units). The immobilization level was chosen in order to have a proper covering of the sensor chip surface. Preliminary manual runs were performed in order to optimize the capture conditions and to obtain similar capture levels for all the human antibodies. Binding of hTREM-1 or cTREM-1 proteins was conducted by injecting analyte over all flow cells. The human and cynomolgus TREM-1 proteins were diluted into running buffer (HBS-EP+1×) at concentrations of 0.1 nM, 0.5 nM, 2.5 nM, 10 nM and 40 nM, or 0.5 nM, 2 nM, 10 nM, 40 nM and 200 nM, respectively. The concentrations were evaluated using the Single Cycle Kinetics method. This approach consists of a sequential injection of increasing concentration of the analyte, with a single regeneration step using a magnesium chloride buffer (Cytiva) at the end of the cycle. Binding affinity of TREM-1 antibodies or Fabs with hTREM-1 or cTREM-1 was quantified by determination of the equilibrium dissociation constant ($K_D$) determined by measurement of the kinetics of complex formation and dissociation. The rate constants corresponding to the association and the dissociation of a monovalent complex such as $k_a$ (association rate) and $k_d$ (dissociation rate) were retrieved by fitting data to 1:1 Langmuir model using the Biacore T200 Evaluation Software, version 3.1 (GE Healthcare). $K_D$ is related to $k_a$ and $k_d$ through the equation $K_D=k_d/k_a$.

Reactive Oxygen Species (ROS) Production

Quantification of intracellular ROS production was assessed using cell-permeable DCFDA (2',7'-dichlorofluorescein diacetate), a chemically reduced form of fluorescein used as an indicator of the presence of ROS in cells (Thermo Fisher Scientific). Upon cleavage of the acetate groups by intracellular esterases and oxidation, the nonfluorescent DCFDA is converted to the highly fluorescent 2',7'-dichlorofluorescein (DCF). For example, human primary neutrophils were incubated 2 hours at 37° C. 5% $CO_2$ with 5 μM of DCFDA, in presence of the tested molecules (hIgG1 or Fab) with or without 100 ng/mL LPS, or PP complex (corresponding to PGLYRP1 (peptidoglycan recognition protein 1) at 5 μg/mL complexed with 10 μg/mL of peptidoglycan, respectively from Biotechne, U K and Invivogen, France), or peptidoglycan (PGN) alone (10 μg/mL). Data were acquired using flow cytometry (C6 Accuri, BD, USA) or a Fluorometer (Varioskan Lux, ThermoScientific). Results are expressed as mean fluorescence intensity (MFI) or relative fluorescence unit (RFU).

THP-1 Quanti-Blue Assay: NF-κB Cell Line Reporter

The QUANTI-Blue assay (InvivoGen) is a colorimetric enzymatic test for determining the activity of SEAP. This test is used on THP1-Blue cells which contain the SEAP reporter gene inducible by NF-κB. Using this test, the activation of NF-κB can be assessed by determining the activity of SEAP (measured at 650 nm). After 48 hours of culture of THP-1 blue cells with 100 nM of 1,25-dihydroxyvitamin D3 (vitD3), the Quanti-Blue assay was performed. In a 96-well microplate, the cells ($1\times10^5$ cells/well) were incubated in the presence or absence of the tested molecule (hIgG1 or Fab) at the indicated concentrations (0.1-1-10 μg/mL) and LPS (0.1 μg/mL) at 37° C., 5% $CO_2$ between 1 and 10 hour(s). Subsequently, the cells were centrifuged for 5 minutes at 300 g and the supernatants were collected. In a new transparent 96-well microplate, the cell supernatants were mixed with the Quanti-Blue reagent (1:10) and incubated at 37° C., 5% $CO_2$ for 30 minutes. Finally, the optical density was measured at 650 nm with a microplate reader (Varioskan Lux, ThermoScientific).

Whole Blood Assay

Using stimulation assays of whole blood obtained from healthy human donors, inflammatory cytokines levels (IL-1β, TNF-α, IL-6, IL-8, and IL-10) were assessed. The tested molecules (hIgG1 or Fab) were first diluted to different concentrations (0.1-1-10 μg/mL or as indicated) and added to the wells of 12-well plates in presence or absence of LPS (0.1 μg/mL, InvivoGen, France), or in presence of PP complex (corresponding to PGLYRP1 at 5 μg/mL complexed with 10 μg/mL of peptidoglycan, respectively from Biotechne, U K and Invivogen, France) or only with peptidoglycan also referred to PGN (Invivogen, France). Subsequently, whole blood (after the lysis of red blood cells with ammonium chloride (Stemcell, France)) was added to the wells and incubated for 24 hours at 37° C., 5% $CO_2$. Then, samples were centrifuged for 10 minutes at 300 g in order to recover the plasma in which the IL-8 level was assessed using the Quantikine ELISA Human IL-8/CXCL8 kit according to the manufacturer's instructions (R&D Systems) or using Ella technology (Protein Simple, UK), an automated immunoassay system. The samples were added in Single Plex or Multiplex cartridges (Protein Simple, UK) in order to evaluate levels of the 5 cytokines (IL-1β, TNF-α, IL-6, IL-8, and IL-10) in a single assay.

Alternatively, whole blood from cynomolgus was used. Using stimulation assays of whole blood obtained from healthy cynomolgus donors (*Macaca fascicularis*), inflammatory cytokines levels (IL-8, TNF-α, IL-6) were assessed. The tested molecules (hIgG1 or Fab) were first diluted to different concentrations (0.2-2-20 μg/mL) and added to the wells of 24-well plates in presence of PP complex (or PPx) (corresponding to PGLYRP1 at 5 μg/mL complexed with 10 μg/mL of peptidoglycan, respectively from Biotechne, U K and Invivogen, France) or only with peptidoglycan also referred to PGN (Invivogen, France). Subsequently, whole blood (after the lysis of red blood cells with ammonium chloride (Stemcell, France)) was added to the wells and incubated for 24 hours at 37° C., 5% $CO_2$. Then, samples were centrifuged for 10 minutes at 300 g in order to recover the plasma in which the TNF-α, IL-6 and IL-8 level was assessed using Ella technology (Protein Simple, UK), an automated immunoassay system. The samples were added in Single Plex or Multiplex cartridges (Protein Simple, UK) in order to evaluate levels of the 3 cytokines (TNF-α, IL-6 and IL-8) in a single assay.

U937-VitD3 Stimulation

U937 cells were cultured in RPMI 1640 GlutaMAX medium supplemented with 10% FCS, 25 mM HEPES, 100 U/ml penicillin and streptomycin in presence of 100 nM of 1,25-dihydroxyvitamin D3 (vitD3) for 48 hours to induce an up-regulation of TREM-1. Then, cells were recovered and plated ($1\times10^5$ cells/well) in the presence or absence of the tested molecule (hIgG1 or Fab) at the indicated concentrations (0.1-1-10 μg/mL) and LPS (0.1 μg/mL) at 37° C., 5% $CO_2$ for 24 hours. Subsequently, the cells were centrifuged for 5 minutes at 300 g and the supernatants were collected. Finally, the concentrations of inflammatory cytokines levels (IL-1β, IL-6 and IL-10) in the supernatants were assessed using Ella technology (Protein Simple, UK).

Neutrophil Stimulation

Primary human neutrophils were isolated from the blood of healthy donors as previously described and plated at $1\times10^6$ cells/mL. Then, cells were incubated in the presence or absence of the tested molecule (hIgG1 or Fab) at the indicated concentrations (0.1-10 μg/mL) and LPS (0.1 μg/mL) at 37° C. 5%, $CO_2$ for 24 h. Subsequently, the cells were centrifuged for 5 minutes at 300 g and the supernatants were collected. Finally, the concentrations of IL-6 or IL-8 in the supernatants were assessed using the Quantikine ELISA Human IL-6 or IL-8 kit according to the manufacturer's instructions (R&D Systems, France) or Ella technology (Protein Simple, UK).

Humanized Immune System (his-) Mice

BRGSF mice from GenOway (France) are BALB/c mice displaying the Rag2−/−Il2rg−/−SirpaNODFlk2+/− genotype. His (humanized immune system) mice were generated as follows: briefly, newborn mice (<5 days of age) were transplanted with approximately $1\times10^5$ human hematopoietic progenitor cells (hHPC) $CD34^+$ obtained from umbilical cord by intra-hepatic injection after a sub-lethal irradiation. In order to boost the myeloid immune system, all mice received 4 intra-peritoneal (i.p.) injections of 10 μg of recombinant human hFLT3-L/Fc every two days before experiments.

Human Experimental Endotoxemia

His-mice were subjected to LPS challenge to evaluate the in vivo immunomodulatory effect of anti-TREM-1 INO-10 Fab fragment (INO-10F). In brief, one day following Flt3-ligand (FLT3L) boost, his-mice were administered with a single intraperitoneal (i.p.) dose of 10 mg/kg of either PBS, INO-10F, or a fusion protein with an extended half-life comprising INO-10F coupled with human serum albumin also known as HSA (INO-10F-HSA), followed 30 min later by an i.p. injection of 8 mg/kg of LPS (lipopolysaccharides; *E. coli* serotype 0127:B8, batch L3129, Sigma Chemical, St Louis, France). Concentrations were adjusted as to inject the same volumes in each group of mice. After 8 hours, blood samples were collected by intracardiac punction and were harvested in EDTA-tubes. Plasma was obtained by centrifugation of the whole blood (300 g, 10 min) and stored at −80° C. The plasma levels of cytokines (CCL-2, IL-1β, IL-10, IL-6, IL-8, IP-10, and TNF-α) were determined using the simple Plex cartridges, run by Ella technology (Protein Simple, UK).

Results

INO-10F Efficiently Blocks TREM-1 Activation in Human Primary Neutrophils.

A total of 51 anti-hTREM-1 unique sequences were obtained and produced as human IgG1 chimeric antibodies (hIgG1) and corresponding Fab fragments (or in short Fabs). These constructs were screened for their ability to bind human TREM-1. After validation of their interaction with human TREM-1, all constructs were screened for their ability to decrease the release of reactive oxygen species (ROS) by human primary neutrophils following the activation of the neutrophils with lipopolysaccharides (LPS). Indeed, activation of TREM-1 on neutrophils (which express TREM-1 at their surface) through their incubation with LPS notably leads to ROS production by the neutrophils. The ability of the tested constructs to decrease ROS production by neutrophils activated with LPS thus reflects their ability to inhibit TREM-1. One lead was identified, the so-called INO-10F, an anti-hTREM-1 Fab fragment. As shown on FIG. 1, INO-10F was able to significantly decrease ROS release by neutrophils at 1 μg/mL and 10 μg/mL. INO-10F was thus able to inhibit TREM-1 activation. Based on data obtained from functional screening, INO-10F was identified as the best lead compound.

Figure 2:
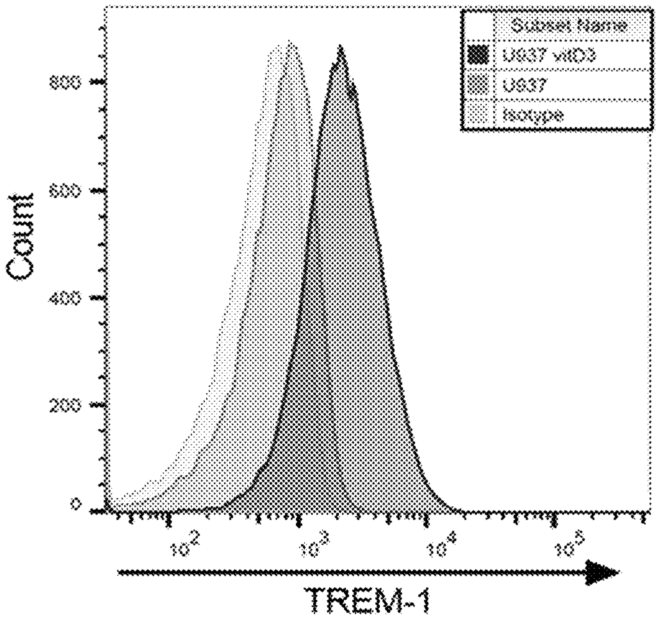
FIG. 2 is a graph showing the expression of TREM-1 (assessed by flow cytometry) on U937 cells and on U937 cells pre-treated with vitamin D3 (U937-vitD3) to induce an up-regulation of TREM-1.
Figure 3:
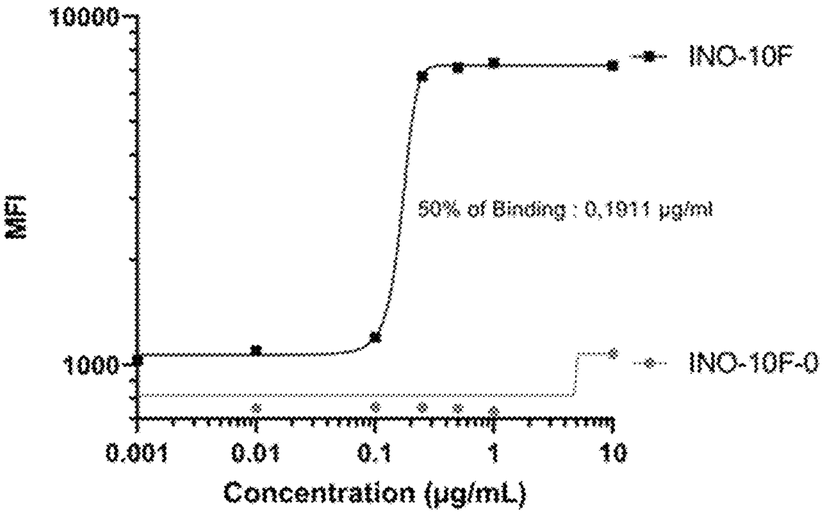
FIG. 3 is a graph showing the binding (assessed by flow cytometry) of anti-TREM-1 Fab INO-10F and a negative control INO-10F-0 (0.01-10 ug/mL) on U937 cells pre-treated with vitamin D3 to induce an up-regulation of TREM-1.
Figure 4A:
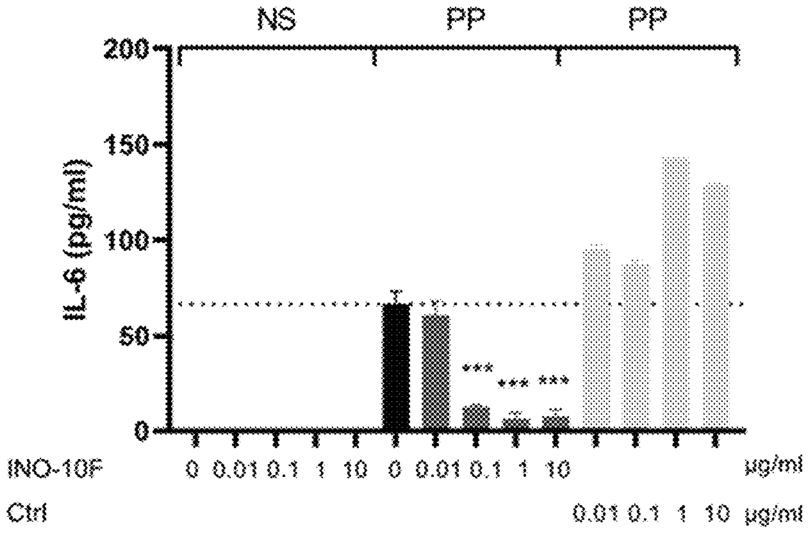
FIG. 4A-C are a set of graphs showing the effects of anti-TREM-1 Fab INO-10F on the production of cytokines (IL-6, IL-10 U937 cells by and IL-1B) pre-treated with vitamin D3 (U937-vitD3). The concentrations of IL-6 (4A), IL-10 (4B) and IL-1B (4C) in supernatants were determined after a 24-hour stimulation of the U937-vitD3 cells in resting conditions or PP-activated conditions (stimulation with the PP complex corresponding to PGLYRP1 complexed with peptidoglycan) in presence of INO-10F or control (INO- 10F—O-Ctrl) at the indicated concentrations. * p<0.05,  p<0.01, * p<0.001 versus PP alone as determined by a parametric t-test.
Figure 4B:
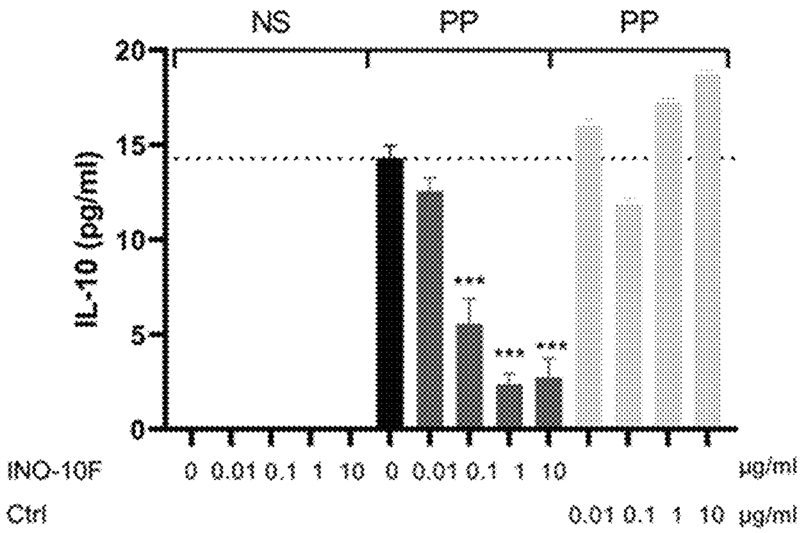
Figure 4C:
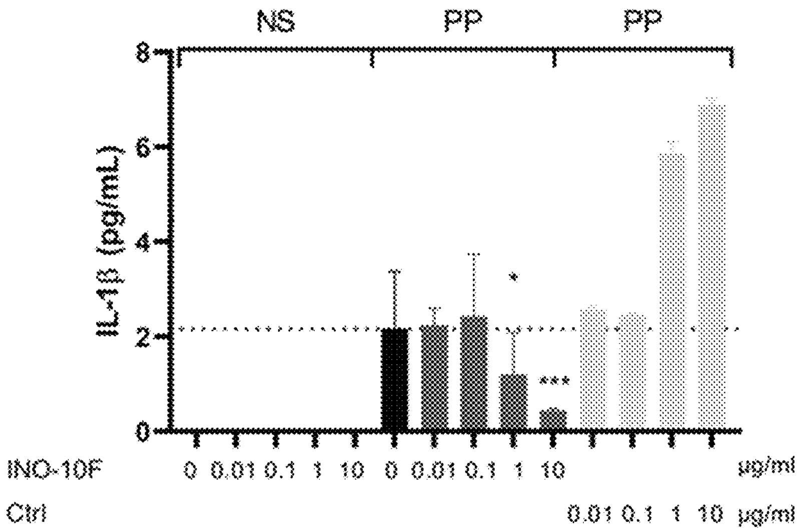

INO-10F Binding to Human TREM-1 by Flow Cytometry and Inhibition of TREM-1 Activation on U937-vitD3 Cells Incubation of U937 cells with vitamin D3 (1,25-dihydroxyvitamin D3) was associated with an increase in TREM-1 expression at the membrane as compared to TREM-1 expression at the membrane of untreated U937 control cells (FIG. 2). Using flow cytometry, INO-10F was shown to bind human TREM-1 in a dose-dependent manner on U937-vitD3 cells (i.e., U937 cells pre-treated with vitamin D3), with a 50% binding reached at approximately 0.2 μg/mL (FIG. 3). As expected, the negative control INO-10F-0 did not show any binding to human TREM-1 on U937-vitD3 cells (FIG. 3). Interestingly, INO-10F was also shown to inhibit TREM-1 activation in a dose-dependent manner. The activation of TREM-1 on myeloid cells (which express TREM-1 at their surface) through the induction of an inflammatory response, for example with a PGLYRP-1:PGN complex (or PP), notably leads to cytokine/chemokine expression and secretion by said cells. As shown on FIG. 4, incubation of increasing concentrations of INO-10F with U937-vitD3 cells was associated with a decrease in the release of interleukin-6 also known as IL-6 (FIG. 4A), interleukin-10 also known as IL-10 (FIG. 4B), and interleukin-1β also known as IL-1β (FIG. 4C) induced by a 24-hour stimulation of the U937-vitD3 cells with the PGLYRP-1:PGN complex (PPx or PP). In that assay, the maximum effect of INO-10F was achieved between 1 and 10 μg/mL and 50% of inhibition was reached at approximately 0.1 μg/mL.

Figure 5A:
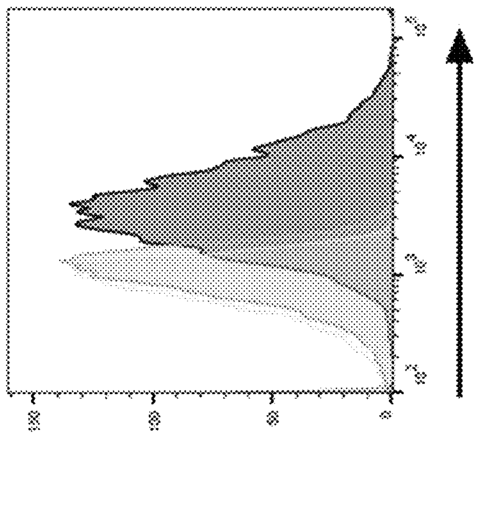
FIGS. 5A-C are a set of graphs showing TREM-1 expression (5A), CD14 expression (5B and TLR4 expression (5C) on THP-1 cells and THP-1 cells pre-treated with vitamin D3 to induce an up-regulation of TREM-1. The expression of TREM-1, CD14 and TLR4 was assessed by flow cytometry and compared to isotype control.
Figure 5B:
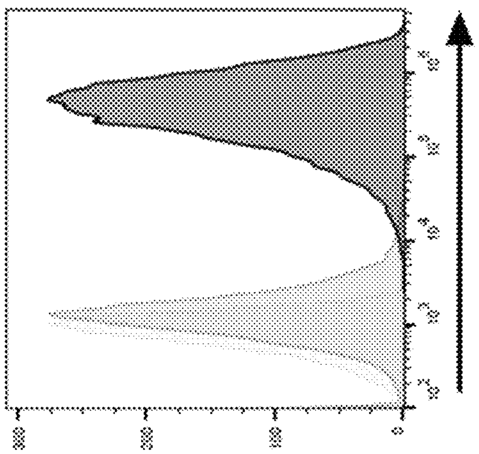
Figure 5C:
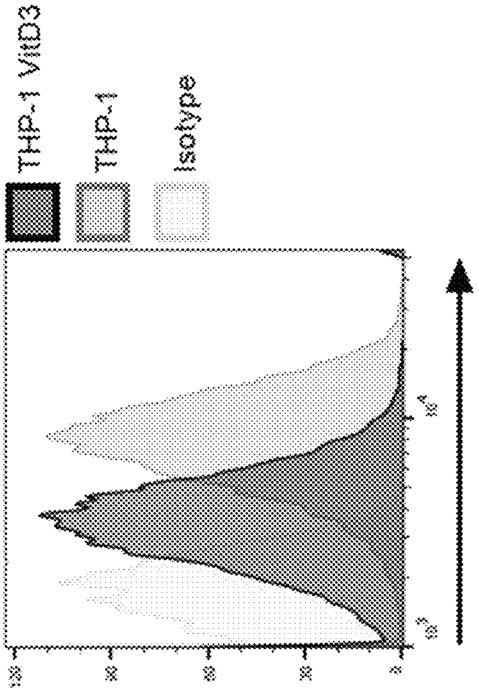
Figure 6:
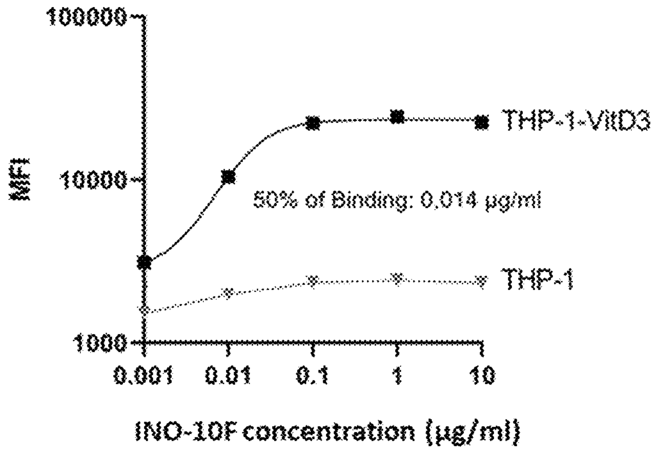
FIG. 6 is a graph showing the binding (assessed by flow cytometry) of anti-TREM-1 Fab INO-10F (0.01-10 ug/mL) on THP-1 cells and on THP-1 cells pre-treated with vitamin D3 (THP-1-vitD3).

INO-10F Binding to Human TREM-1 by Flow Cytometry and Inhibition of TREM-1 Activation on THP-1 Blue-vitD3 Cells Incubation of THP-1 cells with vitamin D3 was associated with an increase in TREM-1 expression (FIG. 5A), as well as an increase in human CD14 or hCD14 (FIG. 5B) and a decrease in human Toll Like Receptor 4 or hTLR4 (FIG. 5C) as compared to TREM-1 expression at the membrane of untreated THP-1 cells. Using flow cytometry, INO-10F was shown to bind human TREM-1 expressed in THP-1-vitD3 cells (THP-1 cells pre-treated with vitamin D3) in a dose-dependent manner, with a 50% binding reached at 0.014 μg/mL (FIG. 6). As expected, there was little binding of INO-10F to untreated THP-1 control cells (FIG. 6).

Figure 7A:
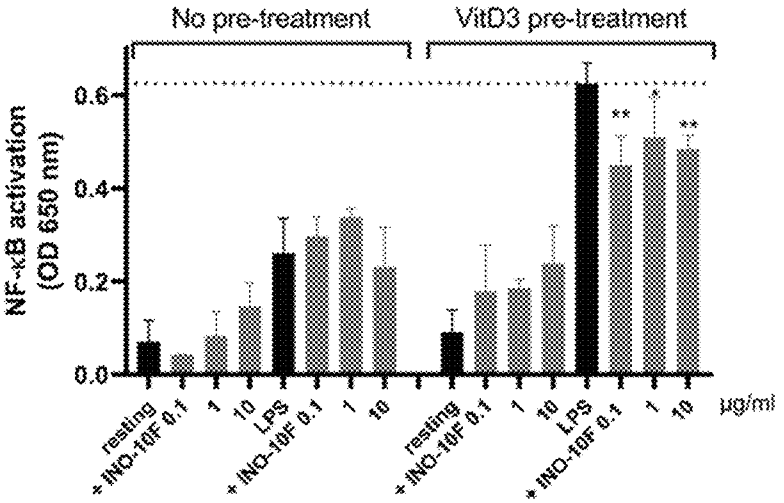
FIGS. 7A-B show the effects of anti-TREM-1 Fab INO-10F on the activation of NF-KB in THP-1 Blue cells and THP-1-vitD3 Blue cells (i.e., THP-1 Blue cells pre-treated with vitamin D3 to induce an up-regulation of TREM-1). 7A is a histogram showing the activation of NF-KB in THP-1 Blue and THP-1-vitD3 Blue cells assessed by determining the activity of SEAP (measured at 650 nm) either in the presence of INO-10F at the indicated concentrations (0.1-10 ug/mL) in resting conditions (resting+INO-10F) for 6 h or in the presence of INO-10F at the indicated concentrations (0.1-10 ug/mL) and LPS (LPS+INO-10F) for 6h. * p<0.05, ** p<0.01, versus LPS alone as determined by a parametric t-test. 7B is a graph showing the kinetics of NF-KB activation upon LPS priming (100 ng/ml) in presence of INO-10F at the indicated concentrations (0.1-10 ug/mL). * p<0.05, ** p<0.01 versus LPS alone as determined by a two-way ANOVA test.
Figure 7B:
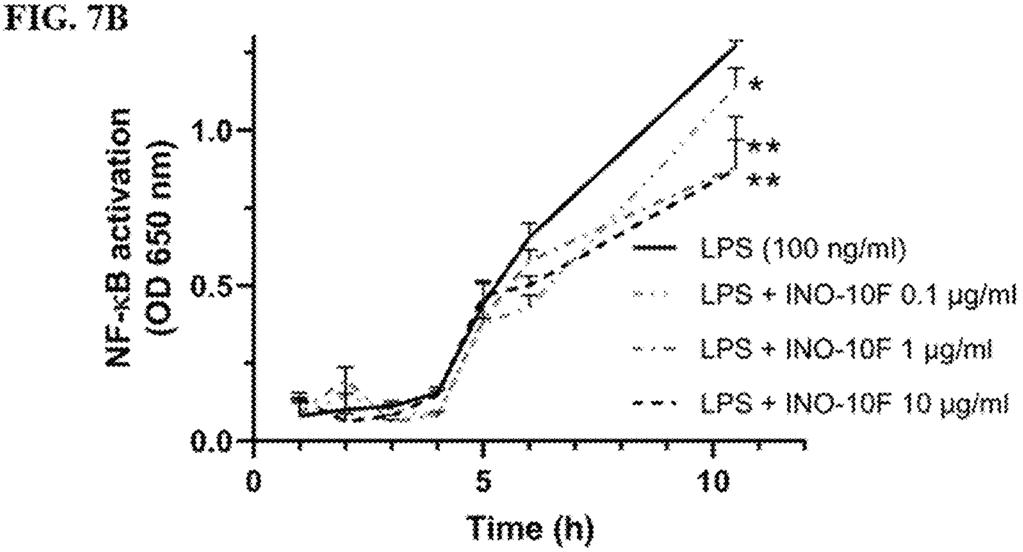

In order to evaluate the activity of INO-10F, untreated THP-1 Blue cells or THP-1 Blue cells pretreated with vitamin D3 for 48 hours were incubated with increasing doses of INO-10F in presence or absence of LPS (100 ng/mL). The activation of TREM-1 on myeloid cells such as monocytes (which express TREM-1 at their surface) through the induction of an inflammatory response, for example with LPS, notably leads to NF-κB activation in said cells. After 6 hours, NF-κB activation was assessed using Quanti-Blue reagent. As reflected through the inhibition of NF-κB activation shown on FIG. 7A, INO-10F was able to inhibit TREM-1 only on cells overexpressing TREM-1, with an effect between 0.1 and 10 μg/mL. INO-10F had no effect on LPS-activated naïve THP-1 Blue cells (i.e., THP-1 Blue cells which were not pre-treated with vitamin D3). A second set of experiments further confirmed that INO-10F was able to limit the LPS-induced activation of NF-kB in a time- and dose-dependent manner in THP-1 Blue cells pre-treated with vitamin D3. INO-10F inhibited NF-κB activation between 6 and 10 hours with a highest effect at 10 hours depending on the dose (FIG. 7B).

Figure 8:
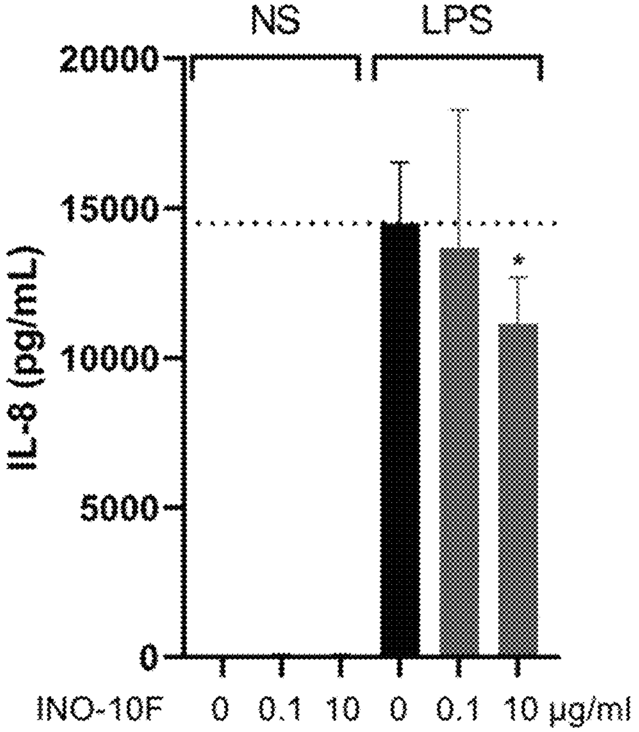
FIG. 8 is a histogram showing the effects of anti-TREM-1 Fab INO-10F on the production of IL-8 by THP-1 cells pre-treated with vitamin D3 to induce an up-regulation of TREM-1 (THP-1-vitD3). The concentration of IL-8 in supernatants was assessed after a 24-hour stimulation of THP-1-vitD3 cells with LPS or no stimulation (NS) in presence of INO-10F at the indicated concentrations (0, 0.1 or 10 μg/mL). * p<0.05,  p<0.01, * p<0.001 versus LPS alone as determined by parametric t-test.

Then, the IL-8 production of THP-1 Blue cells was assessed after their pre-treatment with vitamin D3 and their stimulation for 24 hours with LPS (100 ng/mL) in presence of increasing concentrations of INO-10F (0, 0.1 and 10 μg/mL). INO-10F decreased, in a concentration dependent manner, the release of IL-8 induced by LPS stimulation with a maximum effect reached at 10 μg/mL (FIG. 8). This result confirms that INO-10F is able to inhibit TREM-1 in THP-1 Blue cells pre-treated with vitamin D3.

Figure 9:
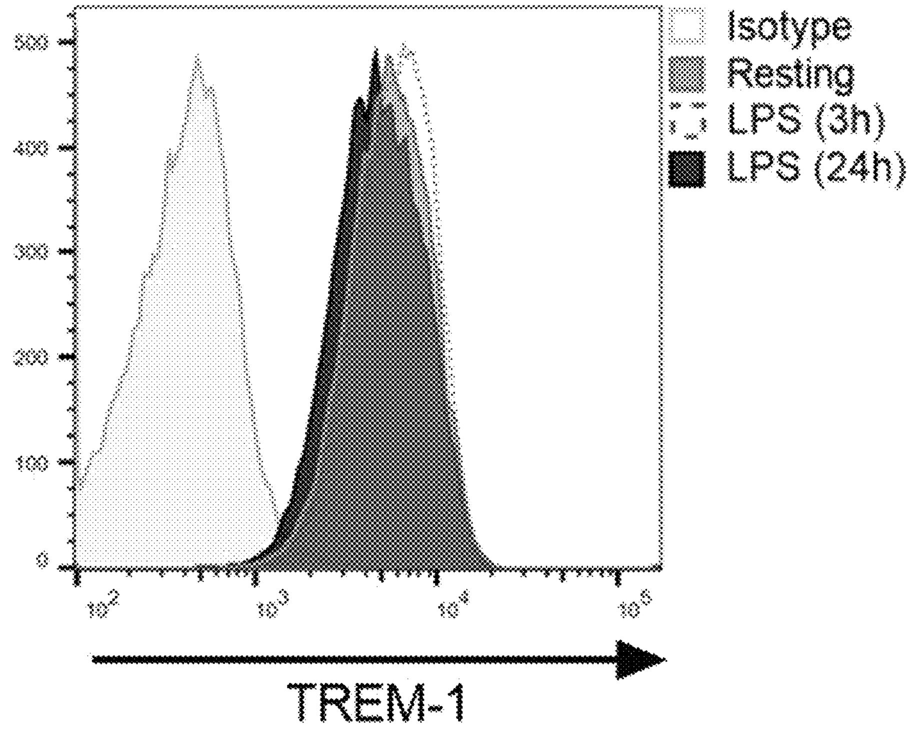
FIG. 9 is a graph showing TREM-1 expression (assessed by flow cytometry) on neutrophils at the indicated times. The human primary neutrophils were either cultured in resting conditions, stimulated with LPS for 3h, or stimulated with LPS for 24 h. The expression of TREM-1 is compared to isotype control.
Figure 10:
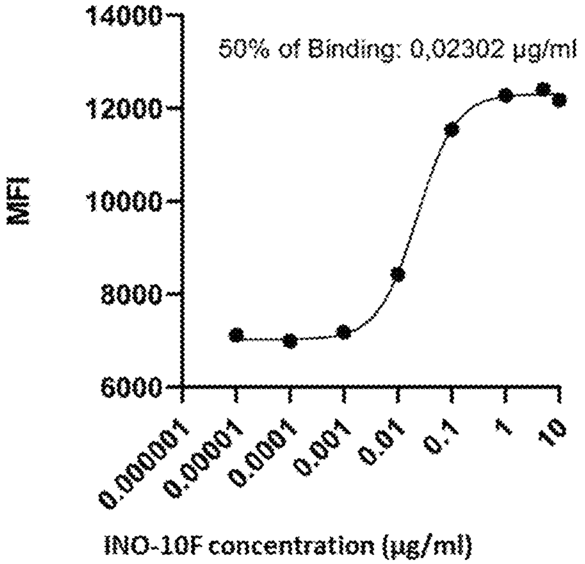
FIG. 10 is a graph showing the binding of INO-10F (assessed by flow cytometry) on freshly isolated human primary neutrophils at different concentrations (from 0.000001 to 10 μg/mL).
Figure 11:
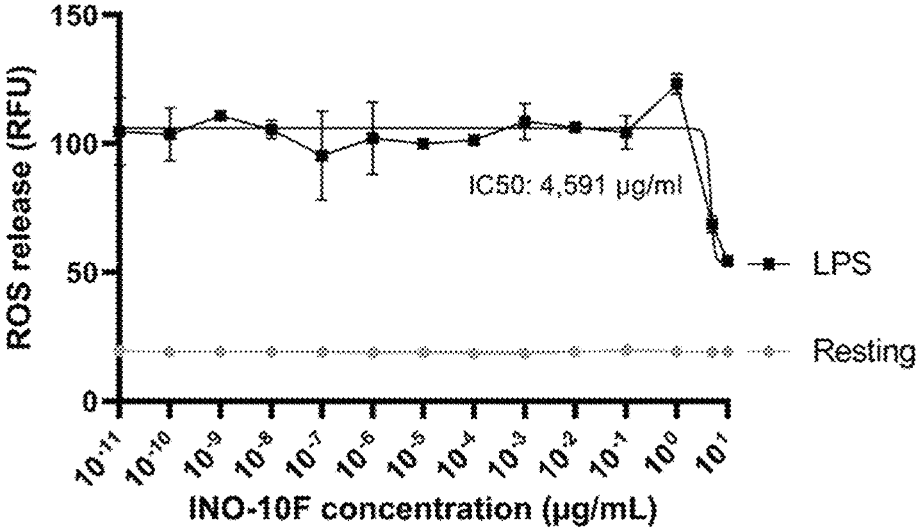
FIG. 11 is a graph showing the reactive oxygen species (ROS) release by human primary neutrophils upon a 2 h incubation in the presence of INO-10F at the indicated concentrations (from 10-11 to 101 μg/mL) either with LPS (black squares) or in resting conditions (grey circles).
Figure 12A:
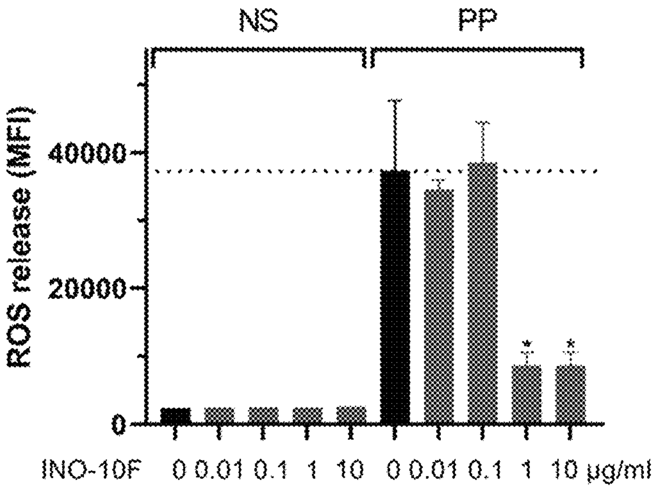
FIGS. 12A-B show the effects of anti-TREM-1 Fab INO-10F on reactive oxygen species (ROS) release by neutrophils. 12A is a histogram showing ROS release by human primary neutrophils upon a 2 h incubation with INO-10F at the indicated concentrations (0-10 ug/mL) either in resting conditions (NS) or stimulated with the PP complex corresponding to PGLYRP1 complexed with peptidoglycan (PP). 12B is a graph showing the binding percentage (black circles) of INO-10F at the indicated concentrations (0-10 ug/mL) on human primary neutrophils and the ROS release percentage (grey squares) by human primary neutrophils after PP stimulation in the presence of INO-10F at the indicated concentrations (0-10 ug/mL).
Figure 12B:
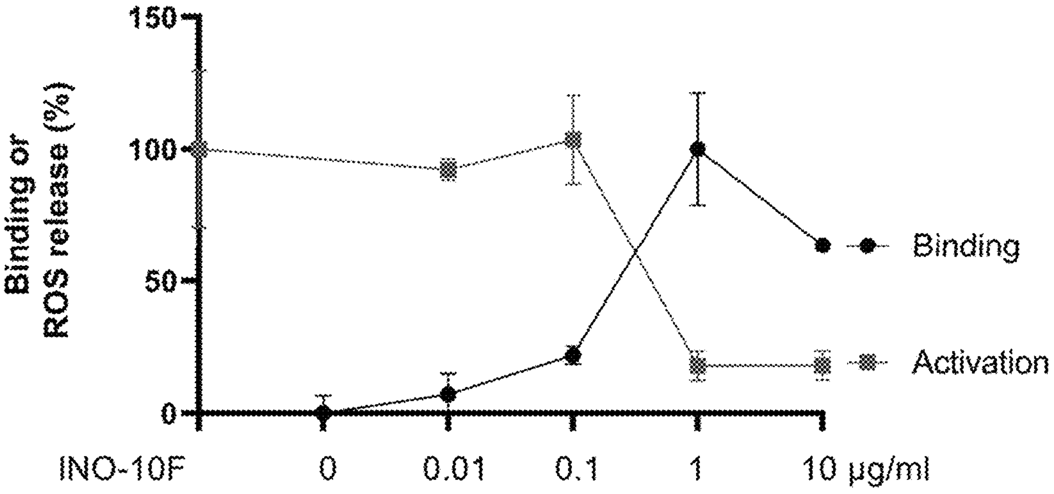

INO-10F Binding to Human TREM-1 by Flow Cytometry and Inhibition of TREM-1 Activation on Primary Neutrophils and in Whole Blood Human primary neutrophils express high levels of TREM-1 at the membrane under physiological conditions and do not up-regulate its expression upon LPS stimulation. Indeed, as shown on FIG. 9, the expression of TREM-1 at the membrane of human primary neutrophils is similar in resting conditions and after stimulation with LPS, either for 3 hours or for 24 hours. INO-10F was able to bind human TREM-1 in a concentration-dependent manner on freshly isolated human neutrophils with a 50% binding reached between 0.01 and 0.1 μg/mL, at about 0.023 μg/mL (FIG. 10). Then, the ability of INO-10F to inhibit TREM-1 activation on neutrophils was evaluated through the assessment of their release of ROS upon LPS stimulation. As expected, INO-10F alone did not induce any activation of TREM-1 as observed through the absence of ROS production in resting conditions (FIG. 11). ROS were produced by the human primary neutrophils upon LPS stimulation, and INO-10F decreased said production of ROS by 50% at a concentration of about 4.6 μg/mL, confirming its ability to inhibit TREM-1 (FIG. 11). A similar experiment was conducted, using the PGLYRP-1:PGN complex (PPx or PP) to induce ROS production in human primary neutrophils by direct activation of TREM-1. INO-10F also decreased ROS production by neutrophils with a maximum effect reached at 1 μg/mL (FIG. 12A) which corresponds to the maximum binding concentration to human TREM-1 on human primary neutrophils (FIG. 12B).

Figure 13:
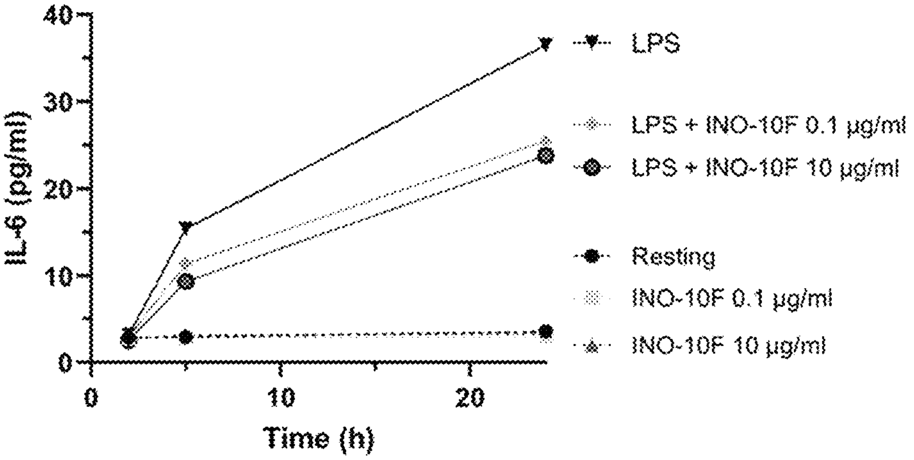
FIG. 13 is a graph showing the effects of anti-TREM-1 Fab INO-10F on the production of IL-6 by neutrophils. The concentration of IL-6 in neutrophil supernatants was assessed after a 6-hour and a 24-hour stimulation with INO-10F at the indicated concentrations (0, 0.1 or 10 μg/mL) either with LPS or in resting conditions.

Finally, IL-6 secretion by human primary neutrophils was assessed after incubation of the neutrophils during 0, 6 and 24 h in presence of INO-10F (0.1 or 10 μg/mL) either with LPS (100 mg/mL) or in resting conditions. As shown on FIG. 13, INO-10F reduced the release of IL-6 induced by LPS in a dose- and time-dependent manner.

Figure 14A:
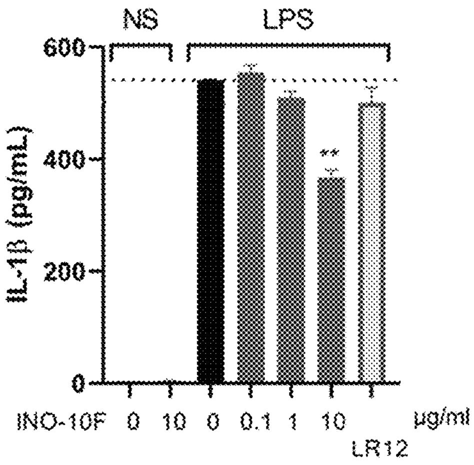
FIGS. 14A-E are a set of histograms showing the effect of anti-TREM-1 Fab INO-10F on cytokine plasma concentration following a 24-hour whole blood stimulation assay. INO-10F was added at the indicated concentrations (0-10 ug/mL) either in resting conditions (NS) or with LPS. As a positive control, a stimulation with a known TREM-1 inhibitor (peptide LR12) was carried out with LPS. After 24 h, the expression of the following cytokines were assessed: IL-1β (14A), IL-10 (14B), TNF-α (14C) , IL-6 (14D), and IL-8 (14E). * p<0.05, ** p<0.01, p<0.001 versus LPS alone as determined by a parametric t-test.
Figure 14B:
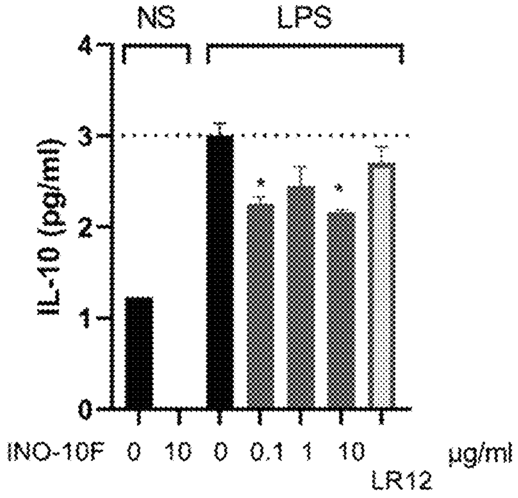
Figure 14C:
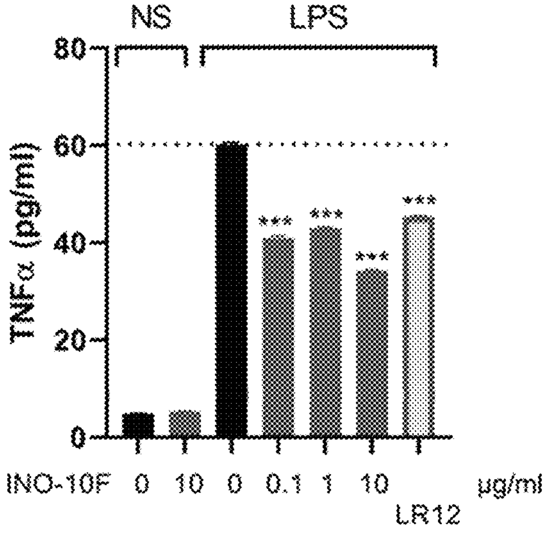
Figure 14D:
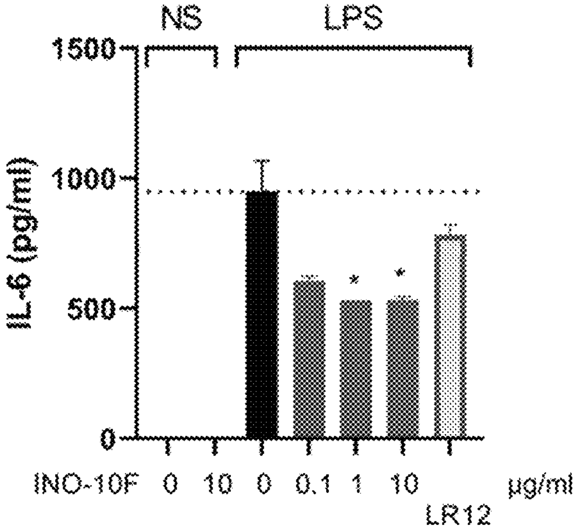
Figure 14E:
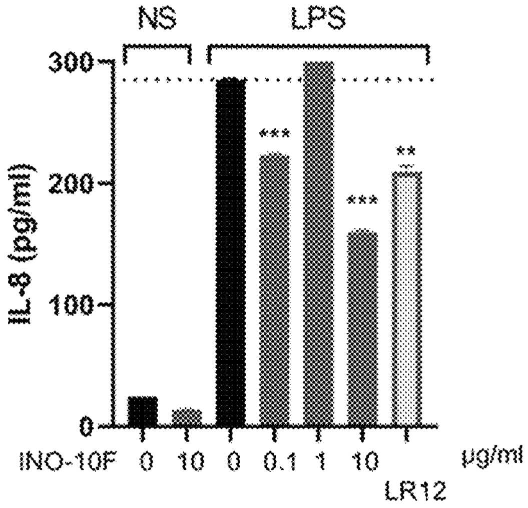
Figure 15:
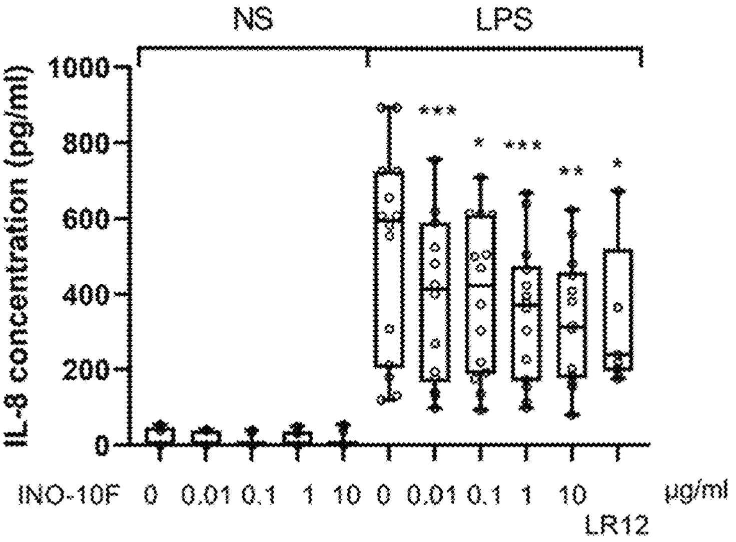
FIG. 15 is a box plot showing IL-8 plasma concentrations following a 24-hour whole blood stimulation assay. INO-10F was added to whole blood from 14 healthy volunteers at the indicated concentrations (0-10 ug/mL) either in resting conditions (NS) or with LPS. As a positive control, a stimulation with a known TREM-1 inhibitor (peptide LR12) was carried out with LPS. After 24h, the plasma concentration of IL-8 was assessed. * p<0.05,  p<0.01, *p<0.001 versus LPS alone as determined by a paired non-parametric t-test.

To further confirm the immunomodulatory properties of INO-10F through its inhibition of TREM-1, the effect of INO-10F was assessed in a human whole blood cytokine assay stimulation. As detailed above, whole blood obtained from healthy human donors was incubated for 24 hours at 37° C., 5% $CO_2$ in presence of LPS (100 ng/mL) and either INO-10F or a positive control (i.e., peptide LR12 known to inhibit TREM-1). The plasma was recovered and the plasma levels of several cytokines were measured. As shown on FIG. 14, in this assay, INO-10F reduced, in a dose-dependent manner, the release of several cytokines. Indeed, INO-10F limited the LPS-induced release of IL-1β (FIG. 14A), of IL-10 (FIG. 14B), of TNF-α (FIG. 14C), of IL-6 (FIG. 14D), and of IL-8 (FIG. 14E). The effect of INO-10F on IL-8 plasma concentration was also assessed in vitro after LPS stimulation of whole blood samples collected from 14 healthy volunteers. As shown on FIG. 15, INO-10F induced a dose-dependent decrease (from 0.01 to 10 μg/mL) of IL-8 plasma concentration. A decrease in the LPS-induced production of IL-8 was also observed with the peptide LR12 (positive control). In the whole blood assays, INO-10F did not induce any significant production of IL-8 or any other studied cytokines in unstimulated condition (i.e., in the absence of LPS).

Blocking Human TREM-1 in a BRGS-F Mouse Endotoxemia Model Reduces Immune-Inflammatory Response.

Figure 16A:
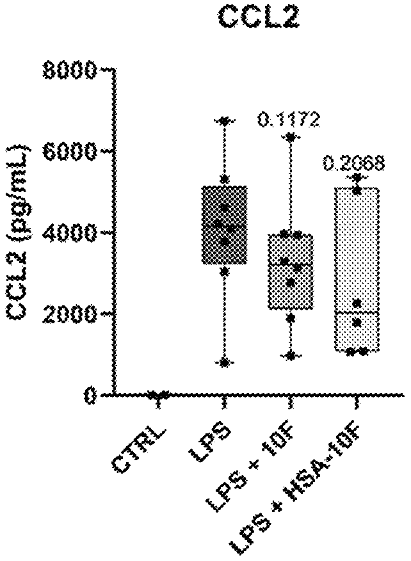
FIGS. 16A-G are a set of box plots showing the effect of anti-TREM-1 Fabs INO-10F and HSA-INO-10F on the plasma concentration of human cytokines in transgenic BRGSF-his (humanized immune system) mice suffering from endotoxemia induced by LPS. BRGSF-his mice were administered either PBS (control) or LPS by intraperitoneal injection. The BRGSF-his mice which received LPS first received a pre-treatment by intraperitoneal injection (30 min prior to LPS), consisting either of vehicle (LPS), INO-10F (LPS+10F-10 ug/mL), or a fusion protein between HSA and INO-10F (LPS+HSA-10F-10 ug/mL). Blood samples were collected 8 hours following LPS injection and the plasma concentrations of the following human cytokine/chemokine were assessed: CCL2 (16A), IL-1B (16B), IL-10 (16C), IL-6 (16D), and IL-8 (16E), IP-10 (16F), and TNF-α (16G). p-values were calculated according to a non-parametric t-test between indicated conditions versus LPS alone.
Figure 16B:
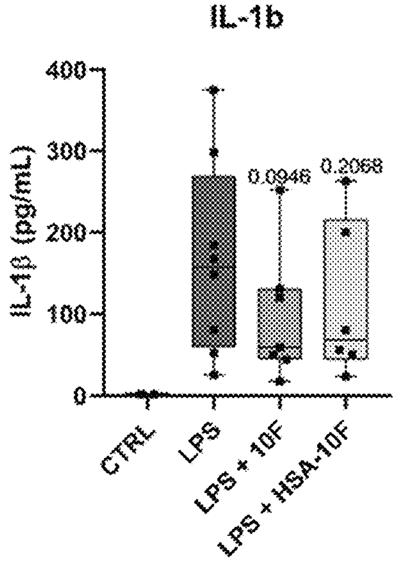
Figure 16C:
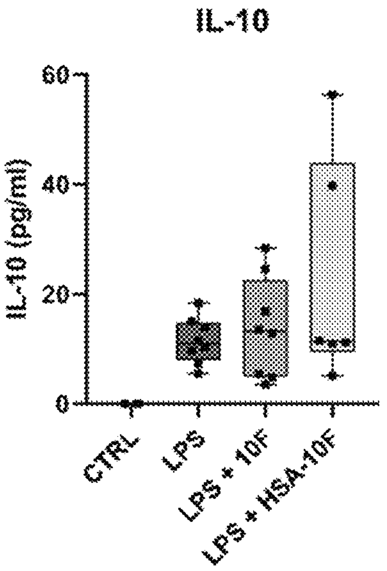
Figure 16D:
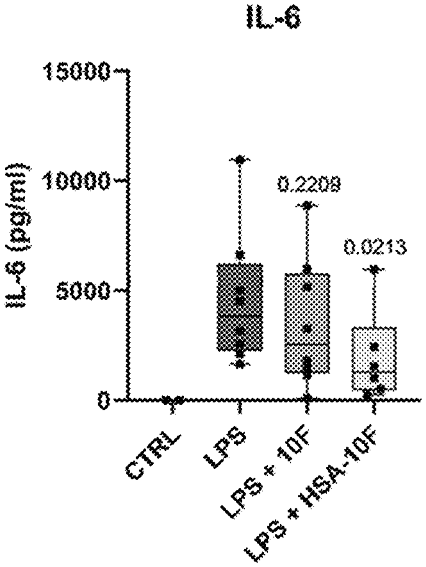
Figure 16E:
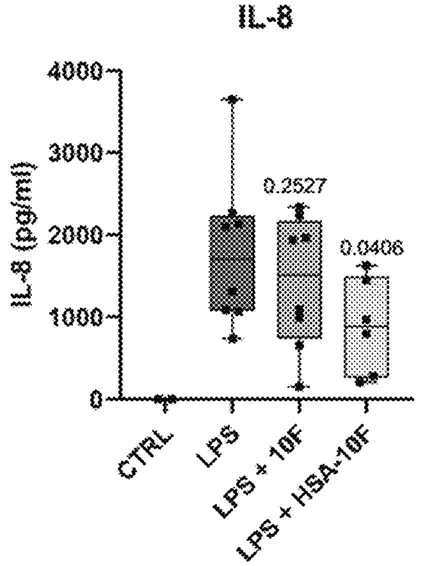
Figure 16F:
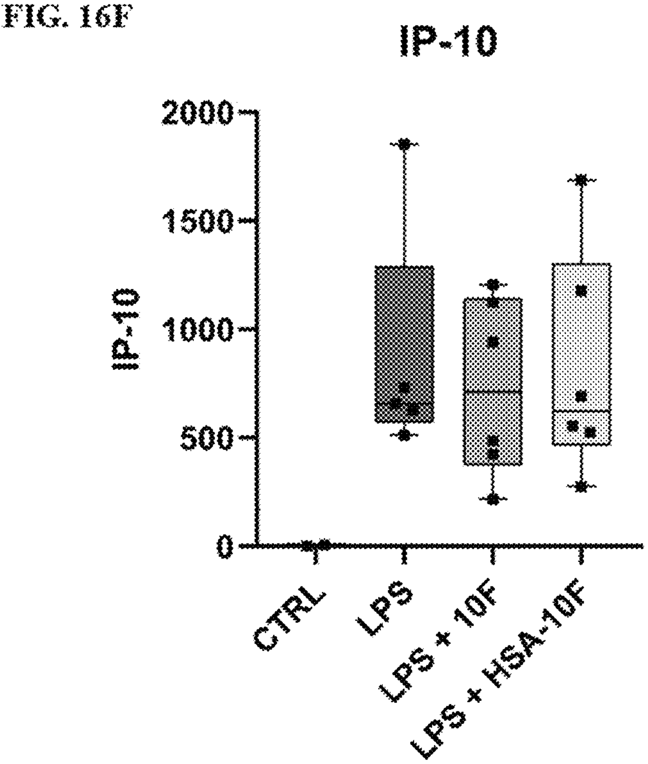
Figure 16G:
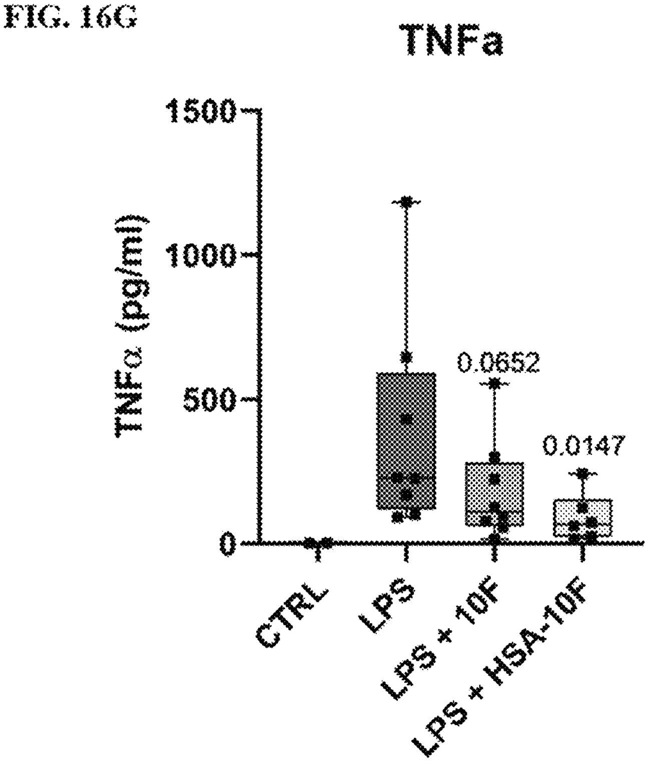

The immuno-modulatory effects of INO-10F were assessed in vivo in transgenic BRGSF mice with a humanized immune system in which endotoxemia was induced by intraperitoneal (i.p.) administration of LPS (8 mg/kg). The mice were randomly divided into four treatment groups to receive either an i.p. administration of PBS (control) alone or LPS with either vehicle, INO-10F, or a fusion protein comprising INO-10F. Indeed, among the mice that were administered LPS, the "LPS" group received a vehicle as treatment, the "LPS+10F" group received an i.p. administration of 10 μg/mL of INO-10F, and the "LPS+HSA-10F" group received an i.p. administration of 10 μg/mL of a format of INO-10F with an extended half-life consisting of a fusion protein between human serum albumin (HSA) and INO-10F (1° F.). Mice were pre-treated with vehicle, INO-10F or HSA-INO-10F (HSA-10F) for 30 minutes, and then administered with LPS to induce endotoxemia. Blood samples were collected 8 hours following LPS injection, and human cytokine/chemokine concentrations were quantified in the plasma (CCL-2, IL-1β, IL-10, IL-6, IL-8, IP-10, and TNF-α). LPS markedly increased the release of the human inflammatory cytokines/chemokines as compared to the control group (CTRL). Interestingly, as shown on FIG. 16, both INO-10F and INO-10F-HSA were able to modulate the secretion of circulating human inflammatory cytokines chemokine ligand 2 (CCL2) also known as monocyte chemoattractant protein 1 or MCP1 (FIG. 16A), interleukin-1β or IL-1β (FIG. 16B), interleukin-10 or IL-10 (FIG. 16C), interleukin-6 or IL-6 (FIG. 16D), interleukin-8 or IL-8 (FIG. 16E), interferon gamma-induced protein 10 (IP-10) also known as C-X-C motif chemokine ligand 10 or CXCL10 (FIG. 16F), and tumor necrosis factor alpha or TNF-α or TNFa (FIG. 16G), with a more pronounced effect for the HSA-INO-10F fusion protein having an extended half-life. These results confirm the immunomodulatory effect of anti-TREM-1 INO-10F Fab fragment in vivo.

Binding of Optimized INO-10F Variants to TREM-1

In order to improve INO-10F binding properties and activity, humanized variants of the anti-TREM-1 INO-10 antibody and corresponding humanized variants of the anti-TREM-1 INO-10F Fab fragment were generated. The humanized variants of the anti-TREM-1 INO-10 antibody were named INO-10-2, INO-10-3, INO-10-4, INO-10-5, and INO-10-6 and the humanized variants of the anti-TREM-1 INO-10F Fab fragment were named INO-10F-2 (F2), INO-10F-3 (F3), INO-10F-4 (F4), INO-10F-5 (F5), and INO-10F-6 (F6). Two additional humanized variants were used as controls: INO-10F-0 (F0), and INO-10F-1 (F1), the humanized anti-TREM-1 Fab fragment with CDRs most similar to INO-10F (CDRs are identical except for one amino acid difference in $V_H$-CDR2). First, the binding affinity constant, association rate and dissociation rate were determined using surface plasmon resonance (SPR) assays. Fab fragments were immobilized on the surface of a CM5 sensor chip followed by injection of increasing concentration of recombinant human TREM-1 or cynomolgus monkeyTREM-1. Results are shown in Table 1 below. No binding to TREM-1 (either hTREM-1 or cTREM-1) was observed with the Fab fragment INO-10F-0 (F0). Fab fragments INO-10F-1 (F1) was only able to bind hTREM-1, with an affinity similar to that of Fab fragment INO-10F. Fab fragments INO-10F-2 to INO-10F-6 (F2 to F6) displayed higher affinities than Fab fragment INO-10F.

TABLE 1

Binding constants $k_a$ or $k_{on}$ (association rate), $k_d$ or $k_{off}$ (dissociation rate) and $K_D$ (equilibrium dissociation constant) for the interaction of human and cynomolgus TREM-1 with different anti-TREM-1 monoclonal antibody Fab fragments

| | | Affinity constants to Human TREM-1 | | | | Affinity constants to cynomolgus TREM-1 | | |
|---|---|---|---|---|---|---|---|---|
| Samples | Replicates | $K_D$ | $k_{on}$ | $k_{off}$ | Replicates | $K_D$ | $K_{on}$ | $k_{off}$ |
| INO-10F | 1 | 7.71E−09 | 1.38E+05 | 1.06E−03 | 1 | 5.79E−8 | 3.57E04 | 2.07E−3 |
| | 2 | 7.89E−09 | 1.37E+05 | 1.08E−03 | 2 | 6.66E−8 | 2.21E4 | 1.47E−3 |
| | Average | 7.80E−09 | 1.38E+05 | 1.07E−03 | Average | 6.22E−8 | 2.89E4 | 1.77E−3 |
| INO-10-F1 | 1 | 5.76E−09 | 1.89E+05 | 1.09E−03 | 1 | No response observed | | |
| | 2 | 7.81E−09 | 1.58E+05 | 1.24E−03 | 2 | | | |
| | Average | 6.79E−09 | 1.74E+05 | 1.17E−03 | Average | | | |
| INO-10-F2 | 1 | 1.29E−09 | 2.29E+05 | 2.97E−04 | 1 | 2.80E−08 | 3.11E+04 | 8.69E−04 |
| | 2 | 1.75E−09 | 1.83E+05 | 3.21E−04 | 2 | 2.85E−08 | 3.16E+04 | 9.00E−04 |
| | Average | 1.52E−09 | 2.06E+05 | 3.09E−04 | Average | 2.83E−08 | 3.14E+04 | 8.85E−04 |
| INO-10-F3 | 1 | 2.61E−10 | 2.03E+05 | 5.31E−05 | 1 | 7.60E−09 | 3.16E+04 | 2.40E−04 |
| | 2 | 3.40E−10 | 2.00E+05 | 6.82E−05 | 2 | 7.68E−09 | 3.19E+04 | 2.45E−04 |
| | Average | 3.01E−10 | 2.02E+05 | 6.07E−05 | Average | 7.64E−09 | 3.18E+04 | 2.43E−04 |

TABLE 1-continued

Binding constants $k_a$ or $k_{on}$ (association rate), $k_d$ or $k_{off}$ (dissociation rate) and $K_D$ (equilibrium dissociation constant) for the interaction of human and cynomolgus TREM-1 with different anti-TREM-1 monoclonal antibody Fab fragments

| | | Affinity constants to Human TREM-1 | | | | Affinity constants to cynomolgus TREM-1 | | |
|---|---|---|---|---|---|---|---|---|
| Samples | Replicates | $K_D$ | $k_{on}$ | $k_{off}$ | Replicates | $K_D$ | $K_{on}$ | $k_{off}$ |
| INO-10-F4 | 1 | 9.61E−10 | 2.17E+05 | 2.09E−04 | 1 | 2.48E−08 | 3.10E+04 | 7.68E−04 |
| | 2 | 1.07E−09 | 2.09E+05 | 2.24E−04 | 2 | 2.44E−08 | 3.17E+04 | 7.74E−04 |
| | Average | 1.02E−09 | 2.13E+05 | 2.17E−04 | Average | 2.46E−08 | 3.14E+04 | 7.71E−04 |
| INO-10-F5 | 1 | 8.84E−10 | 2.04E+05 | 1.80E−04 | 1 | 1.58E−08 | 3.42E+04 | 5.39E−04 |
| | 2 | 5.95E−10 | 2.00E+05 | 1.19E−04 | 2 | 1.57E−08 | 3.47E+04 | 5.45E−04 |
| | Average | 7.40E−10 | 2.02E+05 | 1.50E−04 | Average | 1.58E−08 | 3.45E+04 | 5.42E−04 |
| INO-10-F6 | 1 | 3.89E−09 | 1.24E+05 | 4.81E−04 | 1 | 6.01E−08 | 2.01E+04 | 1.21E−03 |
| | 2 | 4.03E−09 | 1.16E+05 | 4.67E−04 | 2 | 5.34E−08 | 2.49E+04 | 1.33E−03 |
| | Average | 3.96E−09 | 1.20E+05 | 4.74E−04 | Average | 5.68E−08 | 2.25E+04 | 1.27E−03 |

Figure 17A:
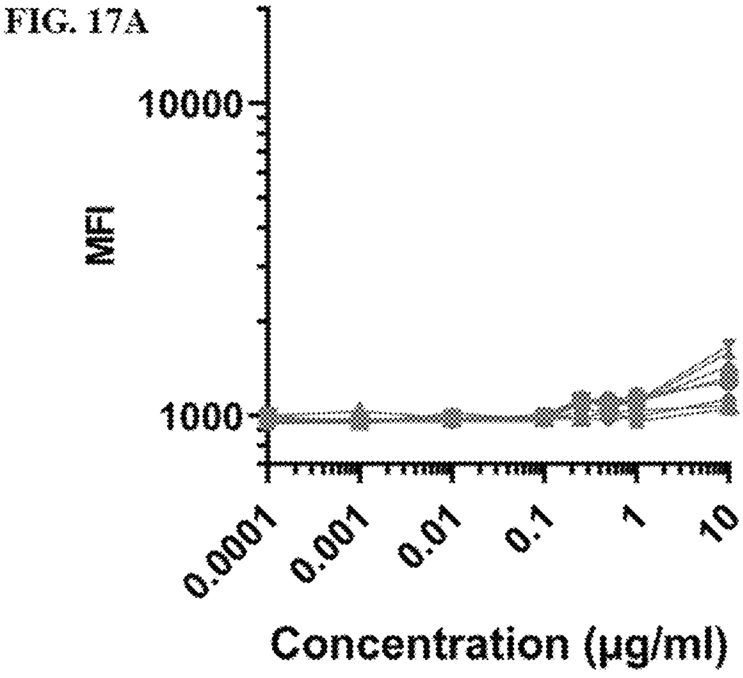
FIGS. 17A-B is a set of graphs showing the binding (assessed by flow cytometry) of anti-TREM-1 Fab INO-10F and of anti-TREM-1 Fab variants INO-10F-0 (F0), INO-10F-1 (F1), INO-10F-2 (F2), INO-10F-3 (F3), INO-10F-4 (F4), INO-10F-5 (F5), and INO-10F-6 (F6) on U937 cells (17A) and on U937-vitD3 cells, i.e., U937 cells pre-treated with vitamin D3 to induce an up-regulation of TREM-1 (17B).
Figure 17B:
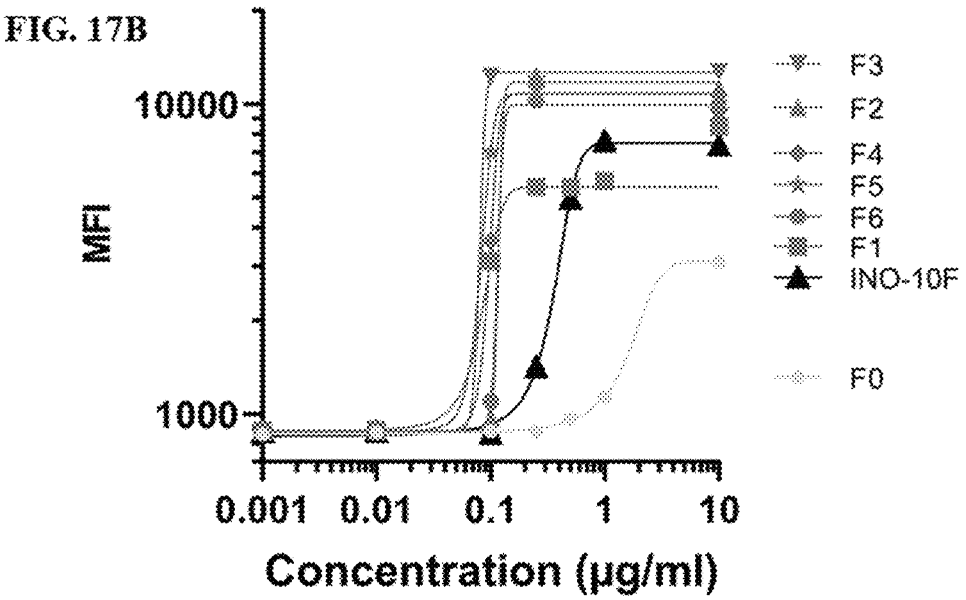

Optimized INO-10F Variants are Able to Inhibit TREM-1 on U937 Cells and Primary Cells The binding of the optimized anti-TREM-1 Fab fragments to human TREM-1 expressed on U937 pre-treated with vitamin D3 (U937-vitD3 cells) and on the untreated control U937 cells was next evaluated. As expected, no binding was observed on U937 cells (FIG. 17A). As shown on FIG. 17B, on U937-vitD3 cells, INO-10F-F0 showed a weak binding at 10 μg/mL, INO-10F showed a similar binding profile as previously obtained (see FIG. 3). A clear shift toward a better affinity was observed for the optimized variants INO-10F-1 to INO-10F-6, corroborating the SPR data (FIG. 17B).

Figure 18:
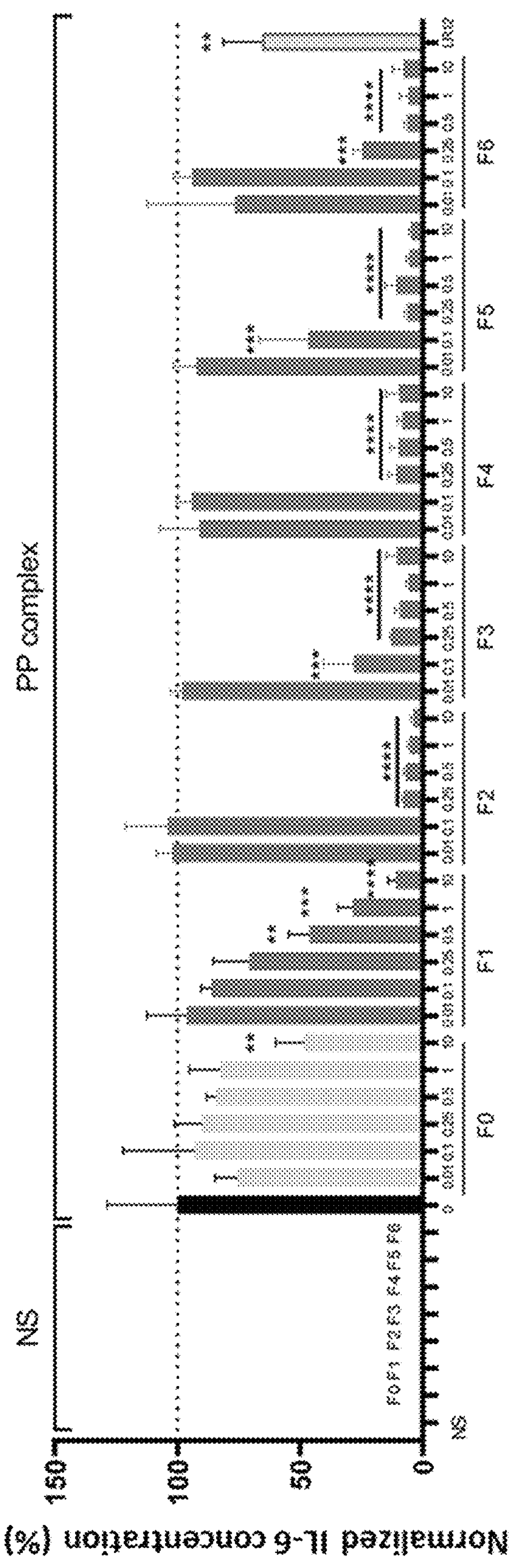
FIG. 18 is a histogram showing the effects of anti-TREM-1 Fab variants INO-10F-0 (F0), INO-10F-1 (F1), INO-10F-2 (F2), INO-10F-3 (F3), INO-10F-4 (F4), INO-10F-5 (F5), and INO-10F-6 (F6) on the production of IL-6 by U937 cells pre-treated with vitamin D3. The concentrations of IL-6 were determined in the supernatants after a 24-hour stimulation of the U937-vitD3 cells in resting conditions (NS) or PP-activated conditions (stimulation with the PP complex corresponding to PGLYRP1 complexed with peptidoglycan) in presence of the anti-TREM-1 Fab variants at the indicated concentrations (0-10 ug/mL). As a positive control, a stimulation with a known TREM-1 inhibitor (peptide LR12) was carried out in PP-activated conditions (LR12). * p<0.05,  p<0.01, * p<0.001, **** p<0.001 versus PP alone.
Figure 19:
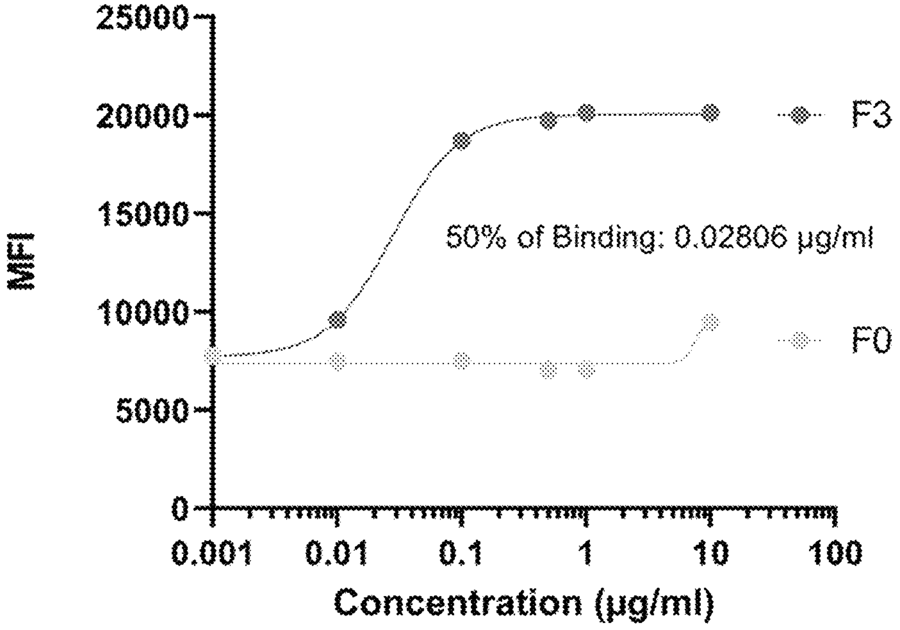
FIG. 19 is a graph comparing the binding (assessed by flow cytometry) of anti-TREM-1 Fab variants INO-10F-3 (F3) and INO-10F-0 (F0) at the indicated concentrations (0.001 to 10 μg/mL) on freshly isolated primary neutrophils.

In accordance with the results obtained with INO-10F, INO-10F-1 (which is the humanized Fab fragment the most similar to INO-10F, with identical CDRs except for one amino acid difference in $V_H$-CDR2) was able to decrease the release of IL-6 by U937-vitD3 cells induced by stimulation with the PGLYRP-1:PGN complex (PP complex) with an approximately 50% inhibition (IC50) achieved at 0.5 μg/mL. INO-10F-0, which showed a decreased affinity to TREM-1 as compared to INO-10F, was associated with a limited decrease of IL-6 release observed only at 10 μg/mL. The improved affinity of INO-10F-2 (F2) to INO-10F-6 (F6) to TREM-1 translated into a shift toward a decrease in the dose required for them to induce a 50% inhibition (IC50) of IL-6 release. In particular, INO-10F-3 (F3) displayed an IC50 around 0.05 μg/mL. The peptide LR12, a known inhibitor of TREM-1, was used as a positive control (FIG. 18). Binding of INO-10F-3 (F3) was confirmed on TREM-1 expressed by freshly isolated human neutrophils with a 50% of binding reached at about 0.03 μg/mL (FIG. 19).

Figure 20:
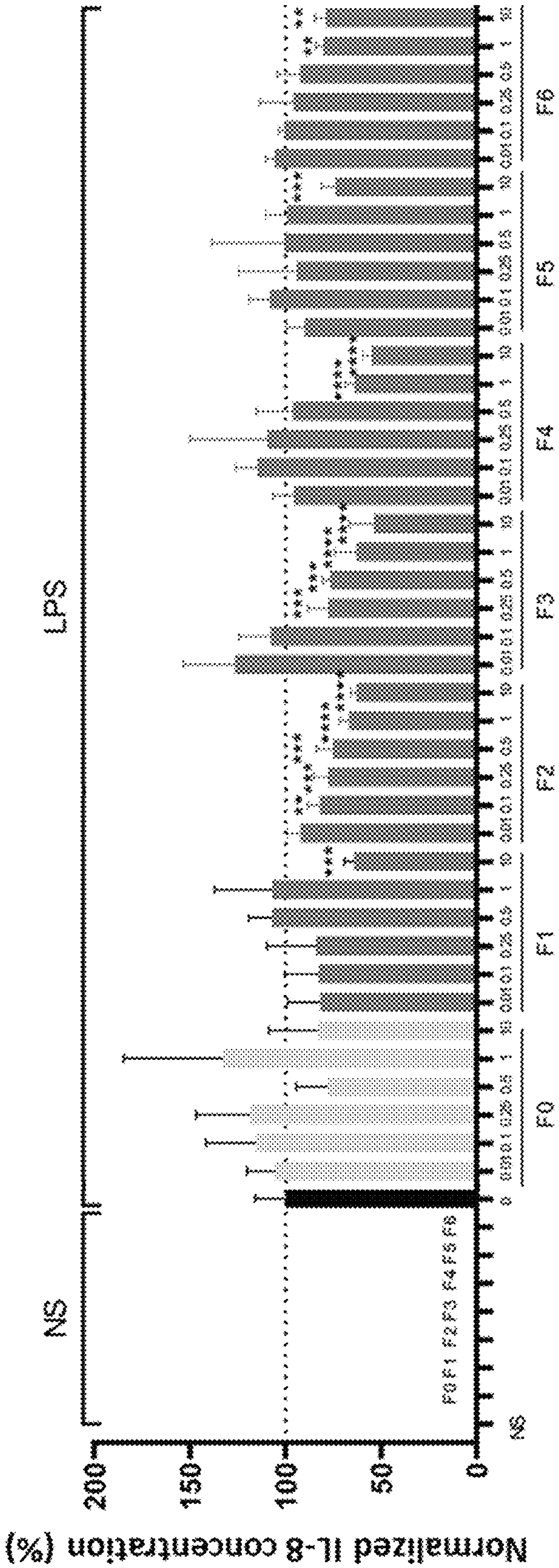
FIG. 20 is a histogram showing the effects of anti-TREM-1 Fab variants INO-10F-0 (F0), INO-10F-1 (F1), INO-10F-2 (F2), INO-10F-3 (F3), INO-10F-4 (F4), INO-10F-5 (F5), and INO-10F-6 (F6) on the production of IL-8 by human primary neutrophils. The concentrations of IL-8 were determined in the supernatants after a 24-hour stimulation of the neutrophils in resting conditions (NS) or LPS-activated conditions in presence of the anti-TREM-1 Fab variants at the indicated concentrations (0-10 ug/mL). As a positive control, a stimulation with a known TREM-1 inhibitor (peptide LR12) was carried out in LPS-activated conditions (LR12). kp<0.05,  p<0.01, * p<0.001, **** p<0.001 versus LPS alone.
Figure 21A:
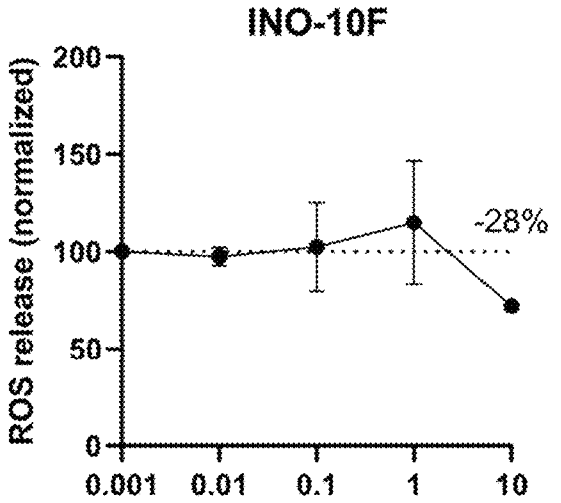
FIGS. 21A-H are a set of graphs showing the effect of anti-TREM-1 Fab INO-10F and of anti-TREM-1 Fab variants on neutrophil intracellular reactive oxygen species (ROS) production. Human primary neutrophils were stimulated for 2 h with LPS (100 ng/mL) in presence of INO-10 Fab (21A) or anti-TREM-1 Fab variants INO-10F-0 or FO (21B), INO-10F-1 or F1 (21C), INO-10F-2 or F2 (21D), INO-10F-3 or F3 (21E), INO-10F-4 or F4 (21F), INO-10F-5 or F5 (21G), and INO-10F-6 or F6 (21H) at the indicated concentrations (0.001-10 ug/mL).
Figure 21B:
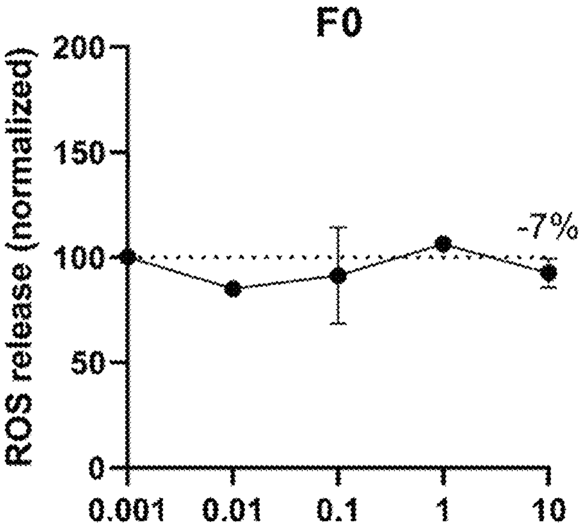
Figure 21C:
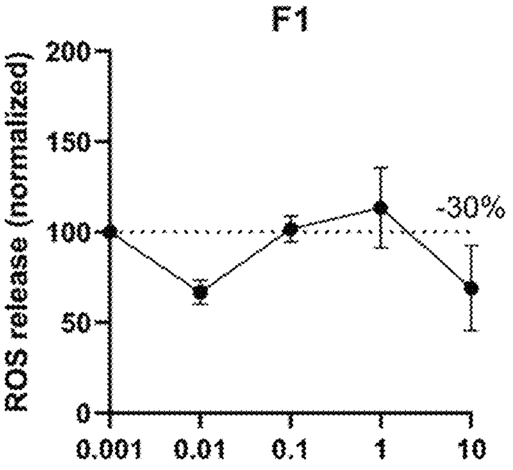
Figure 21D:
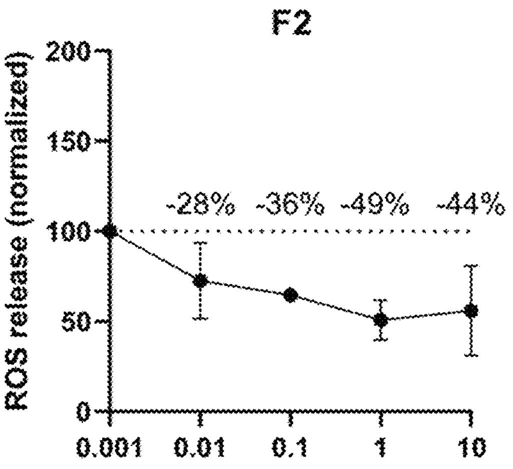
Figure 21E:
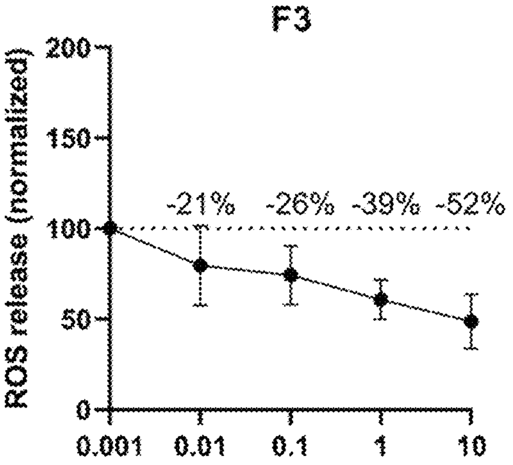
Figure 21F:
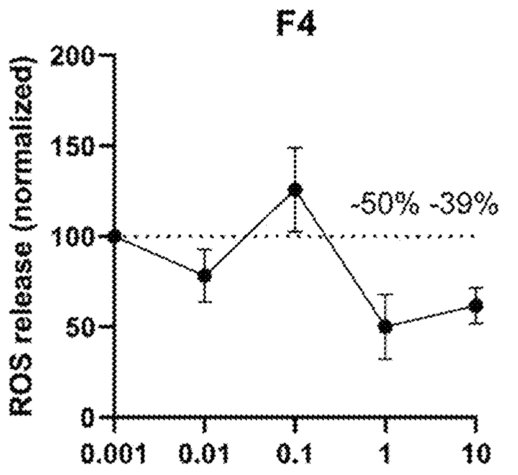
Figure 21G:
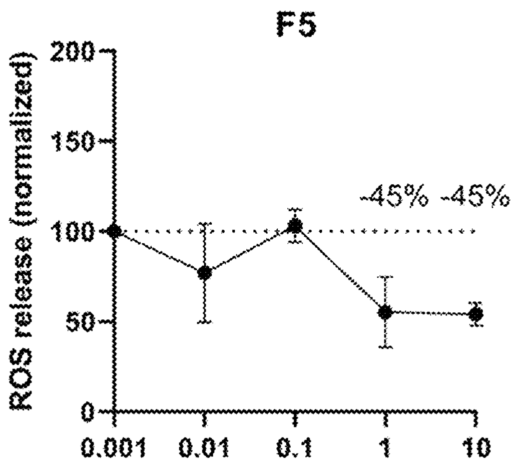
Figure 21H:
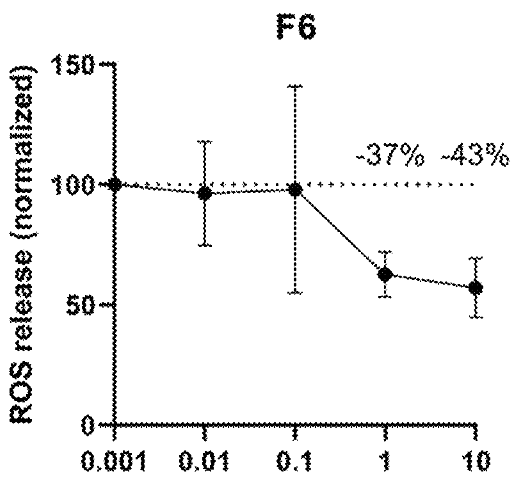

Next, a neutrophil LPS-stimulation assay was conducted to assess the ability of the optimized anti-TREM-1 Fab fragments to decrease the release of IL-8 by human primary neutrophils after stimulation with LPS for 24 hours. As shown on FIG. 20, INO-10F-2 (F2) and INO-10F-3 (F3) showed good significant inhibitory properties between 0.1 and 10 μg/mL. INO-10F-4 (F4) and INO-10F-6 (F6) were also able to significantly decrease IL-8 release when added at 1 μg/mL or 10 μg/mL. INO-10F-1 (F1) and INO-10F-5 (E5) were only able to significantly decrease IL-8 release when added at 10 μg/mL. Finally, a neutrophil LPS-stimulation assay was also conducted to assess the ability of the optimized anti-TREM-1 Fab fragments to decrease the ROS production induced after LPS stimulation of human primary neutrophils for 24 hours. As shown on FIGS. 21A-H, INO-10F-2 (F2) and INO-10F-3 (F3) showed the best inhibitory profile of ROS production by LPS-activated neutrophils. Indeed, INO-10F-2 (F2) inhibited ROS production from 28% at 0.01 μg/mL to 44% at 10 μg/mL (FIG. 21D), and INO-10F-3 (F3) was able to inhibit ROS release from 21% at 0.01 μg/mL to 52% at 10 μg/ml (FIG. 21E). INO-10F-4 (F4) and INO-10F-6 (F6) were also able to inhibit ROS production by LPS-activated neutrophils when added at 1 μg/mL or 10 μg/mL. INO-10F-1 (F1) and INO-10F-5 (F5) were only able to inhibit ROS production by LPS-activated neutrophils when added at 10 μg/mL. As expected, INO-10F-0 (F0) did not inhibit ROS production by LPS-activated neutrophils.

Figure 22A:
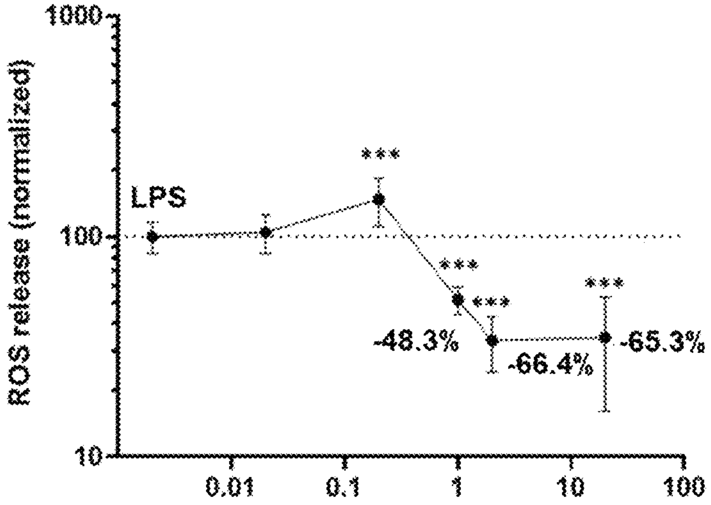
FIGS. 22A-C are a set of graphs showing the effects of an anti-TREM-1 Fab variant (INO-10F-3 coupled with HSA or F3-HSA) on neutrophil intracellular reactive oxygen species (ROS) production. Human primary neutrophils were stimulated for 2 h with LPS (100 ng/mL) (22A) or with the PP complex corresponding to PGLYRP1 (5 ug/mL) complexed with peptidoglycan corresponding to PGN (10 ug/mL) (PP) (22B) or only with peptidoglycan (PGN-10 μg/mL) (22C) in presence of F3-HSA at the indicated concentrations (0.02-20 μg/mL). *p<0.05,  p<0.01, * p<0.001 versus LPS alone (22A), PP alone (22B) or PGN alone (22C) as determined by parametric ANOVA-test.
Figure 22B:
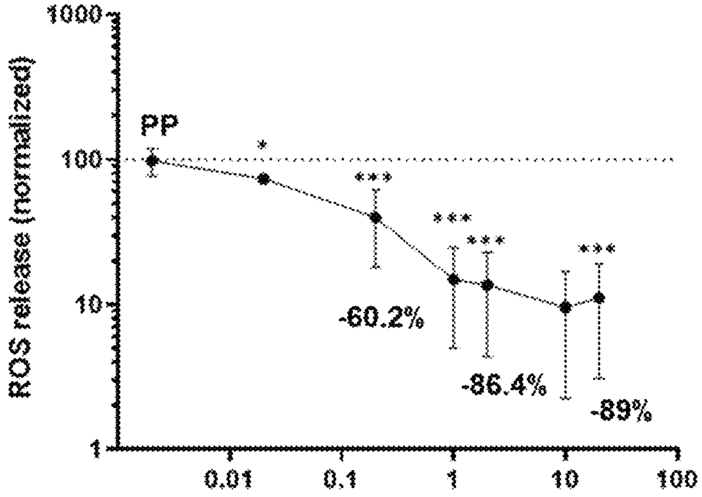
Figure 22C:
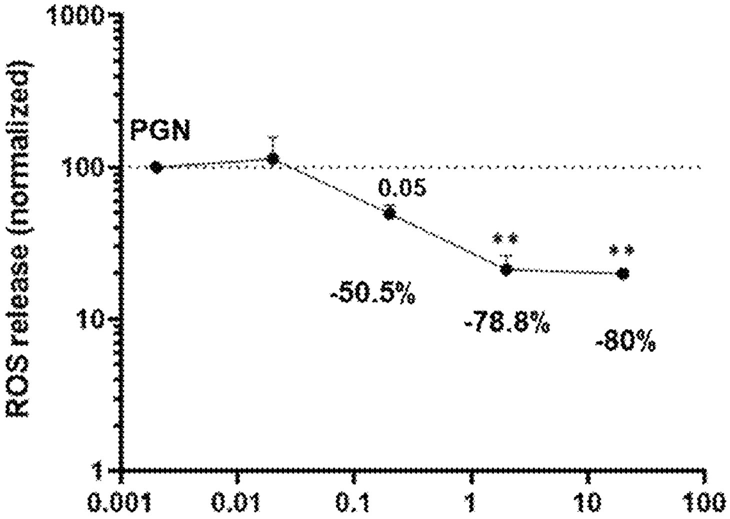

An INO-10F Variant Coupled to HSA is Able to Inhibit TREM-1 on Primary Cells and in Whole Blood Assay A fusion protein consisting of the optimized Fab fragment INO-10F-3 (or F3) coupled with human serum albumin also known as HSA was generated. The inhibitory effect of said fusion protein, referred as F3-HSA, was evaluated on the ROS production by human primary neutrophils (FIG. 22). Human primary neutrophils were thus stimulated for 2 h with LPS (100 ng/mL), or with the PP complex corresponding to PGLYRP1 (5 μg/mL) complexed with peptidoglycan (10 μg/mL) (PP), or with peptidoglycan only (PGN—10 μg/mL) in presence of F3-HSA at the indicated concentrations (0-20 μg/mL). F3-HSA was able to inhibit ROS release after stimulation of the neutrophils with LPS (about 50% decrease at about 1 μg/mL—see FIG. 22A), with PP complex (about 85% decrease at about 1 μg/mL—FIG. 22B), or with PGN alone (about 75% decrease at about 1 μg/mL—FIG. 22C).

Figure 23A:
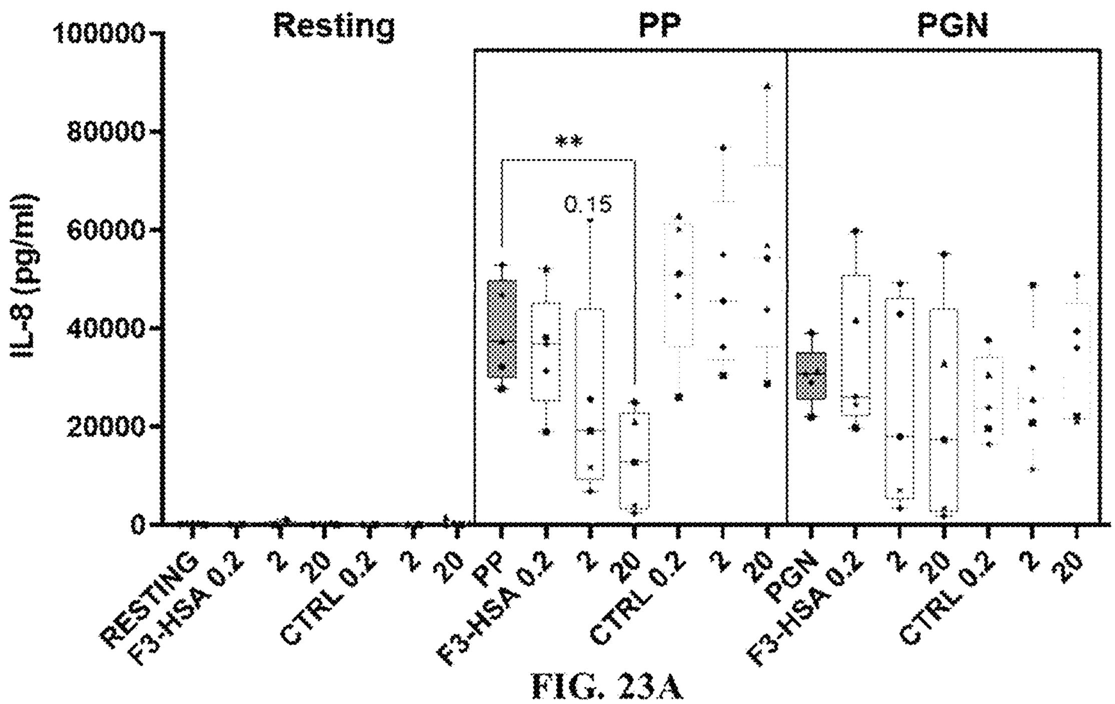
FIGS. 23A-B are a set of box plot showing the effect of an anti-TREM-1 Fab variant (INO-10F-3 coupled with HSA or F3-HSA) on cytokine plasma concentration following a 24-hour whole blood stimulation assay after lysis of red blood cells from 5 healthy donors. F3-HSA or an isotype control (CTLR) was added at the indicated concentrations (0-20 μg/mL) either in resting conditions (NS) or with the PP complex corresponding to PGLYRP1 (5 μg/mL) complexed with peptidoglycan corresponding to PGN (10 μg/mL) (PP) or only with peptidoglycan (PGN-10 μg/mL). After 24 h, the expression of the following cytokines were assessed: IL-8 (23A) and TNF-α (23B). * p<0.05,  p<0.01, * p<0.001 versus PP alone or PGN alone as determined by a non-parametric t-test.
Figure 23B:
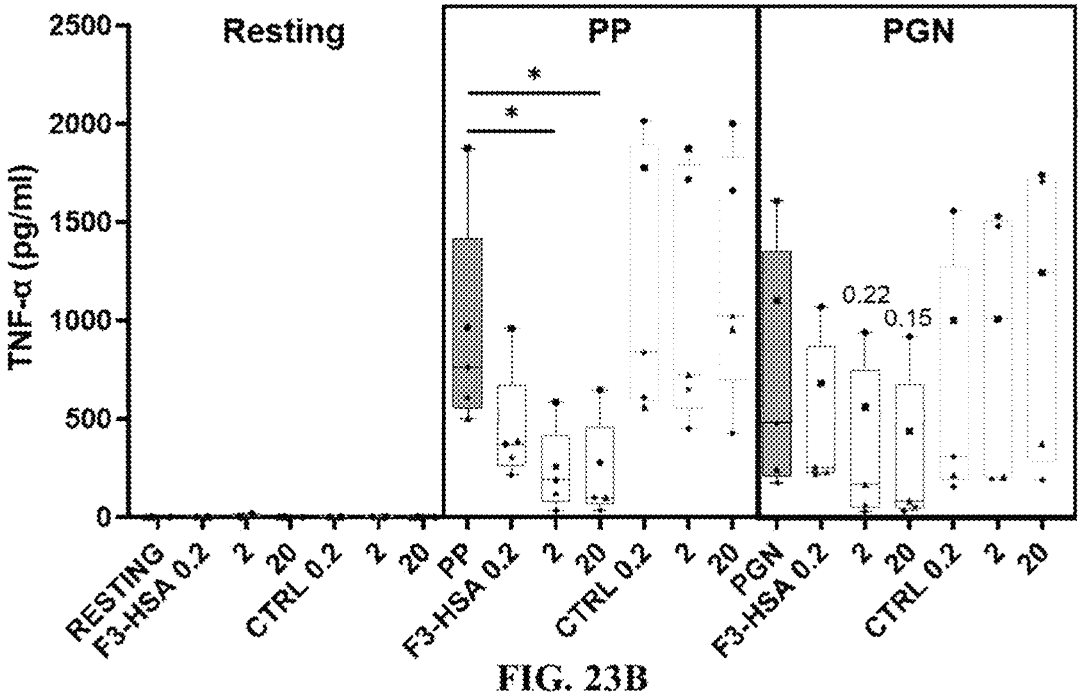

Next, the effect of F3-HSA was assessed on cytokine plasma concentration following a 24-hour whole blood stimulation assay after lysis of red blood cells. F3-HSA or an isotype control (CTLR) were added to whole blood at the indicated concentrations (0-20 μg/mL) either in resting conditions, or in presence of the PP complex corresponding to PGLYRP1 (5 μg/mL) complexed with PGN (10 μg/mL), or in presence of PGN only (10 μg/mL). After 24 h, the expression of the following cytokines were assessed: IL-8 and TNF-α. As shown on FIG. 23, in this assay, F3-HSA reduced, in a dose-dependent manner, the release of both IL-8 and TNF-α, as compared to the control which did not reduce the cytokine release. Indeed, F3-HSA reduced the release of IL-8 after stimulation either with PP or with PGN alone (FIG. 23A), and the release of TNF-α after stimulation either with PP or with PGN alone (FIG. 23B).

Figure 24A:
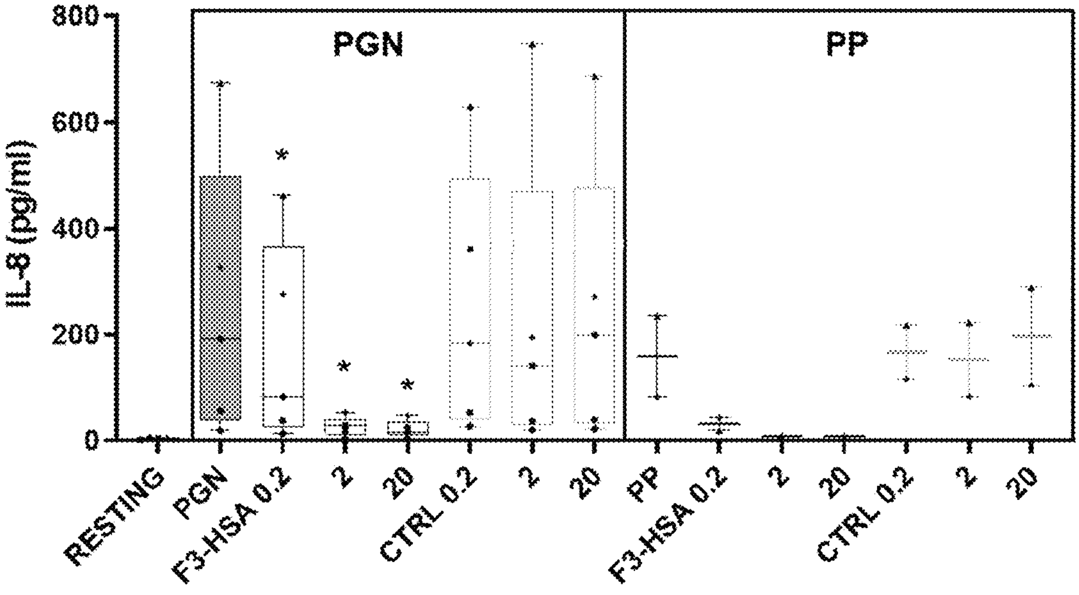
FIGS. 24A-C are a set of histograms showing the effect of an anti-TREM-1 Fab variant (INO-10F-3 coupled with HSA or F3-HSA) on cytokine plasma concentration following a 24-hour cynomolgus whole blood stimulation assay after lysis of red blood cells. F3-HSA or an isotype control (CTRL) was added at the indicated concentrations (0-20 μg/mL) either with the PP complex corresponding to PGLYRP1 (5 μg/mL) complexed with peptidoglycan corresponding to PGN (10 μg/mL) (PP) or only with peptidoglycan (PGN-20 μg/mL). After 24 h, the expression of the following cytokines were assessed: IL-8 (24A), TNF-α (24B) and IL-6 (24C). * p<0.05,  p<0.01, * p<0.001 versus PGN alone as determined by a non-parametric t-test.
Figure 24B:
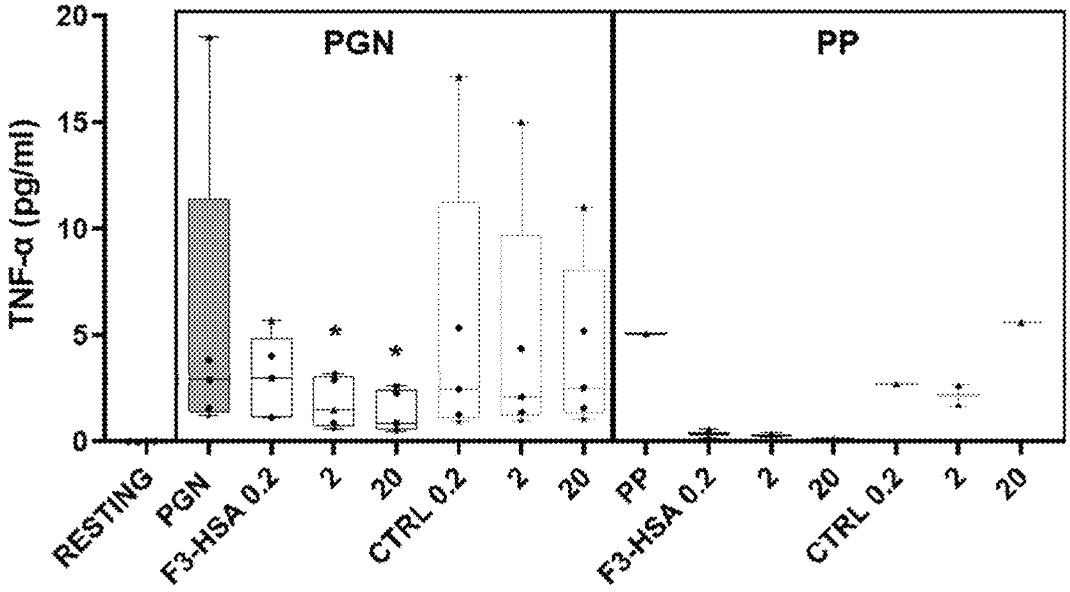
Figure 24C:
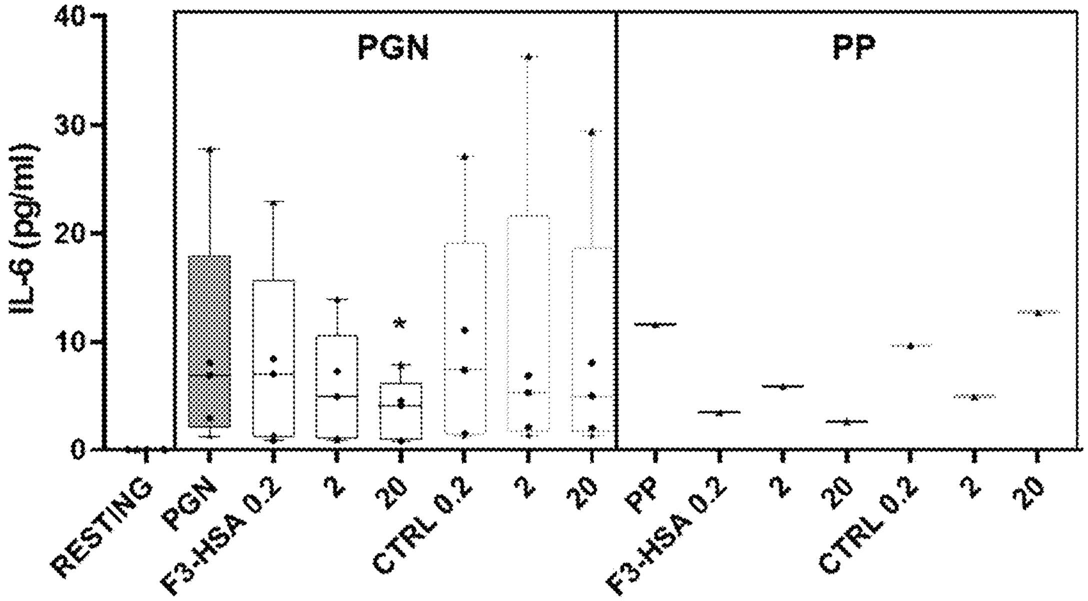

A similar assay was next conducted with cynomolgus whole blood. F3-HSA or an isotype control (CTLR) were thus added to whole blood obtained from healthy cynomolgus donors (*Macaca fascicularis*) at the indicated concentrations (0-20 μg/mL) either in resting conditions, or in presence of the PP complex corresponding to PGLYRP1 (5 μg/mL) complexed with PGN (10 μg/mL), or in presence of PGN only (20 μg/mL). After 24 h, the expression of the following cytokines were assessed: IL-8, TNF-α, and IL-6. As shown on FIG. 24, in this assay, F3-HSA reduced, in a dose-dependent manner, the release of both IL-8, TNF-α, and IL-6, as compared to the control which did not reduce the cytokine release. Indeed, F3-HSA reduced the release of IL-8 after stimulation either with PGN alone or with PP (FIG. 24A), the release of TNF-α after stimulation with PGN alone or with PP (FIG. 24B), and the release of IL-6 after stimulation either with PGN alone or with PP (FIG. 24C).

The invention claimed is:

1. An isolated anti-TREM-1 (Triggering Receptor Expressed on Myeloid cells-1) antibody or an antigen-binding fragment thereof, wherein:

a) the variable region of the heavy chain (VH) of said isolated anti-TREM-1 antibody or antigen-binding fragment thereof comprises the three following complementary-determining regions (CDRs):

$V_H$-CDR1: NTYIH (SEQ ID NO: 1);

$V_H$-CDR2: RIDPA$X_1$G$X_2$TKY$X_3$PKV$X_4$G (SEQ ID NO: 2), wherein $X_1$ is Asn (N) or Gly (G), $X_2$ is Asn (N) or Arg (R), $X_3$ is Ala (A), Asp (D), or Ser(S), $X_4$ is Gln (Q) or Lys (K); and $V_H$-CDR3: H$X_5$G$X_6$TMDY (SEQ ID NO: 3), wherein $X_5$ is Tyr (Y) or Arg (R), $X_6$ is Ser(S) or Gly (G);

b) the variable region of the light chain (VL) of said isolated anti-TREM-1 antibody or antigen-binding fragment thereof comprises the three following CDRs:

$V_L$-CDR1: RASX-SVX;NYGISF$X_9$N (SEQ ID NO: 4), wherein $X_7$ is Glu (E) or Gln (Q), $X_8$ is Asp (D) or Ser(S), $X_9$ is Met (M) or Leu (L); and $V_L$-CDR2: AA$X_{10}X_{11}X_{12}X_{13}X_{14}$ (SEQ ID NO: 5), wherein $X_{10}$ is Ser(S) or Glu (E), $X_{11}$ is Asn (N) or Tyr (Y), $X_{12}$ is Gln (Q) or Arg (R), $X_{13}$ is Gly (G), Ala (A), or Lys (K), $X_{14}$ is Ser(S) or Arg (R); and $V_L$-CDR3: QQS$X_{15}X_{16}X_{17}$P$X_{18}$T (SEQ ID NO: 6), wherein $X_{15}$ is Lys (K), Arg (R), or Ser(S), $X_{16}$ is Glu (E), His (H), or Asn (N), $X_{17}$ is Val (V) or Phe (F), $X_{18}$ is Trp (W) or Tyr (Y).

2. The isolated anti-TREM-1 antibody or antigen-binding fragment thereof according to claim 1, wherein said isolated anti-TREM-1 antibody or antigen-binding fragment thereof comprises the following CDRs:

$V_H$-CDR1: NTYIH (SEQ ID NO: 1), $V_H$-CDR2: RIDPAGGRTKYDPKVKG (SEQ ID NO: 7), $V_H$-CDR3: HYGGTMDY (SEQ ID NO: 8), $V_L$-CDR1: RASESVDNYGISFLN (SEQ ID NO: 9), $V_L$-CDR2: AAEYRGR (SEQ ID NO: 10), and $V_L$-CDR3: QQSRHVPYT (SEQ ID NO: 11); or $V_H$-CDR1: NTYIH (SEQ ID NO: 1), $V_H$-CDR2: RIDPAGGRTKYSPKVQG (SEQ ID NO: 12), $V_H$-CDR3: HRGGTMDY (SEQ ID NO: 13), $V_L$-CDR1: RASQSVSNYGISFLN (SEQ ID NO: 14), $V_L$-CDR2: AASYQKR (SEQ ID NO: 15), and $V_L$-CDR3: QQSSNFPWT (SEQ ID NO: 16); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRGR (SEQ ID NO: 10), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVQG (SEQ ID NO: 19), $V_H$-CDR3: HYGGTMDY (SEQ ID NO: 8), $V_L$-CDR1: RASQSVSNYGISFLN (SEQ ID NO: 14), $V_L$-CDR2: AAEYQGR (SEQ ID NO: 20), and $V_L$-CDR3: QQSSNVPYT (SEQ ID NO: 18); or $V_H$-CDR1: NTYIH (SEQ ID NO: 1), $V_H$-CDR2: RIDPAGGRTKYAPKVKG (SEQ ID NO: 17), $V_H$-CDR3: HRGGTMDY (SEQ ID NO: 13), $V_L$-CDR1: RASQSVSNYGISFLN (SEQ ID NO: 14), $V_L$-CDR2: AAEYRAR (SEQ ID NO: 21), and $V_L$-CDR3: QQSSNVPYT (SEQ ID NO: 18); or $V_H$-CDR1: NTYIH (SEQ ID NO: 1), $V_H$-CDR2: RIDPANGNTKYAPKVQG (SEQ ID NO: 22), $V_H$-CDR3: HYGSTMDY (SEQ ID NO: 23), $V_L$-CDR1: RASESVDNYGISFMN (SEQ ID NO: 24), $V_L$-CDR2: AASNQGS (SEQ ID NO: 25), and $V_L$-CDR3: QQSKEVPWT (SEQ ID NO: 26).

3. The isolated anti-TREM-1 antibody or antigen-binding fragment thereof according to claim 1, wherein said isolated anti-TREM-1 antibody or antigen-binding fragment thereof comprises a variable region of the heavy chain (VH) having a sequence as set forth in any one SEQ ID NO: 27, SEQ ID of NO: 28, SEQ ID NO: 29, SEQ ID NO: 30, SEQ ID NO: 31, and SEQ ID NO: 32, or a sequence having at least 80% identity with any one of SEQ ID NO: 27, SEQ ID NO: 28, SEQ ID NO: 29, SEQ ID NO: 30, SEQ ID NO: 31, and SEQ ID NO: 32.

4. The isolated anti-TREM-1 antibody or antigen-binding fragment thereof according to claim 1, wherein said isolated anti-TREM-1 antibody or antigen-binding fragment thereof comprises a variable region of the light chain (VL) having a sequence as set forth in any one of SEQ NO: ID 33, SEQ ID NO: 34, SEQ ID NO: 35, SEQ ID NO: 36, SEQ ID NO: 37, and SEQ ID NO: 38, or a sequence having at least 80% identity with any one of SEQ ID NO: 33, SEQ ID NO: 34, SEQ ID NO: 35, SEQ ID NO: 36, SEQ ID NO:37, and SEQ ID NO: 38.

5. The isolated anti-TREM-1 antibody or antigen-binding fragment thereof according to claim 1, wherein said isolated anti-TREM-1 antibody or antigen-binding fragment thereof comprises a variable region of the heavy chain (VH) having a sequence as set forth in SEQ ID NO: 27, or a sequence having at least 80% identity with SEQ ID NO: 27, and a variable region of the light chain (VL) having a sequence as set forth in SEQ ID NO: 33, or a sequence having at least 80% identity with SEQ ID NO: 33.

6. The isolated anti-TREM-1 antibody or antigen-binding fragment thereof according to claim 1, wherein said antibody is a monoclonal antibody.

7. The isolated anti-TREM-1 antibody or antigen-binding fragment thereof according to claim 1, wherein said antibody is a humanized antibody or a human antibody.

8. The isolated anti-TREM-1 antibody or antigen-binding fragment thereof according to claim 1, wherein said antibody or antigen-binding fragment thereof is monovalent.

9. The isolated anti-TREM-1 antibody or antigen-binding fragment thereof according to claim 1, wherein the antigen-binding fragment is a Fab, a Fv, or a scFv.

10. A fusion protein comprising the anti-TREM-1 antibody or antigen-binding fragment thereof according to claim 1.

11. A nucleic acid encoding the anti-TREM-1 antibody or antigen-binding fragment thereof according to claim 1, or a fusion protein comprising said anti-TREM-1 antibody or antigen-binding fragment thereof.

12. A pharmaceutical composition comprising the isolated anti-TREM-1 antibody or antigen-binding fragment thereof according to claim 1, or a fusion protein comprising said anti-TREM-1 antibody or antigen-binding fragment thereof, and at least one pharmaceutically acceptable excipient.

13. A medicament comprising the isolated anti-TREM-1 antibody or antigen-binding fragment thereof according to claim 1, or a fusion protein comprising said anti-TREM-1 antibody or antigen-binding fragment thereof.

14. A method for treating a disease selected from an inflammatory or autoimmune disease, a cardiovascular disease, a cancer, and an infectious disease in a subject in need thereof, said method comprising administering to the subject the isolated anti-TREM-1 antibody or antigen-binding fragment thereof according to claim 1, or a fusion protein comprising said anti-TREM-1 antibody or antigen-binding fragment thereof, or a pharmaceutical composition comprising said anti-TREM-1 antibody or antigen-binding fragment thereof or said fusion protein.

15. The method according to claim 14, wherein said inflammatory or autoimmune disease is selected from an inflammatory bowel disease (IBD), Crohn's disease, ulcerative colitis, irritable bowel syndrome, fibrosis, pulmonary fibrosis, liver fibrosis, non-alcoholic steatohepatitis (NASH), alcoholic hepatitis, rheumatoid arthritis, psoriasis, psoriatic arthritis, systemic lupus erythematosus, lupus nephritis, vasculitis, systemic inflammatory response syndrome (SIRS), sepsis, septic shock, type I diabetes, Grave's disease, multiple sclerosis, autoimmune myocarditis, Kawasaki disease, coronary artery disease, chronic obstructive pulmonary disease, interstitial lung disease, autoimmune thyroiditis, scleroderma, systemic sclerosis, osteoarthritis, atopic dermatitis, vitiligo, graft versus host disease, Sjogren's syndrome, autoimmune nephritis, Goodpasture's syndrome, chronic inflammatory demyelinating polyneuropathy, allergy, and asthma.

* * * * *

SEQUENCE LISTING

<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: CDR1 VH

<400> SEQUENCE: 1

Asn Thr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2 VH
<220> FEATURE:
<221> NAME/KEY: SITE
<222> LOCATION: 6
<223> OTHER INFORMATION: X is N or G
<220> FEATURE:
<221> NAME/KEY: SITE
<222> LOCATION: 8
<223> OTHER INFORMATION: X is N or R
<220> FEATURE:
<221> NAME/KEY: SITE
<222> LOCATION: 12
<223> OTHER INFORMATION: X is A, D, or S
<220> FEATURE:
<221> NAME/KEY: SITE
<222> LOCATION: 16
<223> OTHER INFORMATION: X is Q or K

<400> SEQUENCE: 2

Arg Ile Asp Pro Ala Xaa Gly Xaa Thr Lys Tyr Xaa Pro Lys Val Xaa
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: CDR3 VH
<220> FEATURE:
<221> NAME/KEY: SITE
<222> LOCATION: 2
<223> OTHER INFORMATION: X is Y or R
<220> FEATURE:
<221> NAME/KEY: SITE
<222> LOCATION: 4
<223> OTHER INFORMATION: X is S or G

<400> SEQUENCE: 3

His Xaa Gly Xaa Thr Met Asp Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: CDR1 VL
<220> FEATURE:
<221> NAME/KEY: SITE
<222> LOCATION: 4
<223> OTHER INFORMATION: X is E or Q
<220> FEATURE:
<221> NAME/KEY: SITE
<222> LOCATION: 7
<223> OTHER INFORMATION: X is D or S
<220> FEATURE:
<221> NAME/KEY: SITE
<222> LOCATION: 14
<223> OTHER INFORMATION: X is M or L

<400> SEQUENCE: 4

Arg Ala Ser Xaa Ser Val Xaa Asn Tyr Gly Ile Ser Phe Xaa Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDR2 VL
<220> FEATURE:
<221> NAME/KEY: SITE
<222> LOCATION: 3
<223> OTHER INFORMATION: X is S or E
<220> FEATURE:
<221> NAME/KEY: SITE
<222> LOCATION: 4
<223> OTHER INFORMATION: X is N or Y
<220> FEATURE:
<221> NAME/KEY: SITE
<222> LOCATION: 5
<223> OTHER INFORMATION: X is Q or R
<220> FEATURE:
<221> NAME/KEY: SITE
<222> LOCATION: 6
<223> OTHER INFORMATION: X is G, A, or K
<220> FEATURE:
<221> NAME/KEY: SITE
<222> LOCATION: 7
<223> OTHER INFORMATION: X is S or R

<400> SEQUENCE: 5

Ala Ala Xaa Xaa Xaa Xaa Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3 VL
<220> FEATURE:
<221> NAME/KEY: SITE
<222> LOCATION: 4
<223> OTHER INFORMATION: X is K, R, or S
<220> FEATURE:
<221> NAME/KEY: SITE
<222> LOCATION: 5
<223> OTHER INFORMATION: X is E, H, or N
<220> FEATURE:
<221> NAME/KEY: SITE
<222> LOCATION: 6
<223> OTHER INFORMATION: X is V or F
<220> FEATURE:
<221> NAME/KEY: SITE
<222> LOCATION: 8

<223> OTHER INFORMATION: X is W or Y

<400> SEQUENCE: 6

Gln Gln Ser Xaa Xaa Xaa Pro Xaa Thr
1 5

<210> SEQ ID NO 7
<211> LENGTH: 17
<212> TYPE: PRT
<213> ORGANISM: Artificial Sequence
<220> FEATURE:
<223> OTHER INFORMATION: CDR2 VH

<400> SEQUENCE: 7

Arg Ile Asp Pro Ala Gly Gly Arg Thr Lys Tyr Asp Pro Lys Val Lys
1 5 10 15

Gly

<210> SEQ ID NO 8
<211> LENGTH: 8
<212> TYPE: PRT
<213> ORGANISM: Artificial Sequence
<220> FEATURE:
<223> OTHER INFORMATION: CDR3 VH

<400> SEQUENCE: 8

His Tyr Gly Gly Thr Met Asp Tyr
1 5

<210> SEQ ID NO 9
<211> LENGTH: 15
<212> TYPE: PRT
<213> ORGANISM: Artificial Sequence
<220> FEATURE:
<223> OTHER INFORMATION: CDR1 VL

<400> SEQUENCE: 9

Arg Ala Ser Glu Ser Val Asp Asn Tyr Gly Ile Ser Phe Leu Asn
1 5 10 15

<210> SEQ ID NO 10
<211> LENGTH: 7
<212> TYPE: PRT
<213> ORGANISM: Artificial Sequence
<220> FEATURE:
<223> OTHER INFORMATION: CDR2 VL

<400> SEQUENCE: 10

Ala Ala Glu Tyr Arg Gly Arg
1 5

<210> SEQ ID NO 11
<211> LENGTH: 9
<212> TYPE: PRT
<213> ORGANISM: Artificial Sequence
<220> FEATURE:
<223> OTHER INFORMATION: CDR3 VL

<400> SEQUENCE: 11

Gln Gln Ser Arg His Val Pro Tyr Thr
1 5

<210> SEQ ID NO 12
<211> LENGTH: 17
<212> TYPE: PRT
<213> ORGANISM: Artificial Sequence

<220> FEATURE:
<223> OTHER INFORMATION: CDR2 VH

<400> SEQUENCE: 12

Arg Ile Asp Pro Ala Gly Gly Arg Thr Lys Tyr Ser Pro Lys Val Gln
1 5 10 15

Gly

<210> SEQ ID NO 13
<211> LENGTH: 8
<212> TYPE: PRT
<213> ORGANISM: Artificial Sequence
<220> FEATURE:
<223> OTHER INFORMATION: CDR3 VH

<400> SEQUENCE: 13

His Arg Gly Gly Thr Met Asp Tyr
1 5

<210> SEQ ID NO 14
<211> LENGTH: 15
<212> TYPE: PRT
<213> ORGANISM: Artificial Sequence
<220> FEATURE:
<223> OTHER INFORMATION: CDR1 VL

<400> SEQUENCE: 14

Arg Ala Ser Gln Ser Val Ser Asn Tyr Gly Ile Ser Phe Leu Asn
1 5 10 15

<210> SEQ ID NO 15
<211> LENGTH: 7
<212> TYPE: PRT
<213> ORGANISM: Artificial Sequence
<220> FEATURE:
<223> OTHER INFORMATION: CDR2 VL

<400> SEQUENCE: 15

Ala Ala Ser Tyr Gln Lys Arg
1 5

<210> SEQ ID NO 16
<211> LENGTH: 9
<212> TYPE: PRT
<213> ORGANISM: Artificial Sequence
<220> FEATURE:
<223> OTHER INFORMATION: CDR3 VL

<400> SEQUENCE: 16

Gln Gln Ser Ser Asn Phe Pro Trp Thr
1 5

<210> SEQ ID NO 17
<211> LENGTH: 17
<212> TYPE: PRT
<213> ORGANISM: Artificial Sequence
<220> FEATURE:
<223> OTHER INFORMATION: CDR2 VH

<400> SEQUENCE: 17

Arg Ile Asp Pro Ala Gly Gly Arg Thr Lys Tyr Ala Pro Lys Val Lys
1 5 10 15

Gly

<210> SEQ ID NO 18

<211> LENGTH: 9
<212> TYPE: PRT
<213> ORGANISM: Artificial Sequence
<220> FEATURE:
<223> OTHER INFORMATION: CDR3 VL

<400> SEQUENCE: 18

Gln Gln Ser Ser Asn Val Pro Tyr Thr
1 5

<210> SEQ ID NO 19
<211> LENGTH: 17
<212> TYPE: PRT
<213> ORGANISM: Artificial Sequence
<220> FEATURE:
<223> OTHER INFORMATION: CDR2 VH

<400> SEQUENCE: 19

Arg Ile Asp Pro Ala Gly Gly Arg Thr Lys Tyr Ala Pro Lys Val Gln
1 5 10 15

Gly

<210> SEQ ID NO 20
<211> LENGTH: 7
<212> TYPE: PRT
<213> ORGANISM: Artificial Sequence
<220> FEATURE:
<223> OTHER INFORMATION: CDR2 VL

<400> SEQUENCE: 20

Ala Ala Glu Tyr Gln Gly Arg
1 5

<210> SEQ ID NO 21
<211> LENGTH: 7
<212> TYPE: PRT
<213> ORGANISM: Artificial Sequence
<220> FEATURE:
<223> OTHER INFORMATION: CDR2 VL

<400> SEQUENCE: 21

Ala Ala Glu Tyr Arg Ala Arg
1 5

<210> SEQ ID NO 22
<211> LENGTH: 17
<212> TYPE: PRT
<213> ORGANISM: Artificial Sequence
<220> FEATURE:
<223> OTHER INFORMATION: CDR2 VH

<400> SEQUENCE: 22

Arg Ile Asp Pro Ala Asn Gly Asn Thr Lys Tyr Ala Pro Lys Val Gln
1 5 10 15

Gly

<210> SEQ ID NO 23
<211> LENGTH: 8
<212> TYPE: PRT
<213> ORGANISM: Artificial Sequence
<220> FEATURE:
<223> OTHER INFORMATION: CDR3 VH

<400> SEQUENCE: 23

His Tyr Gly Ser Thr Met Asp Tyr
1 5

<210> SEQ ID NO 24
<211> LENGTH: 15
<212> TYPE: PRT
<213> ORGANISM: Artificial Sequence
<220> FEATURE:
<223> OTHER INFORMATION: CDR1 VL

<400> SEQUENCE: 24

```
Arg Ala Ser Glu Ser Val Asp Asn Tyr Gly Ile Ser Phe Met Asn
1               5                   10                  15
```

<210> SEQ ID NO 25
<211> LENGTH: 7
<212> TYPE: PRT
<213> ORGANISM: Artificial Sequence
<220> FEATURE:
<223> OTHER INFORMATION: CDR2 VL

<400> SEQUENCE: 25

```
Ala Ala Ser Asn Gln Gly Ser
1               5
```

<210> SEQ ID NO 26
<211> LENGTH: 9
<212> TYPE: PRT
<213> ORGANISM: Artificial Sequence
<220> FEATURE:
<223> OTHER INFORMATION: CDR3 VL

<400> SEQUENCE: 26

```
Gln Gln Ser Lys Glu Val Pro Trp Thr
1               5
```

<210> SEQ ID NO 27
<211> LENGTH: 117
<212> TYPE: PRT
<213> ORGANISM: Artificial Sequence
<220> FEATURE:
<223> OTHER INFORMATION: VH

<400> SEQUENCE: 27

```
Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Asn Ile Asp Asn Thr
            20                  25                  30

Tyr Ile His Trp Val Arg Gln Ala Pro Gly Lys Gly Leu Glu Trp Ile
        35                  40                  45

Gly Arg Ile Asp Pro Ala Gly Gly Arg Thr Lys Tyr Asp Pro Lys Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Gly His Tyr Gly Gly Thr Met Asp Tyr Trp Gly Gln Gly Thr Leu
            100                 105                 110

Val Thr Val Ser Ser
        115
```

<210> SEQ ID NO 28
<211> LENGTH: 117
<212> TYPE: PRT
<213> ORGANISM: Artificial Sequence

<220> FEATURE:
<223> OTHER INFORMATION: VH

<400> SEQUENCE: 28

Glu Val Gln Leu Val Glu Ser Gly Gly Ala Leu Val Lys Pro Gly Gly
1 5 10 15

Ser Leu Arg Leu Ser Cys Ala Ala Ser Gly Phe Asn Ile Gly Asn Thr
20 25 30

Tyr Ile His Trp Val Arg Gln Ala Pro Gly Lys Gly Leu Glu Trp Ile
35 40 45

Gly Arg Ile Asp Pro Ala Gly Gly Arg Thr Lys Tyr Ser Pro Lys Val
50 55 60

Gln Gly Arg Phe Thr Ile Ser Ala Pro Thr Ser Lys Asn Thr Ala Tyr
65 70 75 80

Leu Gln Met Asn Ser Leu Lys Thr Glu Asp Thr Ala Val Tyr Tyr Cys
85 90 95

Thr Gly His Arg Gly Gly Thr Met Asp Tyr Trp Gly Gln Gly Thr Leu
100 105 110

Val Thr Val Ser Ser
115

<210> SEQ ID NO 29
<211> LENGTH: 117
<212> TYPE: PRT
<213> ORGANISM: Artificial Sequence
<220> FEATURE:
<223> OTHER INFORMATION: VH

<400> SEQUENCE: 29

Glu Val Gln Leu Val Glu Ser Gly Gly Ala Leu Val Lys Pro Gly Gly
1 5 10 15

Ser Leu Arg Leu Ser Cys Ala Ala Ser Gly Phe Asn Ile Gly Asn Thr
20 25 30

Tyr Ile His Trp Val Arg Gln Ala Pro Gly Lys Gly Leu Glu Trp Val
35 40 45

Gly Arg Ile Asp Pro Ala Gly Gly Arg Thr Lys Tyr Ala Pro Lys Val
50 55 60

Lys Gly Arg Phe Thr Ile Ser Ala Asp Asp Ser Lys Asn Thr Ala Tyr
65 70 75 80

Leu Gln Met Asn Ser Leu Lys Thr Glu Asp Thr Ala Val Tyr Tyr Cys
85 90 95

Thr Gly His Arg Gly Gly Thr Met Asp Tyr Trp Gly Gln Gly Thr Leu
100 105 110

Val Thr Val Ser Ser
115

<210> SEQ ID NO 30
<211> LENGTH: 117
<212> TYPE: PRT
<213> ORGANISM: Artificial Sequence
<220> FEATURE:
<223> OTHER INFORMATION: VH

<400> SEQUENCE: 30

Glu Val Gln Leu Val Glu Ser Gly Gly Ala Leu Val Lys Pro Gly Gly
1 5 10 15

Ser Leu Arg Leu Ser Cys Ala Ala Ser Gly Phe Asn Ile Gly Asn Thr
20 25 30

```
Tyr Ile His Trp Val Arg Gln Ala Pro Gly Lys Gly Leu Glu Trp Ile
        35                  40                  45

Gly Arg Ile Asp Pro Ala Gly Gly Arg Thr Lys Tyr Ala Pro Lys Val
    50                  55                  60

Gln Gly Arg Phe Thr Ile Ser Ala Asp Thr Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Thr Gly His Tyr Gly Gly Thr Met Asp Tyr Trp Gly Gln Gly Thr Leu
            100                 105                 110

Val Thr Val Ser Ser
        115


<210> SEQ ID NO 31
<211> LENGTH: 117
<212> TYPE: PRT
<213> ORGANISM: Artificial Sequence
<220> FEATURE:
<223> OTHER INFORMATION: VH

<400> SEQUENCE: 31

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Asn Ile Gly Asn Thr
            20                  25                  30

Tyr Ile His Trp Val Arg Gln Ala Pro Gly Lys Gly Leu Glu Trp Val
        35                  40                  45

Gly Arg Ile Asp Pro Ala Gly Gly Arg Thr Lys Tyr Ala Pro Lys Val
    50                  55                  60

Lys Gly Arg Phe Thr Ile Ser Ala Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Gly His Arg Gly Gly Thr Met Asp Tyr Trp Gly Gln Gly Thr Leu
            100                 105                 110

Val Thr Val Ser Ser
        115


<210> SEQ ID NO 32
<211> LENGTH: 117
<212> TYPE: PRT
<213> ORGANISM: Artificial Sequence
<220> FEATURE:
<223> OTHER INFORMATION: VH

<400> SEQUENCE: 32

Glu Val Gln Leu Val Glu Ser Gly Gly Ala Leu Val Lys Pro Gly Gly
1               5                   10                  15

Ser Leu Arg Leu Ser Cys Ala Ala Ser Gly Phe Asn Ile Lys Asn Thr
            20                  25                  30

Tyr Ile His Trp Val Arg Gln Ala Pro Gly Lys Gly Leu Glu Trp Ile
        35                  40                  45

Gly Arg Ile Asp Pro Ala Asn Gly Asn Thr Lys Tyr Ala Pro Lys Val
    50                  55                  60

Gln Gly Arg Phe Thr Ile Ser Ala Asp Thr Ser Lys Asn Thr Ala Tyr
65                  70                  75                  80

Leu Gln Met Asn Ser Leu Lys Thr Glu Asp Thr Ala Val Tyr Tyr Cys
                85                  90                  95
```

```
Thr Gly His Tyr Gly Ser Thr Met Asp Tyr Trp Gly Gln Gly Thr Leu
            100                 105                 110

Val Thr Val Ser Ser
        115


<210> SEQ ID NO 33
<211> LENGTH: 111
<212> TYPE: PRT
<213> ORGANISM: Artificial Sequence
<220> FEATURE:
<223> OTHER INFORMATION: VL

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Leu Asn Trp Tyr Gln Gln Lys Pro Gly Gln Ala Pro
        35                  40                  45

Arg Leu Leu Ile Tyr Ala Ala Glu Tyr Arg Gly Arg Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Arg
                85                  90                  95

His Val Pro Tyr Thr Phe Gly Gln Gly Thr Lys Val Glu Ile Lys
            100                 105                 110


<210> SEQ ID NO 34
<211> LENGTH: 111
<212> TYPE: PRT
<213> ORGANISM: Artificial Sequence
<220> FEATURE:
<223> OTHER INFORMATION: VL

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Gly Ile Ser Phe Leu Asn Trp Tyr Gln Gln Lys Pro Gly Gln Ala Pro
        35                  40                  45

Arg Leu Leu Ile Tyr Ala Ala Ser Tyr Gln Lys Arg Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ser
                85                  90                  95

Asn Phe Pro Trp Thr Phe Gly Gln Gly Thr Lys Val Glu Ile Lys
            100                 105                 110


<210> SEQ ID NO 35
<211> LENGTH: 111
<212> TYPE: PRT
<213> ORGANISM: Artificial Sequence
<220> FEATURE:
<223> OTHER INFORMATION: VL

<400> SEQUENCE: 35
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Gly Ile Ser Phe Leu Asn Trp Tyr Gln Gln Lys Pro Gly Gln Ala Pro
        35                  40                  45

Arg Leu Leu Ile Tyr Ala Ala Glu Tyr Arg Gly Arg Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ser
                85                  90                  95

Asn Val Pro Tyr Thr Phe Gly Gln Gly Thr Lys Val Glu Ile Lys
            100                 105                 110


<210> SEQ ID NO 36
<211> LENGTH: 111
<212> TYPE: PRT
<213> ORGANISM: Artificial Sequence
<220> FEATURE:
<223> OTHER INFORMATION: VL

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Gly Ile Ser Phe Leu Asn Trp Tyr Gln Gln Lys Pro Gly Gln Ala Pro
        35                  40                  45

Arg Leu Leu Ile Tyr Ala Ala Glu Tyr Gln Gly Arg Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ser
                85                  90                  95

Asn Val Pro Tyr Thr Phe Gly Gln Gly Thr Lys Leu Glu Ile Lys
            100                 105                 110


<210> SEQ ID NO 37
<211> LENGTH: 111
<212> TYPE: PRT
<213> ORGANISM: Artificial Sequence
<220> FEATURE:
<223> OTHER INFORMATION: VL

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Gly Ile Ser Phe Leu Asn Trp Tyr Gln Gln Lys Pro Gly Gln Ala Pro
        35                  40                  45

Arg Leu Leu Ile Tyr Ala Ala Glu Tyr Arg Ala Arg Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Ser
                85                  90                  95
```

```
Asn Val Pro Tyr Thr Phe Gly Gln Gly Thr Lys Val Glu Ile Lys
            100                 105                 110


<210> SEQ ID NO 38
<211> LENGTH: 111
<212> TYPE: PRT
<213> ORGANISM: Artificial Sequence
<220> FEATURE:
<223> OTHER INFORMATION: VL

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Ile Ser Phe Met Asn Trp Phe Gln Gln Lys Pro Gly Gln Ala Pro
        35                  40                  45

Arg Leu Leu Ile Tyr Ala Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Trp Thr Phe Gly Gln Gly Thr Lys Val Glu Ile Lys
            100                 105                 110


<210> SEQ ID NO 39
<211> LENGTH: 17
<212> TYPE: PRT
<213> ORGANISM: Artificial Sequence
<220> FEATURE:
<223> OTHER INFORMATION: CDR2 VH
<220> FEATURE:
<221> NAME/KEY: SITE
<222> LOCATION: 6
<223> OTHER INFORMATION: X is N or G
<220> FEATURE:
<221> NAME/KEY: SITE
<222> LOCATION: 8
<223> OTHER INFORMATION: X is N or R
<220> FEATURE:
<221> NAME/KEY: SITE
<222> LOCATION: 12
<223> OTHER INFORMATION: X is A, D, or S
<220> FEATURE:
<221> NAME/KEY: SITE
<222> LOCATION: 16
<223> OTHER INFORMATION: X is Q or K

<400> SEQUENCE: 39

Arg Ile Asp Pro Ala Xaa Gly Xaa Thr Lys Tyr Xaa Pro Lys Phe Xaa
1               5                   10                  15

Gly


<210> SEQ ID NO 40
<211> LENGTH: 17
<212> TYPE: PRT
<213> ORGANISM: Artificial Sequence
<220> FEATURE:
<223> OTHER INFORMATION: CDR2 VH

<400> SEQUENCE: 40

Arg Ile Asp Pro Ala Asn Gly Asn Thr Lys Tyr Ala Pro Lys Phe Gln
1               5                   10                  15
```

Gly

<210> SEQ ID NO 41
<211> LENGTH: 117
<212> TYPE: PRT
<213> ORGANISM: Artificial Sequence
<220> FEATURE:
<223> OTHER INFORMATION: VH

<400> SEQUENCE: 41

```
Ala Val Gln Leu Gln Gln Ser Val Ala Ala Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Gly Lys Ala Thr Ile Thr Ala Asp Thr Ser Ser Asp Thr Ala Tyr
65                  70                  75                  80

Leu Gln Leu Ser Ser Leu Thr Ser Asp Asp Thr Ala Ile Tyr Tyr Cys
                85                  90                  95

Thr Gly His Tyr Gly Ser Thr Met Asp Tyr Trp Gly Gln Gly Thr Ser
            100                 105                 110

Val Thr Val Ser Ser
        115
```

<210> SEQ ID NO 42
<211> LENGTH: 111
<212> TYPE: PRT
<213> ORGANISM: Artificial Sequence
<220> FEATURE:
<223> OTHER INFORMATION: VL

<400> SEQUENCE: 42

```
Glu Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Thr Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Asp Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110
```

<210> SEQ ID NO 43
<211> LENGTH: 234
<212> TYPE: PRT
<213> ORGANISM: Homo sapiens
<220> FEATURE:
<223> OTHER INFORMATION: TREM-1

<400> SEQUENCE: 43

```
Met Arg Lys Thr Arg Leu Trp Gly Leu Leu Trp Met Leu Phe Val Ser
1               5                   10                  15
```

```
Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
        195                 200                 205

Leu Leu Ala Gly Gly Phe Leu Ser Lys Ser Leu Val Phe Ser Val Leu
    210                 215                 220

Phe Ala Val Thr Leu Arg Ser Phe Val Pro
225                 230
```

<210> SEQ ID NO 44
<211> LENGTH: 150
<212> TYPE: PRT
<213> ORGANISM: Homo sapiens
<220> FEATURE:
<223> OTHER INFORMATION: TREM-1

<400> SEQUENCE: 44

```
Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Arg Cys Ser Thr Leu Ser Phe
    130                 135                 140
```

Ser Trp Leu Val Asp Ser
145 150

<210> SEQ ID NO 45
<211> LENGTH: 225
<212> TYPE: PRT
<213> ORGANISM: Homo sapiens
<220> FEATURE:
<223> OTHER INFORMATION: TREM-1

<400> SEQUENCE: 45

Met Arg Lys Thr Arg Leu Trp Gly Leu Leu Trp Met Leu Phe Val Ser
1 5 10 15

Glu Leu Arg Ala Ala Thr Lys Leu Thr Glu Glu Lys Tyr Glu Leu Lys
20 25 30

Glu Gly Gln Thr Leu Asp Val Lys Cys Asp Tyr Thr Leu Glu Lys Phe
35 40 45

Ala Ser Ser Gln Lys Ala Trp Gln Ile Ile Arg Asp Gly Glu Met Pro
50 55 60

Lys Thr Leu Ala Cys Thr Glu Arg Pro Ser Lys Asn Ser His Pro Val
65 70 75 80

Gln Val Gly Arg Ile Ile Leu Glu Asp Tyr His Asp His Gly Leu Leu
85 90 95

Arg Val Arg Met Val Asn Leu Gln Val Glu Asp Ser Gly Leu Tyr Gln
100 105 110

Cys Val Ile Tyr Gln Pro Pro Lys Glu Pro His Met Leu Phe Asp Arg
115 120 125

Ile Arg Leu Val Val Thr Lys Gly Phe Ser Gly Thr Pro Gly Ser Asn
130 135 140

Glu Asn Ser Thr Gln Asn Val Tyr Lys Ile Pro Pro Thr Thr Thr Lys
145 150 155 160

Ala Leu Cys Pro Leu Tyr Thr Ser Pro Arg Thr Val Thr Gln Ala Pro
165 170 175

Pro Lys Ser Thr Ala Asp Val Ser Thr Pro Asp Ser Glu Ile Asn Leu
180 185 190

Thr Asn Val Thr Asp Ile Ile Arg Tyr Ser Phe Gln Val Pro Gly Pro
195 200 205

Leu Val Trp Thr Leu Ser Pro Leu Phe Pro Ser Leu Cys Ala Glu Arg
210 215 220

Met
225

<210> SEQ ID NO 46
<211> LENGTH: 250
<212> TYPE: PRT
<213> ORGANISM: Homo sapiens
<220> FEATURE:
<223> OTHER INFORMATION: TREM-1

<400> SEQUENCE: 46

Met Arg Lys Thr Arg Leu Trp Gly Leu Leu Trp Met Leu Phe Val Ser
1 5 10 15

Glu Leu Arg Ala Ala Thr Lys Leu Thr Glu Glu Lys Tyr Glu Leu Lys
20 25 30

Glu Gly Gln Thr Leu Asp Val Lys Cys Asp Tyr Thr Leu Glu Lys Phe
35 40 45

Ala Ser Ser Gln Lys Ala Trp Gln Ile Ile Arg Asp Gly Glu Met Pro

-continued

```
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
        115                 120                 125

Ile Arg Leu Val Val Thr Lys Gly Phe Ser Gly Thr Pro Gly Ser Asn
    130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Glu Lys Ser Met Thr Phe Gly Ile
        195                 200                 205

Arg Arg Leu Asp Val Glu Ser His Pro Leu Pro Pro Leu His Thr Gly
    210                 215                 220

His Phe Arg Ile Ser Gln Phe Phe Ser Gln Ala Gly Thr Gln Ser Leu
225                 230                 235                 240

His Ser Cys Tyr Lys Gly Lys Pro Thr Pro
                245                 250


<210> SEQ ID NO 47
<211> LENGTH: 351
<212> TYPE: DNA
<213> ORGANISM: Artificial Sequence
<220> FEATURE:
<223> OTHER INFORMATION: VH

<400> SEQUENCE: 47

gaggtgcagc tggtggagtc tggaggcgct ctcgtgaagc ctggcggctc tctcagactc     60

tcttgcgctg cctccggctt caacatcgac aacacctaca tccactgggt gcggcaggct    120

cctggaaagg gactcgagtg gatcggaaga atcgaccctg ctggagggag aaccaagtac    180

gaccccaagg tcaaggggcg gttcaccatc tctgccgaca cctccaagaa caccgcctac    240

ctgcagatga acagcctcaa gaccgaggac accgctgtct actactgcac cgggcactac    300

ggagggacaa tggattactg gggacagggg acactcgtca ccgtctctag c             351


<210> SEQ ID NO 48
<211> LENGTH: 351
<212> TYPE: DNA
<213> ORGANISM: Artificial Sequence
<220> FEATURE:
<223> OTHER INFORMATION: VH

<400> SEQUENCE: 48

gaggtgcagc tggtggagtc tggaggcgct ctcgtgaagc ctggcggctc tctcagactc     60

tcttgcgctg cctccggctt caacatcgga aacacctaca tccactgggt gcggcaggct    120

cctggaaagg gactcgagtg gatcggaaga atcgaccctg ctggagggag aaccaagtac    180

tccccaaagg tccaggggcg gttcaccatc tctgccccta cctccaagaa caccgcctac    240

ctgcagatga acagcctcaa gaccgaggac accgctgtct actactgtac cgggcacagg    300
```

ggagggacaa tggattactg gggacagggg acactcgtca ccgtctctag c 351

<210> SEQ ID NO 49
<211> LENGTH: 351
<212> TYPE: DNA
<213> ORGANISM: Artificial Sequence
<220> FEATURE:
<223> OTHER INFORMATION: VH

<400> SEQUENCE: 49
gaggtgcagc tggtggagtc tggaggcgct ctggtgaagc ctggcggctc tctgagactg 60
tcttgcgctg cctccggctt caacatcggc aacacctaca tccactgggt gcggcaggct 120
cctggaaagg gactggagtg ggtgggcaga atcgatcctg ctggcggaag aaccaagtac 180
gccccaaagg tgaagggacg gttcaccatc tctgccgacg actccaagaa caccgcctac 240
ctccagatga actccctcaa gaccgaggac accgctgtgt actactgtac cggacaccgg 300
ggagggacaa tggattactg gggacagggg acactcgtga ccgtgtcttc c 351

<210> SEQ ID NO 50
<211> LENGTH: 351
<212> TYPE: DNA
<213> ORGANISM: Artificial Sequence
<220> FEATURE:
<223> OTHER INFORMATION: VH

<400> SEQUENCE: 50
gaggtgcagc tggtggagtc tggaggcgct ctggtgaagc ctggcggctc tctgagactg 60
tcttgcgctg cctccggctt caacatcggc aacacctaca tccactgggt gcggcaggct 120
cctggaaagg gactggagtg gatcggcaga atcgaccctg ctggcggaag aaccaagtac 180
gccccaaagg tgcagggacg gttcaccatc tctgccgaca cctccaagaa caccgcctac 240
ctccagatga actccctcaa gaccgaggac accgccgtgt actactgcac cggacactac 300
ggagggacaa tggattactg gggacagggg acactcgtga ccgtgtcttc c 351

<210> SEQ ID NO 51
<211> LENGTH: 351
<212> TYPE: DNA
<213> ORGANISM: Artificial Sequence
<220> FEATURE:
<223> OTHER INFORMATION: VH

<400> SEQUENCE: 51
gaggtgcagc tggtggagtc tggaggcgct ctggtgaagc ctggcggctc tctcagactc 60
tcttgcgctg cctccggctt caacatcgga aacacctaca tccactgggt gcggcaggct 120
cctggaaagg gactcgagtg ggtcggaaga atcgatcctg ctggagggag aaccaagtac 180
gccccaaagg tcaaggggcg gttcaccatc tctgccgacg actccaagaa caccctgtac 240
ctccagatga acagcctcaa gaccgaggac accgctgtct actactgtac cgggcacagg 300
ggagggacaa tggattactg gggacagggg acactcgtca ccgtctctag c 351

<210> SEQ ID NO 52
<211> LENGTH: 351
<212> TYPE: DNA
<213> ORGANISM: Artificial Sequence
<220> FEATURE:
<223> OTHER INFORMATION: VH

<400> SEQUENCE: 52
gaggtgcagc tggtggagtc tggaggcgct ctggtgaagc ctggcggctc tctgagactg 60
tcttgcgctg cctccggctt caacatcaag aacacctaca tccactgggt gcggcaggct 120
cctggaaagg gactggagtg gatcggccgg atcgaccctg ctaacggcaa caccaagtac 180
gccccaaagg tgcagggacg gttcaccatc tctgccgaca cctccaagaa caccgcctac 240
ctccagatga actccctcaa gaccgaggac accgccgtgt actactgcac cggacactac 300
ggatccacca tggactactg gggacagggg acactcgtga ccgtgtcttc c 351

<210> SEQ ID NO 53
<211> LENGTH: 333
<212> TYPE: DNA
<213> ORGANISM: Artificial Sequence
<220> FEATURE:
<223> OTHER INFORMATION: VL

<400> SEQUENCE: 53
gagatcgtcc tgacccagtc tcctgccacc ctgtctctct ctcccggcga aagagccacc 60
ctctcttgca gagcctccga gtccgtggac aactacggca tctccttcct caactggtac 120
caacagaagc ctggacaggc ccctaggctc ctcatctacg ctgctgagta caggggaagg 180
ggaatccccg ctaggttctc tgggagtggg tctgggaccg acttcaccct caccatctcc 240
tccctcgagc ccgaggactt cgctgtgtac tactgccagc agtcccggca cgtgccttac 300
accttcgggc aggggaccaa ggtggagatc aag 333

<210> SEQ ID NO 54
<211> LENGTH: 333
<212> TYPE: DNA
<213> ORGANISM: Artificial Sequence
<220> FEATURE:
<223> OTHER INFORMATION: VL

<400> SEQUENCE: 54
gagatcgtcc tgacccagtc tcctgccacc ctgtctctgt ctcccggcga gagagccacc 60
ctgtcttgca gagcctccca gtccgtgtcc aactacggca tctccttcct gaactggtac 120
caacagaagc ctggccaggc ccctagactc ctcatctacg ccgcctctta ccagaagcgg 180
ggcatccccg ccagattctc tggatctgga tctggaaccg acttcaccct caccatctcc 240
tccctcgagc ccgaggactt cgcagtgtac tactgccagc agtcctccaa cttcccctgg 300
accttcggac aggggaccaa ggtggagatc aag 333

<210> SEQ ID NO 55
<211> LENGTH: 333
<212> TYPE: DNA
<213> ORGANISM: Artificial Sequence
<220> FEATURE:
<223> OTHER INFORMATION: VL

<400> SEQUENCE: 55
gagatcgtcc tgacccagtc tcctgccacc ctgtctctgt ctcccggcga gagagccacc 60
ctgtcttgca gagcctccca gtccgtgtcc aactacggca tctccttcct gaactggtac 120
caacagaagc ctggccaggc ccctagactc ctcatctacg ccgccgagta cagaggcaga 180
ggcatccccg ccagattctc tggatctgga tctggaaccg acttcaccct caccatctcc 240
tccctcgagc ccgaggactt cgcagtgtac tactgccagc agtcctccaa cgtgccctac 300
accttcggcc aggggaccaa ggtggagatc aag 333

<210> SEQ ID NO 56
<211> LENGTH: 333
<212> TYPE: DNA
<213> ORGANISM: Artificial Sequence
<220> FEATURE:
<223> OTHER INFORMATION: VL

<400> SEQUENCE: 56
gagatcgtcc tgacccagtc tcctgccacc ctgtctctgt ctcccggcga gagagccacc 60
ctgtcttgca gagcctccca gtccgtgtcc aactacggca tctccttcct gaactggtac 120
caacagaagc ctggccaggc ccctagactg ctcatctacg ccgccgagta ccagggcaga 180
ggcatccctg ccagattctc tggatctgga tctggaaccg acttcaccct caccatctcc 240
tccctcgagc ccgaggactt cgcagtgtac tactgccagc agtcctccaa cgtgccctac 300
accttcggcc aggggaccaa gctcgagatc aag 333

<210> SEQ ID NO 57
<211> LENGTH: 333
<212> TYPE: DNA
<213> ORGANISM: Artificial Sequence
<220> FEATURE:
<223> OTHER INFORMATION: VL

<400> SEQUENCE: 57
gagatcgtcc tgacccagtc tcctgccacc ctgtctctct ctcccggcga aagagccacc 60
ctctcttgca gagcctccca gtccgtgtcc aactacggaa tctccttcct caactggtac 120
caacagaagc ctggacaggc ccctaggctc ctcatctacg cagctgagta cagggctagg 180
ggaatccccg ctaggttctc tggatctggg agtgggaccg acttcaccct caccatctcc 240
tccctggagc ccgaggactt cgctgtgtac tactgccagc agtcctccaa cgtgccttac 300
accttcgggc aggggaccaa ggtggagatc aag 333

<210> SEQ ID NO 58
<211> LENGTH: 333
<212> TYPE: DNA
<213> ORGANISM: Artificial Sequence
<220> FEATURE:
<223> OTHER INFORMATION: VL

<400> SEQUENCE: 58
gagatcgtcc tgacccagtc tcctgccacc ctgtctctgt ctcccggcga gagagccacc 60
ctgtcttgca gagcctccga gtccgtggac aactacggca tctccttcat gaactggttc 120
caacagaagc ctggccaggc ccctagactg ctcatctacg ccgcctctaa ccagggctct 180
ggcatccccg ccagattctc tggatctgga tctggaaccg acttcaccct caccatctcc 240
tccctcgagc ccgaggactt cgcagtgtac ttctgccagc agtccaagga ggtcccttgg 300
acctttgggc aggggaccaa ggtggagatc aag 333

<210> SEQ ID NO 59
<211> LENGTH: 585
<212> TYPE: PRT
<213> ORGANISM: Homo sapiens
<220> FEATURE:
<223> OTHER INFORMATION: HSA

<400> SEQUENCE: 59

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln

-continued

```
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445
```

```
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585


<210> SEQ ID NO 60
<211> LENGTH: 585
<212> TYPE: PRT
<213> ORGANISM: Homo sapiens
<220> FEATURE:
<223> OTHER INFORMATION: HSA

<400> SEQUENCE: 60

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

<210> SEQ ID NO 61
<211> LENGTH: 12
<212> TYPE: PRT
<213> ORGANISM: Artificial Sequence -continued

```
<220> FEATURE:
<223> OTHER INFORMATION: LR12

<400> SEQUENCE: 61

Leu Gln Glu Glu Asp Ala Gly Glu Tyr Gly Cys Met
1               5                   10
```